US011046668B2

(12) United States Patent
Rajashekara et al.

(10) Patent No.: US 11,046,668 B2
(45) Date of Patent: Jun. 29, 2021

(54) SMALL MOLECULE ANTIMICROBIALS

(71) Applicant: Ohio State Innovation Foundation, Columbus, OH (US)

(72) Inventors: Gireesh Rajashekara, Columbus, OH (US); Ulyana Munoz Acuna, Columbus, OH (US); Janet Antwi, Columbus, OH (US); Esperanza Carcache de Blanco, Columbus, OH (US); James Fuchs, Columbus, OH (US); Anand Kumar, Columbus, OH (US); Corey Nislow, Columbus, OH (US); Melvin Pascall, Columbus, OH (US); Zilu Wan, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 378 days.

(21) Appl. No.: 16/083,811

(22) PCT Filed: Mar. 6, 2017

(86) PCT No.: PCT/US2017/020968
§ 371 (c)(1),
(2) Date: Sep. 10, 2018

(87) PCT Pub. No.: WO2017/155890
PCT Pub. Date: Sep. 14, 2017

(65) Prior Publication Data
US 2020/0299259 A1 Sep. 24, 2020

Related U.S. Application Data

(60) Provisional application No. 62/361,846, filed on Jul. 13, 2016, provisional application No. 62/306,986, filed on Mar. 11, 2016.

(51) Int. Cl.
| | | |
|---|---|---|
| C07D 401/06 | (2006.01) | |
| C07D 333/34 | (2006.01) | |
| A01N 43/10 | (2006.01) | |
| A01N 43/40 | (2006.01) | |
| A61P 31/04 | (2006.01) | |
| A61K 9/00 | (2006.01) | |
| A61K 9/70 | (2006.01) | |

(52) U.S. Cl.
CPC ........... *C07D 401/06* (2013.01); *A01N 43/10* (2013.01); *A01N 43/40* (2013.01); *A61P 31/04* (2018.01); *C07D 333/34* (2013.01); *A61K 9/0014* (2013.01); *A61K 9/0053* (2013.01); *A61K 9/70* (2013.01)

(58) Field of Classification Search
CPC ..... C07D 401/06; C07D 333/34; A61P 31/04; A01N 43/10; A01N 43/40; A61K 9/0014; A61K 9/0053; A61K 9/70
USPC ...................................................... 514/339
See application file for complete search history.

(56) References Cited

U.S. PATENT DOCUMENTS

| | | |
|---|---|---|
| 5,543,164 A | 8/1996 | Krochta et al. |
| 7,160,558 B2 | 1/2007 | Petereit et al. |
| 2011/0034513 A1 | 2/2011 | Kreft et al. |

FOREIGN PATENT DOCUMENTS

| | | |
|---|---|---|
| WO | 0234718 A1 | 5/2002 |
| WO | 2015084938 A1 | 6/2015 |

OTHER PUBLICATIONS

Ohio State University Foundation, PCT/US2017/020968, filed Mar. 6, 2017, "International Preliminary report on Patentability", 5 pages, dated Sep. 11, 2018.
Appendini et al., "Review of antimicrobial food packaging", Innovative Food Science & Emerging Technologies, vol. 3, pp. 113-126, 2002.
Biji et al., "Smart packaging systems for food applications: a review", J Food Sci Technol, vol. 52(10), pp. 6125-6135, Feb. 17, 2015.
Bourtoom, T., "Edible films and coatings: characteristics and properties", International Food Research Journal, vol. 15(3), 13 pages, 2008.
Darmona-Ribeiro et al., "Cationic Antimicrobial Polymers and Their Assemblies", International Journal of Molecular Sciences, vol. 14, pp. 9906-9946, May 10, 2013.
Erkmen et al., "General Characteristics of Edible Films", Journal of Food Biotechnology Research, vol. 2, No. 1:3, pp. 1-4, Feb. 5, 2018.
Islam et al., "Control of Listeria monocytogenes on Turkey Frankfurters by Generally-Recognized-as-safe Preservatives", Journal of Food Protection, vol. 65, No. 9, pp. 1411-1416, Apr. 5, 2002.
Janjarasskul et al., "Edible Packaging Materials", Annu. Re.Food Sci. Technol., vol. 1, pp. 415-448 Jan. 12, 2010.
Krochta, John M., "Proteins as Raw Materials for Films and Coatings: Definitions, Current Status, and Opportunities", Protein-Based Films and Coatings, Chapter 1, 41 pages, 2002.
Kumar et al., "Novel Anti-Campylobacter Compounds Identified Using High Throughput Screening of a Pre-Selected Enriched Small Molecules Library", Frontiers in Microbiology, vol. 7, Article 405, 12 pages, Apr. 6, 2016.
Lahellec, et al., "Growth Effect of Sorbate and Selected Antioxidants on Toxigenic Strains of *Staphylococcus aureus*", Journal of Food Protection, vol. 44, No. 7, pp. 531-534 Jul. 1981.

(Continued)

*Primary Examiner* — Kristin A Vajda
(74) *Attorney, Agent, or Firm* — McKee, Voorhees & Sease, PLC

(57) ABSTRACT

Compounds and compositions of matter are provided that are small molecule antimicrobials. The compounds are selected from JH-144, TH-04 or TH-08 or combinations thereof. Compositions of matter are provided which in an embodiment may comprise a carrier, and in further embodiments may comprise a pharmaceutically acceptable excipient, film, biofilm or edible film. Methods of use are provided in which the composition may be administered to a subject in need thereof, and in an embodiment where the subject has a bacterial infection. Other embodiments provide the composition may be contacted with surface to eliminate or reduce bacteria.

20 Claims, 31 Drawing Sheets

(56) References Cited

OTHER PUBLICATIONS

Lee et al., "Mapping the Cellular Response to Small Molecules Using Chemogenomic Fitness Signatures", Science, vol. 344(6180), pp. 208-211, Apr. 11, 2014.

Liu et al., "Preparation and characterization of sorbitol modified nanoclay with high amylose bionanocomposites", Carbohydrate Polymers, vol. 85, pp. 97-104, Mar. 2, 2011.

Malhotra et al., "Antimicrobial food packaging: potential and pitfalls", Frontiers in Microbiology, vol. 6, Article 611, pp. 1-9, Jun. 2015.

Marians et al., "Mechanism of Quinolone Action: A Drug-Induced Structural Perturbation of the DNA Precedes Strand Cleavage by Topoisomerase IV", Journal of Biological Chemistry, vol. 272, No. 14, pp. 9401-9409, Apr. 4, 1997.

Moir et al., "Inhibition, Injury, and Inactivation of Four Psychrotrophic Foodborne Bacteria by the Preservatives Methyl p-Hydroxybenzoate and Potassium Sorbate", Journal of Food Protection. vol. 55, No. 5, pp. 360-366, May 1992.

Pathania et al., "Chemical genomics in *Escherichia coli* identifies an inhibitor of bacterial lipoprotein targeting", Nature Chemical Biology, vol. 5, No. 11, pp. 849-856, Nov. 2009.

"5-Chloro-N-(4-fluorobenzyl) thiophene-2-sulfonamide", PubChem Compound Summary for CID 893742, 13 pages, Jul. 9, 2005.

"Ozwukgoyemkark-Uhfffaoysa-N", PubChem Compound Summary for CID 28025864, 10 pages, May 28, 2009.

"Fvwniyrfdwmgrg-Uhfffaoysa-N", PubChem Compound Summary for CID 45223051, 13 pages, Apr. 27, 2010.

Reddy et al., "Inhibition of Clostridium botulinum by Antioxidants, Phenols, and Related Compounds", Applied and Environmental Microbiology, vol. 43, No. 4, pp. 835-839, Dec. 14, 1981.

Schlaad et al., "Glycopolymer vesicles with an asymmetric membrane", Chem. Comm., pp. 1478-1480, Jan. 30, 2009.

Sofos et al., "Antimicrobial Activity of Sorbate", Journal of Food Protection. vol. 44, No. 8, pp. 614-622, Aug. 1981.

Sung et al., "Antimicrobial agents for food packaging applications", Trens in Food Science & Technology, vol. 33, pp. 110-123, 2013.

Wallace et al., "Compound prioritization methods increase rates of chemical probe discovery in model organisms", Chem. Biol., vol. 18(10), pp. 1273-1283, Oct. 28, 2011.

*FIG. 2 (A & B)*

SMALL MOLECULE ANTIMICROBIALS

REFERENCE TO RELATED APPLICATION

This application claims priority to previously filed and provisional application U.S. Ser. No. 62/361,846, filed Jul. 13, 2016, the contents of which are incorporated herein by reference in its entirety and provisional application U.S. Ser. No. 62/306,986 filed Mar. 11, 2016 the contents of which are incorporated herein by reference in its entirety.

FIELD OF THE INVENTION

The present disclosure is related to broad-spectrum antimicrobial compounds, compositions comprising the antimicrobial compounds, and methods of treating/preventing bacterial infections with the antimicrobial compounds.

BACKGROUND OF THE INVENTION

Foodborne illnesses can result in major public health implications in the U.S. and around the world. According to recently published CDC (Centers for Disease Control and Prevention) data foodborne diseases account for approximately 8 million illnesses, and 9,000 deaths each year in the U.S. alone (CDC, 2011). The epidemiology of foodborne diseases is rapidly changing as newly recognized pathogens emerge and well-studied pathogens increase in prevalence or associate with new food vehicles. Apart from acute gastroenteritis, some foodborne diseases may cause chronic illness or disability. Listeriosis, for instance, can cause miscarriages or meningitis in patients with pre-existing chronic diseases (Schuchat et al., 1991). As meat and meat products are the major source of foodborne infection and the most important link between food-producing animal and humans, the study of foodborne pathogens isolated from meat and poultry is indispensable.

Microbial contamination can reduce the shelf life of foods and increase the risk of foodborne illness. This is a major worldwide public health concern. According to statistical data from the Center for Disease Control (CDC), five pathogen types account for over 90% of the estimated food-related deaths. Among these microorganisms, bacterial pathogens are *Salmonella, Listeria, Campylobacter, E. coli* 0157:H7 and *Vibrio* (CDC, 2014) a significant causes of foodborne illnesses. Among these five pathogens, illness associated with *Campylobacter*, termed "campylobacteriosis", is one of the most common forms of bacterial foodborne gastroenteritis in developed countries (Blaser et al., 2008). Apart from *Campylobacter* spp., the CDC estimates that *E. coli* 0157:H7 causes approximately 73,000 illnesses and 60 deaths each year in the United States, in which 85% of these cases are attributed to foodborne transmission. Listeriosis, another serious infection usually caused by eating foods contaminated with the bacterium *Listeria monocytogenes*, is also an important public health problem. It is estimated that in the U.S., there are about 2500 cases with 500 deaths annually attributed to listeriosis. The spectrum of listeriosis is broad, ranging from asymptomatic infection and flu-like symptoms, to miscarriage, stillbirth, and meningitis (CDC, 2014).

Antimicrobial therapy is one of the most effective ways to prevent and control bacterial diseases. Currently, the most commonly used antimicrobials are macrolides (erythromycin) and fluoroquinolones (ciprofloxacin) with tetracycline used as an alternative (Moore et al., 2006). However, as the use of antimicrobials for therapy and prophylaxis increase in both human and animal medicine, increasing numbers of bacteria have developed resistance to these antimicrobials. As these foodborne pathogens are projected to remain top ten bacterial conditions globally, and several antibiotics are no longer effective in treatment, a new generation of effective antimicrobials is critically needed. High-throughput, robust, cost-effective, phenotypic cell-based screening is one such amenable approach to expedite antimicrobials discovery. Numerous studies (both laboratory and commercial plant-based) investigated potential interventions in processing plants to reduce *Campylobacter* on poultry carcasses. Evaluated measures included freezing, hot water treatment, irradiation, and chemical decontamination. Depending on the specific processing stage, several practices, such as time, temperature, pH, direction of water flow, and antimicrobial treatments can substantially affect the level of carcass contamination by Berrang, M. E., W. R. Windham, and R. J. Meinersmann. 2011. *Campylobacter, Salmonella*, and *Escherichia coli* on broiler carcasses subjected to a high pH scald and low pH postpick chlorine dip. Poult. Sci. 90:896-900.

An active food packaging system can serve as a nonthermal method to reduce foodborne pathogen contamination in food. By definition, active packaging is defined as packaging in which subsidiary constituents have been deliberately included into the matrix or coated to the packaging material, in the packaging headspace, to enhance the performance of the packaging system (Robertson, 2006). One application of active packaging is to incorporate antimicrobial substances that can control microbial contamination by reducing the growth rate and maximum population by extending the lag-phase of the target microorganism (Han, 2000). The advantage of this is that the antimicrobial agent does not have to be applied directly to the food where it could be deactivated by additives (in the food), or by the processing methods, or by long term exposure before the food is ready for consumption. With active packaging, the antimicrobial agent can be made to contact the food at a strategic time and it could be designed to be released into the product at a control rate, thus its efficacy would be enhanced in terms of time and concentration. The use of active antimicrobial packaging for the control of microorganisms on food products is widely reported in the literature (Appendini, P., Hotchkiss, J. H. 2003, Review of antimicrobial food packaging. *Innovative Food Science and Emerging Technologies*. Vol. 3, 113-126).

Five pathogens that account for over 90% of estimated food-related deaths: *Samonella, Listeria, Campylobacter, E. coli* O157:H7 and *Vibrio* (CDC, 2011can result in a self-limiting diarrheal illness in humans, however severe invasive diseases or prolonged illnesses in immune-compromised individuals can occur and may require antimicrobial therapy.

The genus *Salmonella* currently includes more than 2400 different serotypes. *Salmonella* species are unique in the environment and can colonize and cause disease in a variety of animals. Salmonellosis, caused by non-typhoidal *Salmonella* strains, typically results in a self-limiting diarrhea that do not need antimicrobial therapy, while in some rare cases, the infections of *Salmonella enterica* can lead to life-threatening systematic syndrome which require effective chemotherapy (Lee L. A., Puhr N. D., Maloney E. K., Bean N. H., Tauxe R. V., 1994, Increase in antimicrobial-resistant *Salmonella* infections in the United States, 1989-1990, J. Infect. Dis. VOl. 170, pp. 128-134). For *Salmonella* spp., in some cases, a rapid spread through the animal production systems seems to have occurred at a global level in 1980s (Rodrigue, D. C., Tauxe, R. V., Rowe, B., 1990. International increase in *Salmonella* Enteritidis: a new pandemic? Epidemiology and Infection 105, 21-27). It is reported that *S.enteritidis* appeared simultaneously around most of European countries and U.S., and also spread into the poultry production systems of developing countries later in the 1990s (Matope, G., Schlundt, J., Makaya, P. V., Aabo, S., Baggesen, D. L., 16 J. Schlundt/International Journal of Food Microbiology 78 (2002) 3-17 1998. *Salmonella* Enteritidis in poultry: an emerging zoonosis in Zimbabwe. Zimbabwe Veterinary Journal 29, 132-138).

*Campylobacters* are thin, curved, motile gram-negative rods. They are generally micro-aerophilic, though some strains are aerobic and anaerobic. Currently, *campylobacters* are recognized as the leading cause of foodborne gastroenteritis in the U.S. and one of the most frequent causes of acute bacterial enteritis worldwide (Mead P. S., Slutsker L., Dietz V., McCaig L. F., Bresee J. S., Shapiro C., 1999, Food-related illness and death in the United States, Emerg. Infect. Dis., pp. 5607-5625). Gastroenteritis caused by *Campylobacter* is an acute diarrheal disease that typically causes high fever, abdominal cramping, and diarrhea that last from several days to more than one week. It is to be noted that *C. jejuni*, and *C. coli* (clinically indistinguishable) are the most common species associated with diarrheal illness, causing more than 95% of *Campylobacter enteritis* (Harris N. V., Weiss N. S., Nolan C. M., 1986, The role of poultry and meats in the etiology of *Campylobacter jejuni/coli enteritis*, Am. J. Public Health Vol. 76, pp. 407-411). The reports of campylobacteriosis cases have been continuously increasing in many parts of the world, as proved by statistical data from Texas Department of State Health Services. Most infections are sporadic single cases resulting from the consumption of contaminated food, milk or uncooked and mishandled poultry (Friedman C. R., Neimann J., Wegener H. C., Tauxe R. V., 2000, In: I. Nachamkin, M. J. Blaser (Eds.), Campylobacter, 2nd ed., ASM Press, Washington D.C., pp. 130-130).

Shiga-toxin-producing *Escherichia coli* (STEC) was first recognized as an emerging human pathogen in 1982 when *E. coli* 0157:H7 was implicated in two outbreaks of hemorrhagic colitis associated with consumption of uncooked beef (Wells J. G., Davis B. R., Wachsmuth I. K., Riley L. W., Remis R. S., Sokolow R., et al., 1983, Laboratory investigation of hemorrhagic colitis outbreaks associated with a rare *Escherichia coli* serotype, J. Clin. Microbiol. Vol. 185, pp. 12-20). Human infection with STEC can lead to nonbloody diarrhea or bloody diarrhea, or more serious and fatal syndrome such as hemorrhagic colitis and hemolytic uremic syndrome. It is proved that the most important virulence factors associated with STEC infection are Shiga toxins (stx1, stx2 or variants) (Schlundt J., 2002, New directions in foodborne disease prevention, International Journal of Food Microbiology Vol. 78, pp. 3-17).

*Vibrio vulnificus* is a gram-negative bacterium commonly found in estuarine and coastal habitats throughout the northern Gulf of Mexico. This species is an opportunistic human pathogen that can cause primary septicemia, wound infection and gastroenteritis (Strom M. S., Paranjpye R. N., 2000, Epidemiology and pathogenesis of *Vibrio vulnificus*. Microbes Infect. Vol 2, pp. 177-188). Comparing with gastroenteritis, primary septicemia is the most common and severe syndrome caused by *V. vulnificus*, with mortality rate of more than 50% (Blake P. A., 1979, Disease caused by a marine vibrio—clinical characteristics and epidemiology. N. Engl. J. Med. Vol. 300, pp. 1-5). Most reported cases revealed that consumption of raw shellfish and eastern oyster is the main cause of infections (Strom et al., 2000). Besides, *V. vulnificus* can produce severe skin and soft tissue infections in patients with pre-existing wounds who come in contact with the bacterium via seawater or by handling seafood (Howard R. J., Lieb S., 1988, Soft-tissue infections caused by halophilic marine vibrios. Arch. Surg. Vol. 123, pp. 245-249).

Many studies indicated that *Listeria monocytogenes* grows well at refrigeration temperatures and with minimal nutrients, and is able to survive and even grow in plants, soil and water (Schlundt J., 2002, New directions in foodborne disease prevention, International Journal of Food Microbiology Vol. 78, pp. 3-17). The foodborne transmission has been recognized as a major source of human listeriosis since 1982, though the first reported human listeriosis was in 1929. The widespread nature of *L. monocytogenes* allows easy access to food products during various phases of production, processing, manufacturing, and distribution, thus it has been found in many food products, including fresh vegetables, raw milk, raw meats, and eggs. Many illnesses are associated with refrigerated processed foods (ready-to-eat) consumed without prior cooking or reheating. The incidence of listeriosis has increased over the past two decades throughout the world. It is estimated by CDC that in the U.S., there are 2500 cases with 500 deaths attributed to listeriosis annually, mostly involving pregnant women, newborn babies, the elderly, and immune-compromised people. The spectrum of listeriosis is broad, ranging from asymptomatic infection and flu-like symptoms, to miscarriage, stillbirth, and meningitis (Robert R., 2003).

The prevention and control of foodborne disease depends on Good Manufacturing Practices (GMP) of food production, including the handling of raw ingredients and the preparation of finished products. If not, hazards can be introduced at any point from the farm to the table. The introduction of the Hazard Analysis Critical Control Point (HACCP) system greatly improved hygiene control in processing plants. Such programs require food industries to identify points in food production where contamination may occur and target resources toward processes that reduce or eliminate foodborne hazards (Goodfellow, S. J. 1995. Implementation of the HACCP program by meat and poultry slaughterers. In HACCP in Meat, Poultry and Fish Processing, eds. A. M. Pearson & T. R. Dutson, pp. 58-71. Glasgow, UK, Blackie Academic & Professional). However, infections cannot be fully eliminated since young animals or poultry are highly susceptible to pathogens. Milner and Shaffer indicated that the infective dose of *S. typhimurium* for one-day-old birds with an oral administration was as low as 10 CFUs (Milner K. C., Shaffer, M. F. 1952. Bacteriologic studies of experimental *Salmonella* infections in chicks. Journal of Infectious Diseases Vol. 90, pp. 81-96). This deficiency could be overcome by oral administration of a saline suspension with mature micro-flora from adult birds. In this way, adult-type microflora would be established in young birds and thus prevent them from pathogenic infections by the phenomenon known as "competitive exclusion" (Rantala, M., Nurmi, E. 1973. Prevention of the growth of *Salmonella infantis* in chicks by the flora of the alimentary tract of chickens. British Poultry Science Vol. 14, pp. 627-30).

As can be seen, there is a continuing need to develop new antimicrobials. Other objects, aspects and advantages of this invention will be apparent to one skilled in the art in view of the following disclosure, the drawings, and the appended claims.

SUMMARY OF THE INVENTION

Applicants have synthesized new antimicrobial compounds JA-144, TH-04, or TH-08 which form the basis of this application. The invention includes these compounds as well as derivatives, modifications, or pharmaceutically acceptable salts thereof. In another embodiment included herein is an antimicrobial compound having the formula for JA-144, TH-08, or TH-04 as set forth below:

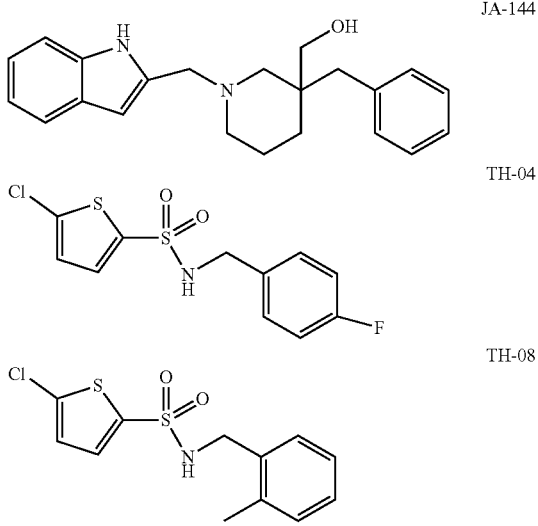

Also included are antimicrobial compositions including the aforementioned compounds and a carrier, preferably a film carrier, more preferably an edible film. Yet a further embodiment includes methods of treating a subject, surface or substrate in need of treatment for a bacterial contamination or infection. Subjects or surfaces are then contacted with one or more the compositions of the invention to reduce, prevent or treat bacterial infection. In still further embodiments the antimicrobial compounds are impregnated within a film coating to be applied to a substrate or food substance. An embodiment provides the film may be a packaging material in contact with a surface or food substance. In yet another embodiment the substrate or surface is a food surface or substrate and the film is an edible film coating.

In still another embodiment, the invention includes methods of reducing the antimicrobial activity of Gram-negative bacteria, Gram-positive bacteria, or bacteria that are neither Gram-positive nor Gram-negative. In a still further embodiment the Gram-negative bacteria is *Escherichia coli, Pseudomonas aeruginosa, Candidatus liberibacter, Agrobacterium tumefaciens, Branhamella catarrhalis, Citrobacter diversus, Enterobacter aerogenes, Klebsiella pneumoniae, Proteus mirabilis, Salmonella* typhimurium, Neisseria meningitidis, Serratia marcescens, Shigella sonnei, Shigella boydii, Neisseria gonorrhoeae, Acinetobacter baumannii, *Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Vibrio cholera, Shigella boydii, Morganella morganii, Edwardsiella tarda, Campylobacter jejuni, Campylobacter coli* or *Haemophilus influenzae*. In another embodiment the Gram-positive bacteria is a species of *Bacillus, Listeria, Staphylococcus, Streptococcus, Enterococcus, Corynebacterium, Propionibacterium* or *Clostridium*. In yet another embodiment the Gram-positive bacteria is *Staphylococcus aureus, Staphylococcus epidermidis, Enterococcus faecium, Enterococcus faecalis, Streptococcus pyogenes, Bacillus cereus,* or *Bacillus anthraces*.

DETAILED DESCRIPTION OF THE INVENTION

Figure 1:
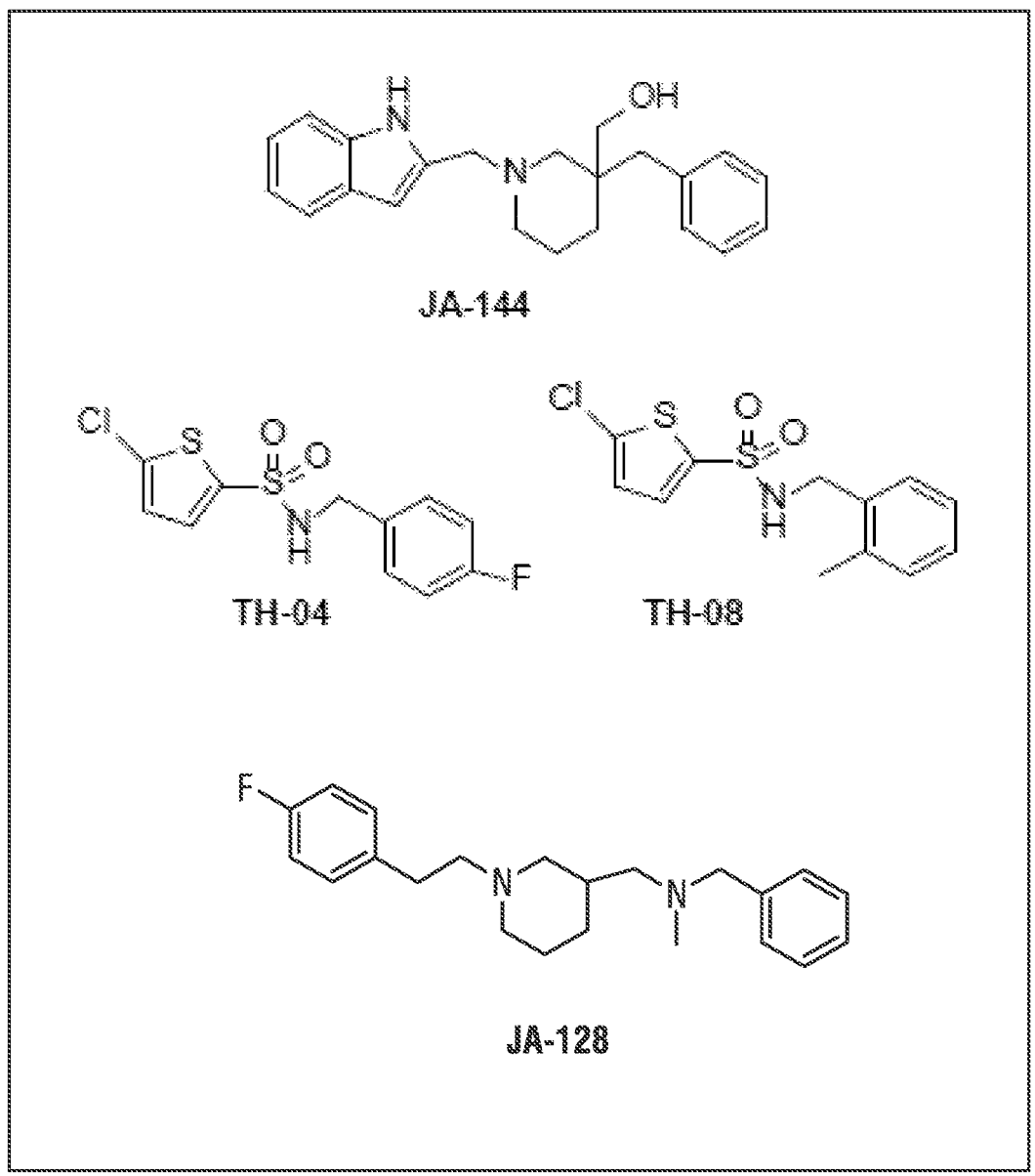
FIG. 1 is a graph showing the formula of compounds JA-144, TH-04, TH-08 and JA-128.

Described here are antimicrobial compounds JA-144, TH-04, or TH-08 (sometimes here referred to as TH-4 or TH-8) and which includes derivatives, modifications, or pharmaceutically acceptable salts thereof.

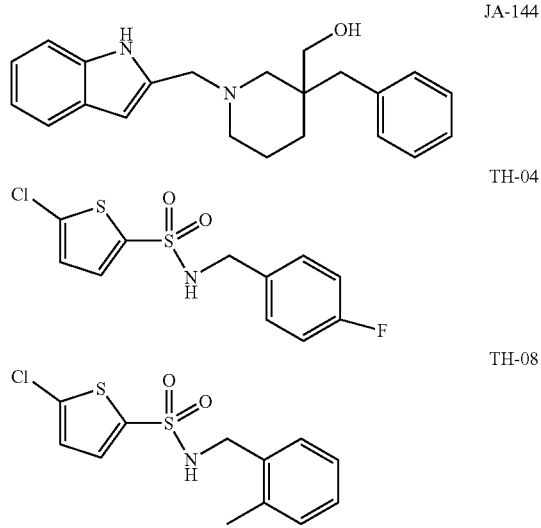

Examples of these are provided in the Examples below. Derivatives of the compounds include, but are not limited to, any salt, ester, acids, bases, solvates, hydates, and prodrugs. Derivatives, modifications and pharmaceutically acceptable salts retain the functional properties described herein.

"Pharmaceutically acceptable salts" includes derivatives of the disclosed compounds wherein the parent compound is modified by making an acid or base salt thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-CH_2)_n-COOH$ where n is 0-4, and the like. The pharmaceutically acceptable salts of can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable.

The term "substituted", as used herein, means that any one or more hydrogens on the designated atom or group is replaced with a group at least one group selected from a halide (F—, Cl—, Br—, I—), a hydroxyl, a $C_1$ to $C_{20}$ alkoxy, a cyano, a $C_1$ to $C_{20}$ alkyl, a $C_2$ to $C_{16}$ alkenyl, a $C_2$ to $C_{16}$ alkynyl, a $C_6$ to $C_{20}$ aryl, a $C_7$ to $C_{13}$ arylalkyl, a $C_7$ to $C_{13}$ aryloxyalkyl, a $C_7$ to $C_{13}$ arylthioalkyl, a $C_1$ to $C_{20}$ heteroalkyl, a $C_3$ to $C_{20}$ cycloalkyl, and a $c_5$ to $C_{15}$ heterocycloalkyl, provided that the designated atom's normal valence is not exceeded. When a substituent is oxo (i.e., =O), then 2 hydrogens on the carbon atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Applicants have synthesized novel compounds, from those identified from a screen of a small molecule library of 4, 182 compounds for bactericidal activity against *C. jejuni*. 781 compounds were identified possessing bactericidal or bacteriostatic activity. Through secondary screens applicants identified several compounds with narrow spectrum activity specific to *C. jejuni* and *C. Coli*. From these, Applicants then synthesized 15 derivatives of one of the compounds and from these, three superior novel derivatives were identified.

In one aspect, provided herein are methods of treating an animal subject in need of treatment for a bacterial infection, comprising administering to the individual an antimicrobial compound or composition as described herein. The bacteria can be actively growing or in the stationary phase. In one aspect, administration of an antimicrobial compound is topical administration. In another aspect, administration of an antimicrobial compound is systemic administration such as oral administration. In other embodiments surfaces or substrates may be treated with the compounds of the invention for reduction or inhibition of bacterial contamination such as food surfaces, packaging, or equipment, primarily related to meat and poultry products or production.

The bacteria causing the infection can be Gram-negative, Gram-positive, or bacteria that are neither Gram-negative nor Gram-positive. Gram-negative bacteria include *Escherichia coli, Pseudomonas aeruginosa, Candidatus liberibacter, Agrobacterium tumefaciens, Branhamella catarrhalis, Citrobacter diversus, Enterobacter aerogenes, Klebsiella pneumoniae, Proteus mirabilis, Salmonella* typhimurium, Neisseria meningitidis, Serratia marcescens, Shigella sonnei, Shigella boydii, Neisseria gonorrhoeae, Acinetobacter baumannii, *Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Vibrio cholera, Shigella boydii, Morganella morganii, Edwardsiella tarda, Campylobacter jejuni, Campylobacter coli* and *Haemophilus influenzae*. In another embodiment, the bacteria are Gram-positive bacteria. Gram-positive bacteria include species of *Bacillus, Listeria, Staphylococcus, Streptococcus, Enterococcus, Corynebacterium, Propionibacterium* and *Clostridium*. Specific Gram-positive bacteria include *Staphylococcus aureus, Staphylococcus epidermidis, Enterococcus faecium, Enterococcus faecalis, Streptococcus pyogenes, Bacillus anthraces* and *Bacillus cereus*. In a specific embodiment, the bacteria are one or more drug resistant bacteria. Bacteria that are neither Gram-negative nor Gram-positive include *Borrelia burgdorferi, Mycobacterium leprae, Mycobacterium tuberculosis* and other Mycobacteria. Further included are bacteria such as Chlamydia and Mycoplasma that do not have a cell wall. In certain aspects, the bacteria are resistant bacteria such as carbapenam-resistant bacteria, methicillin-resistant *Staphylococcus aureus*, vanccomycin-resistant Enterococci or multi-drug resistant *Neisseria gonorrhoeae*.

In another aspect, a method of inhibiting bacterial growth comprises contacting the bacteria with an antimicrobial compound as described herein. The bacteria can be actively growing or in the stationary phase. Methods of inhibiting bacteria include methods useful for treatment of a subject (human or veterinary) and also include methods useful for inhibiting bacteria outside of a subject, such as use for sterilization and disinfection.

In one embodiment, the bacteria are in the form of a biofilm. A biofilm is a complex aggregate of microorganisms such as bacteria, wherein the cells adhere to each other on a surface. The cells in biofilms are physiologically distinct from planktonic cells of the same organism, which are single cells that can float or swim in liquid medium. Biofilms are involved in, for example, urinary tract infections, middle ear infections, dental plaques, gingivitis, coatings of contact lenses, cystic fibrosis, and infections of joint prostheses and heart valves.

The antimicrobial compounds and compositions may be administered prophylactically, chronically, or acutely. For example, such compounds may be administered prophylactically to animal subjects known to be prone to bacterial infections, or who are known to have been exposed to potentially infectious agents.

Since the antimicrobial compounds are antibacterially active and inhibit bacterial growth, they are also of use in treating bacterial contamination of a substrate, such as hospital instruments or work surfaces. In order to treat a contaminated substrate, the compounds may be applied to the site of such contamination in an amount sufficient to inhibit bacterial growth.

In certain embodiments, the compounds are administered to an animal subject. A "subject", used equivalently herein, means mammals and non-mammals. "Mammals" means a member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The phrase "effective amount," as used herein, means an amount of an agent, which is sufficient enough to significantly and positively modify symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The phrase "inhibitory amount", as used herein, means an amount of an agent (a compound or composition), which is sufficient to reduce the level or activity of bacterial infection to a statistically significant lesser value as compared to when the agent is not present.

The amount of compound effective for any indicated condition will, of course, vary with the individual subject being treated and is ultimately at the discretion of the medical or veterinary practitioner. The factors to be considered include the condition being treated, the route of administration, the nature of the formulation, the subject's body weight, surface area, age and general condition, and the particular compound to be administered. In general, a suitable effective dose is in the range of about 0.1 to about 500 mg/kg body weight per day, preferably in the range of about 5 to about 350 mg/kg per day. The total daily dose may be given as a single dose, multiple doses, e. g., two to six times per day, or by intravenous infusion for a selected duration. Dosages above or below the range cited above may be administered to the individual patient if desired and necessary.

The compounds may be combined in an embodiment with a carrier, which can be a pharmaceutically acceptable excipient and/or diluent appropriate for the process in which it will be used. Where administered to an animal, it will be non-toxic to the animal. The carrier, excipient and/or diluent is provided to provide improved properties of the composition, such as standardizing, preserving and stabilizing, allowing the bacteria or component to survived the digestive system of an animal, lubrication, and improve delivery. There are a myriad of such agents available which may be added. Without intending to be limiting, examples include wetting agents and lubricating agents, preservative agents, lipids, stabilizers, solubilizers and emulsifiers Also included herein are pharmaceutical compositions comprising the antimicrobial compounds. As used herein, "pharmaceutical composition" means a therapeutically effective amount of the compound together with a pharmaceutically acceptable excipient, such as a diluent, preservative, solubilizer, emulsifier, adjuvant, and the like. As used herein "pharmaceutically acceptable excipients" are well known to those skilled in the art. In one aspect, a pharmaceutical composition is suitable for topical administration. In another aspect, a pharmaceutical composition is suitable for systemic administration.

Tablets and capsules for oral administration may be in unit dose form, and may contain excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations that may be used for the drug are conventional formulations well known in the art. Topical administration includes transdermal formulations such as patches.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anaesthetic, preservative and buffering agents can be dissolved in the vehicle.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

The antimicrobial compounds may also be administered in combination with an additional active agent, such as, for example, an inhibitor of bacterial efflux. Efflux pumps are proteins that unidirectionally remove antibiotics from cytoplasmic compartments, and are considered to be a mechanism of antibacterial resistance. Bacterial efflux inhibitors include chalcone compounds as disclosed in WO 11/075136, the polybasic compounds disclosed in WO 10/054102, the quaternary alkyl ammonium functional compounds disclosed in WO 08/141012, the compounds disclosed in WO 05/007162, the substituted polyamines of WO 04/062674, which are incorporated herein by reference in their entirety.

In another embodiment, the antimicrobial compounds of Formula I can be administered with a second antibiotic. Exemplary second antibiotics include, for example, glycopeptides (e.g, vancomycin or teicoplanin); penicillins, such as amdinocillin, ampicillin, amoxicillin, azlocillin, bacampicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin; cephalosporins, such as cefadroxil, cefazolin, cephalexin, cephalothin, cephapirin, cephradine, cefaclor, cefamandole, cefonicid, ceforanide, cefoxitin, and cefuroxime, cefoperazone, cefotaxime, cefotetan, ceftazidime, ceftizoxime, ceftriaxone, and moxalactam; carbapenems such as imipenem; monobactams such as aztreonam; tetracyclines such as demeclocycline, tigilcycline, doxycycline, methacycline, minocycline, and oxytetracycline; aminoglycosides such as amikacin, gentamicin, kanamycin, neomycin, netilmicin, paromomycin, spectinomycin, streptomycin, and tobramycin; polymyxins such as colistin, colistimathate, and polymyxin B, and erythromycins and lincomycins and also sulfonamides such as sulfacytine, sulfadiazine, sulfisoxazole, sulfamethoxazole, sulfamethizole, and sulfapyridine; trimethoprim, quinolones, novobiocin, pyrimethamine, rifampin, quinolines, fluoroquinolines; and combinations thereof.

In another embodiment the compounds of the invention may be applied through a film, which in certain embodiments may be a biofilm or edible film. A film includes coatings or layers of compositions placed adjacent a surface. An edible film is a thin layer acting as a barrier between food and its surrounding environment. This layer can also be consumed with the food since it is edible. These coatings and films are designed to prolong the quality and shelf life of food by protecting it from physical, mechanical or biological damage (Janjarasskul T., Krochta J. M. 2010, Edible Packaging materials. Annu Rev Food Sci Technol. Vol. 1, pp. 415-448). Such films are well known to one skilled in the art and options and methods of producing such films will vary depending upon the particular application (see, for example, Nitin et al WO2015084938; Krochta et al U.S. Pat. No. 5,543,164). An example of an edible film is the sausage casing, which is not removed during cooking or eating. General functions of edible coatings and films in food processing are for: enhancing quarantined treatments, improving the appearance of the food, incorporation of flavors and pigments, reduction in loss of flavors and aromas, reduction in gas diffusion and reduction in water loss (Krochta, J. M., 2002. Proteins as raw materials for films and coatings: Definitions, current status and opportunities in Protein-Based Films and Coatings. Boca Raton, Fla.: CRC Press, pp. 672).

Edible films and coatings can either be prepared from lipids, polysaccharides or proteins, or from a combination of them (Dangaran, K. L. and J. M. Krochta. 2008. Whey protein films and coatings. In Whey Processing, Functionality and Health Benefits. C. Onwulata and P. Huth (eds.) Blackwell Publishing, Ames, Iowa). Some of the polysaccharides that are suitable for use as edible films and coatings include chitosan, starches, pectin, alginates and cellulose derivatives (Mohammed A. 2010, Chitosam application for active bio-based films production and potential in the food industry: Review. Food Science and Technology, Vol. 43, Issue. 6, pp. 837-842). Typically they have good oxygen but poor moisture barrier properties due to their hydrophilic nature and the ability to form strong hydrogen bonding that can be used to cross-link with functional additives such as flavors, colors, and micronutrients. Animal and vegetable fats used to make films and coatings are compounds such as fatty acids, acylglycerols, and waxes. These lipid compounds are quite suitable because they are excellent barriers to moisture and they add extra gloss to confectionary products. Waxes are mainly utilized as coatings on fruits and vegetables to reduce loss of moisture and retard respiration (Valérie M., Frédéric D., Geneviève B., Martine C., Andrée V., 2010, Factors Affecting the Moisture Permeability of Lipid-Based Edible Films: A Review. Critical Reviews in Food Science and Nutrition. Vol. 42, Issue. 1, pp. 67-89). Apart from the preservation factor, these films and coatings also facilitate the incorporation of food additives into the food to enhance the texture, flavor and color (Cagri A., Ustunol, Z., Ryser, E., 2004. Antimicrobial edible films and coatings. Journal of Food Protection Vol. 67. pp. 833-848). Protein based films are also hydrophilic and have good mechanical strength and can be used for the individual packaging of small portions of food, such as beans, nuts and cashew nuts. Moreover, they serve as functional carriers for antimicrobial and antioxidant agents (Thawien W., 2012, Protein-Based Edible Films: Characteristics and Improvement of Properties. Agricultural and Biological Sciences, "Structure and Function of Food Engineering, Chapter 3." ISBN: 978-953-51-0695-1).

The use of edible coatings and films continues to expand due to their justification by research findings in the field of active packaging. One of these active packaging applications is the incorporation of antimicrobial agents into or on edible films that can be used to successfully inhibit spoilage and pathogenic organisms from infiltrating food products. Examples of antimicrobial agents include essential oils and plants extracts, enzymes, chitosan, bacteriocins, nanoparticles and small molecule drugs (Suet-Yen S., Lee T. S., Tiam-Ting T., Soo-Tueen B., Rahmat A R., Rahman W. A. W. A., Ann-Chen T., Vikhraman M., 2013, Antimicrobial agents for food packaging applications. Trends in Food Science & Technology Vol. 33, pp. 110-123). However, there are still some challenges in the application of films and coatings. For example, environmental factors such as temperature and humidity that cannot be completely controlled during transportation and storage tend to make hydrophilic films more permeable (Pascall M. A., Lin S. J., 2013. The Application of Edible Polymeric Films and Coating in the Food Industry. Journal of Food Processing & Technology. Vol. 71, pp. 95-101).

In a preferred embodiment the invention includes an edible film incorporated with small molecules to inhibit the growth of *Campylobacter jejuni* and *Campylobacter coli* in raw chicken & poultry products. An ideal film should have some characteristics such as good oxygen barrier property to prevent the growth of aerobic bacteria, good MIC value of small molecules when incorporated in the film, good mechanical property to wrap the poultry products as well as non-toxic, unflavored and colorless.

Types of Edible Film Material

Generally the main components of daily-consumed foods, such as proteins, carbohydrates and lipids can meet the requirements for the preparation of edible films. As a rule of thumb, lipids are used to reduce water transmission, since lipids have good moisture barrier. However, they have low mechanical properties due to their hydrophobic structure and their inability to form cross linkages. Polysaccharides are used to control oxygen and other gas transmission, because they are hydrophilic and provide strong hydrogen bonding that can be used to cross-link with functional additives such as flavors, colors, and micronutrients. Protein films, on the other hand, have good mechanical stability so that when applied to fruits, they help to reduce injuries during transportation. These materials can be utilized individually or as mixed composite blends to form films. The main types of edible films include alginate, carrageenan, cellulose and it derivatives, dextrin, pectin and starch are examples of polysaccharide films. Protein films can be made from various sources, such as corn, milk, soy, wheat and whey. Lipid based films such as waxes, glycerol esters, and resins are the oldest known edible film components, however, they are less widely used currently due to their susceptibility to oxidation and low mechanical strength.

Protein-Based Edible Film/Coating.

Protein-based edible films have triggered interest in recent years because of their advantages, including the use of edible packaging materials for individual packaging of small portions of food, such as beans and nuts. In addition, they can be applied between heterogeneous food at the interfaces between different layers of components to prevent the transfer of inter-component moisture and solute migration in pizzas, pies and candies, for example (Bryne Mubururu, Dinga N. Moyo, Perkins Muredzi. Production of Artificial Sausage Casings from Whey Proteins. International Journal of Nutrition and Food Sciences. Special Issue: Optimizing Quality and Food Process Assessment. Vol. 3, No. 6-1, 2014, pp. 30-38). Besides, they can also function as carriers for antimicrobial and antioxidant agents.

In its natural state, protein films can be divided into two groups, fibrous protein films and globular protein films (Thawien, 2012). Fibrous protein chains are water insoluble, fully extended, and associated closely with each other in parallel structures via hydrogen bonding to form fibers. Globular proteins are soluble in water or acid based solutions. They fold into complicated spherical structures held together by a combination of hydrogen, ionic, hydrophobic and covalent bonds. With regard to fibrous proteins, collagen has received the most attention as a protein-based film, while for globular proteins; examples are corn zein and whey protein.

Collagen

Collagen is the main protein of connective tissue such as bone, hide, tendons cartilage and ligaments. Due to its biological properties and ready availability, which is unique among those of natural polymers, type I collagen is widely used as a biomaterial (Sisken B. F, Zwick M., Hyde J. F., Cotrill C. M., 1993, Maturation of the central nervous system: comparison of equine and other species. Equine Veterinary, Vol. 25, Issue. 14, pp. 2042-3306). It is the most commercially successful edible protein film due to its biocompatible and non-toxic characteristics, and its structural, physical, chemical and immunological properties. It can be produced into a variety of forms, and can be easily isolated and purified in large quantities (Hood E. E., Shen Q. X., Varner J. E., 1988, A developmentally regulated hydroxyproline-rich glycoprotein in maize pericarp cell walls. Plant Physiology, Vol. 1, pp. 138-142).

Corn Zein

Corn Zein is the major protein in corn. Due to its high content of non-polar amino acids, it is hydrophobic and is thermoplastic in nature (Shukla R., Cheryan M., 2001, Zein: The industrial protein from corn. Industrial Crops and Products, Vol. 13, Issue. 3, pp. 171-192). Corn zein has excellent film-forming properties and can be used for the fabrication of biodegradable films. The formation of corn zein films is facilitated by the development of hydrophobic, hydrogen and limited disulfide bonds between zein chains in the film matrix (Gennadios A., Hanna M. A., Kurth L. B., 1997, Applications of edible coatings on meats, poultry and seafoods: a review. Food Science and Technology, Vol. 30, Issue. 4, pp. 337-350), this however, results in the formation of brittle films that require the addition of plasticizers to enhance its flexibility. Its hydrophobicity characteristic enables good water vapor barrier property when compared to other edible films. It also shows the ability to reduce moisture and loss of firmness and delay color change in fresh fruit (Guilbert S., Gontard N., Cup B., 1986, Technology and application of edible protective films. Packaging Technology and Science. Vol. 8, Issue. 6, pp. 339-346).

Whey Protein

Whey protein is a nutritional and highly functional protein. It is formed through the use of transglutaminase as a crosslinking agent (Mahmoud, R., Savello, P. A. 1993, Solubility and hydrolyzability of films produced by transglutaminase catalytic crosslinking of whey protein. J. Dairy Sci. Vol. 76, Issue. 1, pp. 2935), and is shown to produce a transparent, bland, flexible, water-based edible film with excellent oxygen, aroma and oil barrier properties at low relative humidity (Miller K. S., Krochta J. M., 1997, Oxygen and aroma barrier properties of edible films: A review. Trends in Food Science & Tech. Vol. 8, Issue. 7, pp. 228-237). The most beneficial characteristic of whey protein edible films is their edibility and inherent biodegradability (Krochta, J. M., 2002. Proteins as raw materials for films and coatings: Definitions, current status and opportunities in Protein-Based Films and Coatings. Boca Raton, Fla.: CRC Press, pp. 672), especially the latter feature, which is attractive to the food industry because it reduces the bio-burden on the environment. However, to be of use in food packaging, the shelf life of the edible film should be longer than the shelf life of the packaged product (Krochta, J. M., De Mulder-Johnston, C. D., 1997, Edible and biodegradable polymer films: Challenges and opportunities. *Food Technol*, Vol. 51, pp. 61-74).

Polysaccharide-Based Edible Film/Coating

Polysaccharide films are made from starch, alginate, cellulose ethers, chitosan, carrageenan, or pectin. The great diversity of structural characteristics of polysaccharides is exhibited differences in its monosaccharide composition, linkage types and patterns, chain shapes and degree of polymerization, which influences hardness, crispiness, compactness, thickening quality, viscosity, adhesiveness, and gel forming ability. Typically, polysaccharide-based edible films have excellent gas permeability properties due to the hydrogen bonds formation between two hydrophilic subunits, thus enhancing the shelf life of the product without creating anaerobic conditions (Baldwin et al., 1995). They could also be used to extend the shelf life of muscle foods by preventing dehydration, oxidative rancidity, and surface browning. However, the hydrogen-bonding characteristic makes them poor barriers for water vapor.

Starch

Starch, is composed of amylose and amylopectin and is primarily derived from cereal grains such as corn, wheat, potato tapioca, and rice. Starch is typically found as granules, which contain millions of amylopectin molecules accompanied by even larger numbers of smaller amylose molecules (Whistler R. L., Daniel J. R., 1985. Carbohydrates. In O. R. Fennema (Ed.), Food chemistry (2nd ed.) pp. 69-137). New York: Marcel Dekker. Amylose is responsible for the film forming capacity of starch (Claudia A. R. B., Bello-Perez L. A., Gacia M. A., Martino M. N., Solorza-Feria J., Zaritzky N. E., 2005, Carbohyd. Polym. Vol. 3, Issue. 2, pp. 156-161). Films with high amylose content are flexible; show low oxygen permeability, heat-sealable, oil resistant, but water-soluble. Starch-based films are odorless, tasteless, colorless, non-toxic, biologically absorbable, and resistant to the passage of oxygen (Krogars K., Heinamaki J., Karjalainen M., Rantanen J., Luukkonen P., Yliruusi J., Eur J., 2003, Development and characterization of aqueous amylose-rich maize starch dispersion for film formation. Pharm. Biopharm. Vol. 56, Issue. 2, pp. 215-221).

Carrageenan

Carrageenan is a water-soluble polymer with a linear chain of partially sulfated galactans, which plays a role in its film-forming ability. It is extracted from the cell walls of various red seaweeds (Rhodophyceae). Variations in the degree of sulfate groups present in its structure divide carrageenan into three types: kappa, iota, and lambda carrageenan.

The presence of hydroxyl and sulfate groups in the structure of carrageenan causes its hydrophilic nature. It is widely used as an agent for thickening and gelling in food and nonfood industries due to its water holding ability (Van de Velde F., Lourenço, N. D., Pinheiro H. M., Bakker M., 2002, Carrageenan: A food-grade and biocompatible support for immobilization techniques. Adv Synth Catal, No. 344, pp. 815-835). Besides, kappa carageenans have the ability to form thermoreversible gels. However, in the presence of a small amount of acid, this characteristic will be disrupted due to cross-link formation as a result of the presence of extra positive ions (Park et al., 2001).

Cellulose Derivatives

Cellulose derivatives are polysaccharides composed of linear chains of beta-1,4 glucosidic units with methyl, hydroxypropyl or carboxyl substituents. Generally, there are four cellulose derivative forms used for edible films formation: Hydroxy Propyl Cellulose (E463; HPC), Hydroxy Propyl Methyl Cellulose (E464; HPMC), Carboxy Methyl Cellulose (E466; CMC), and Methyl Cellulose (E461; MC). The inherent hydrophilic nature of cellulose derivatives results in poor water vapor barriers and poor mechanical properties (Gennadios, 1997). Methods of enhancing the moisture barrier of these films would be by the incorporation of hydrophobic compounds, such as fatty acids into the cellulose ether matrix to develop a composite film (Morillon V., Debeaufort F., Blond G., Capelle M., Voilley A., 2002. Factors affecting the moisture permeability of lipid-based edible films: a review. Crit Rev Food Sci Nutr. Vol. 42, Issue. 1, pp. 67-89).

Chitin/Chitosan

Chitosan is an edible and biodegradable polymer derived from chitin by the process of deacetylation in the presence of an alkali. It is described in terms of the degree of deacetylation and average molecular weight. Chitosan has poor solubility in neutral solutions but soluble in acids such as acetic, citric and formic acids due to its cationic characteristic. It has lots of desirable properties including good oxygen and carbon dioxide permeabilities, film forming without additives, excellent mechanical properties and antimicrobial activity against bacteria, yeasts, and molds. The antimicrobial property of chitosan is based on the existence of a positive charge on the amino group and its attraction to other negatively charged polymers such as the membrane of microorganisms, cholesterol, and proteins (Muzzarelli, 1986). Besides its outstanding antimicrobial properties, chitosan also forms semi-permeable coatings, which can modify the internal atmosphere, thus delaying ripening and decreasing transpiration rates in fruits and vegetables (Sandford C., Godwin M., Hardwick P., 1989). Administrative and Compliance Costs of Taxation. Bath: Fiscal Publications.

Main Types of Lipid-based edible film/coating

Lipid compounds used as edible film consist of acetylated mono-glycerides, resins and natural wax. Among these compounds, paraffin wax and beeswax are most effective. The hydrophobic characteristic of lipid compounds provides excellent moisture barrier properties, however, due to their poor mechanical properties; they are usually combined with other film forming agents like proteins or cellulose derivatives (Debeaufort, F., Voilley, A., Meares, P., 1994. Water vapor permeability and diffusivity through methylcellulose edible films. J. Membr. Sci. No. 91, pp. 125-133).

Waxes and Paraffin

Waxes have been used to retard desiccation of citrus fruits in China since the twelfth and thirteenth centuries. The Chinese noted that the waxes slowed water loss and caused fermentation (Hardenburg R. E. 1967. "Wax and Related Coatings for Horticultural Products. A Bibliography." Agr. Res. Bull. 15-51, Washington, D.C.: U.S. Dept. of Agric.). Paraffin wax is derived from the distillate fraction of crude petroleum and consists of a mixture of solid hydrocarbon resulting from ethylene catalytic polymerization. It contains predominantly straight-chain hydrocarbons with an average chain length of 20 to 30 carbon atoms. Due to its characteristics such as non-reactive, non-toxic, good moisture barrier and colorless, it is permitted for use on raw fruits, vegetables and cheese since the 1930s (Kaplan H. J. 1986. Washing, waxing, and color adding. In: Wardowdki W F, Nagy S, Grierson W, editors. Fresh citrus fruit. Westport, Conn.: AVI Publishing Co. 379 p). These coatings are the most efficient edible compounds blocking transport of moisture, reducing surface abrasion during handling of fruits and controlling soft scald formation in apples (Kester J. J., Fennema O. R., 1986. Edible films and coatings: a review. Food Technol Vol. 40, Issue. 12, pp. 47-59).

Acetylated Glycerol Monostearate

Acetylation of glycerol monostearate by its reaction with acetic anhydride yields1-stearodiacetin. It is an emulsifier in which acetic acid is bound with monoglyceride. Acetylated monoglycerides (AMG) films display the exclusive characteristic of solidifying from the melting state to a flexible, wax-like solid. Elongation of the films can be as high as 800%, while most lipids in the solid state can be stretched to only 102%. The films are mainly used for poultry and meat cuts to retard moisture loss during storage (Bourtoom T., 2008. Edible films and coatings: characteristics and properties. *International Food Research Journal*, Vol. 15, No. 3, pp. 237-248). Another application of AMG films is as an antioxidant carrier. When compared to whey protein isolate coating, an AMG coating makes some of the most effective natural antioxidants such as tocopherols migrate more freely to the surface due to the hydrophobic characteristic (Juan I. M., John M. K., 1997. Whey Protein and Acetylated Monoglyceride Edible Coatings: Effect on the Rancidity Process of Walnuts. J. Agric. Food Chem. Vol. 45, pp. 2509-2513). However, AMG films are shown to have high oxygen permeability (Hoover M. W., Nathan, P. J., 1981. Influence of tertiary butylhydroquinone and certain other surface coatings on the formation of carbonyl compounds in granulated roasted peanuts. J. Food Sci. Vol. 47, pp. 246-248), therefore they did not provide protection against lipid oxidation in granulated roasted peanuts.

Shellac Resins

Shellac resins are secreted by the insect *Laccifer lacca*, and are composed of a complex mixture of aliphatic alicyclic hydroxyl acid polymers. It is not recognized as a "GRAS" substance by FDA and as such is only permitted as an indirect food additive and is mainly used in coatings for the pharmaceutical industry (Berg S., Bretz M., Hubbermann E. M., Schwarz K., 2012, Influence of different pectins on powder characteristics of microencapsulated antho-cyanins and their impact on drug retention of shellac coated granulate. *Journal of Food Engineering*, Vol. 108, No. 1, pp. 158-165). Shellac resins are widely used for coating citrus and other fruits to enhance their surface glossiness thus decrease the prevalence of postharvest wilting. However, citrus with shellac resin coating typically has lower internal oxygen, higher internalcarbon dioxide, and higher ethanol content (an indication of off flavor) than citrus with wax coatings due to their differences in gas permeance and ability to block openings in the skin. (Bourtoom, 2008).

Composite Edible Film/Coating

Edible films can be synthesized by blending polysaccharides, protein and lipids, which enables one to utilize the advantages of each class of film (Kester & Fennema, 1984). The combination could be proteins and carbohydrates, proteins and lipids, carbohydrates and lipids or synthetic or natural polymers. The aim is to improve the permeability or mechanical properties for specific purposes. The individual components of these composite films are blended in the form of an emulsion, suspension, or dispersion of the non-miscible constituents, or in successive layers, or in a solution in a common solvent. An example of a composite polymer widely used in food packaging is polyvinyl acetate. It is a nontoxic commercially available polymer prepared through emulsion polymerization and is incorporated with fungicides for protection of diverse foods or as a coating for pharmaceutical products (Carmona-Ribeiro A. M., Carrasco L. D., 2013, Cationic antimicrobial polymers and their assemblies. *International Journal of Molecular Sciences*, Vol. 14, No. 5, pp. 9906-9946). For more than 50 years, techniques such as spraying and dip coating and encapsulation have been used in the pharmaceutical industries to incorporate bioactive agents with polymers. For example, an anionic copolymer based on methacrylic acid and methyl methacrylates was used for coating tablets and pills. This coating was resistant to gastric juices but improved the protection of the tablets against moisture, light and oxygen under tropical conditions (Petereit H. U., Meier C., Roth E., U.S. Pat. No. 7,160,558 B2, January 2007).

In another example, composite polymer spheres with a sugar coating on the outside and edible polymer coating inside give them dual functionality to target and deliver drugs. The sugar coating provides barrier to oxygen and gives taste to the tablet, while the edible polymer serves as a mechanism for delayed release of the drug. The polymer vesicles could be used to mimic a living cell or used as drug delivery vessels, and could also be used to convey drugs and biomolecules to injured or cancerous tissues in animals or humans (Schlaad H., You L., Sigel R., 2009, Glycopolymer vesicles with an asymmetric membrane. *Chemical Communications*, No. 12, pp. 1478-1480).

The invention has been shown and described herein in what is considered to be the most practical and preferred embodiment. The applicant recognizes, however, that departures may be made therefrom within the scope of the invention and that obvious modifications will occur to a person skilled in the art. The examples which follow are intended for purposes of illustration only and are not intended to limit the scope of the invention. All references cited herein are hereby incorporated in their entirety by reference.

Example 1

This example is directed to developing the potential lead narrow spectrum small molecule inhibitors of *Campylobacter jejuni* for oral administration of chickens to control *Campylobacter* with ultimate goal of reducing human infections. This will be accomplished via the evaluation and optimization of the derivatives (TH-4 and TH-8) identified though a high throughput screen (HTS) of over 4,182 pre-enriched compounds (see below). Our long term goal is to improve food safety by reducing the transmission of *Campylobacter* to humans via the food chain, through development of specific, orally compatible, water soluble narrow spectrum small molecule inhibitors. The three aims of this experiment are:

Aim 1. Explore and improve the antibacterial activity and aqueous solubility of the lead compounds TH-4 and TH-8 through structural modification focused on SAR and lead optimization studies.

Aim 2. Assess the efficacy of TH-8 and TH-8 derivatives in vitro and determine the effect on broiler gut health and C jej uni colonization.

Aim 3. Identify target and explore mechanisms of action of most potent small molecule inhibitors.

For a discussion of the high throughput process see Kumar et al. (2016)"Novel anti-campylobacter compounds idenfied using high throughput screening of pre-selected enriched small molecules library" Frontiers in Microbiology, Vol. 7, Article 405 pp. 1-12. In our recent study, we screened a small molecule library of 4,182 compounds against highly pathogenic *C. jejuni* 81-176 strain (Wallace, I. M., M. L. Urbanus, G. M. Luciani, A. R. Burns, M. K. Han, H. Wang, K. Arora, L. E. Heisler, M. Proctor, R. P. St Onge, T. Roemer, P. J. Roy, C. L. Cummins, G. D. Bader, C. Nislow, and G. Giaever. 2011. Compound prioritization methods increase rates of chemical probe discovery in model organisms. Chemistry & biology 18:1273-1283).

TABLE 1

Assessing the anti-camylobacter activity for two re-synthesized compounds using synthetic films and pathogenic *C. jejuni* 81-176 strains.

| Films | % of compound incorporation | Diameter of zone of inhibition |
|---|---|---|
| Film with no compound | — | No inhibition |
| Film with JA-144 | 1.0 | 1.2 cm |
| Film with JA-128 | 1.0 | 2.7 cm |

Seven hundred and eighty one compounds were identified possessing bactericidal or bacteriostatic property against *C. jejuni* at 100 μM concentrations (Kumar et al 2016) (FIG. 2) (Kumar A, Drozd M, Pina-Mimbela R, Xu X, Helmy Y A, Antwi J, Fuchs J R, Nislow C, Templeton J, Blackall P J, Raj ashekara G. (2016) Novel Anti-Campylobacter Compounds Identified Using High Throughput Screening of a Pre-selected Enriched Small Molecules Library. Front Microbiol. Apr. 6; 7:405. doi: 10.3389/fmicb.2016.00405. eCollection. PMID: 27092106). Further through secondary screens we identified several compounds with narrow spectrum activity specific to *C. jejuni* and *C. coli*. We synthesized 15 derivatives of one selected hit (Compound 1) (FIG. 3) from primary streening and tested for specificity and potency against diverse foodborne pathogens like *Salmonella, E. coli, Listeria* and also several commensal and/or probiotic bacteria. Two derivatized compounds (TH-4 (1d) and TH-8 (le) found to be specific to *C. jejuni* and *C. coli* and possessed low MICs (1.2 5 μM). Both TH-4 and TH-8 lacked toxicity against the colon cells (CCD-112CoN, ATCC) (data not shown) and also displayed promising in vivo results in a chicken model (FIG. 4) when administered orally. These two compounds also retained the in effect against both *Campylobacter* species when incorporated in edible film suggesting that this compound can also be exploited for post-harvest *Campylobacter* control also (eg. in the form of meat wrapper), However, these compounds were not readiliy soluble in water and were administered to chicken in 30% DMSO. To be feasible for mass application in poultry production the compounds need to be water soluble. These two compounds will be used and subjected to further structural studies to develop them as specific narrow spectrum water soluble compounds for application for chickens. Though, beyond scope of this proposed study, we plan to develop these compounds for future application in humans also. This is expected to lead to timely development of innovative strategy to reduce *Campylobacter* in poultry, a natural host for *C. jejuni* and will significantly impact food safety there by reducing human campylobacteriosis cases.

Aim 1. Explore and Improve the Antibacterial Activity and Aqueous Solubility of the Lead Compounds TH-4 And TH-8 Through Structural Modification Focused on SAR and Lead Optimization Studies.

Figure 2:
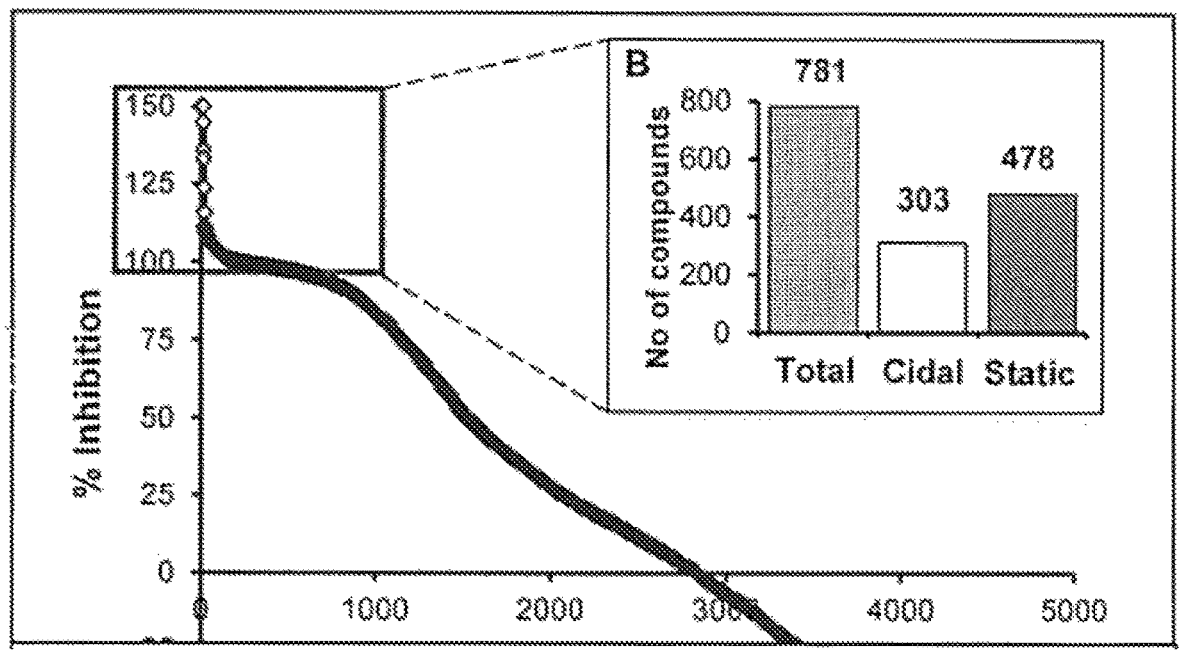
FIG. 2 are graphs showing Primary HTS of compounds for growth inhibition against *C. jejuni* 81-176 using a pre-selected library of 1,182 compounds. A cut off percentage value of ≥99.0% growth inhibition resulted in 781 hit compounds. These compounds were categorized based on their activity (see details in box labeled B).
Figure 5:
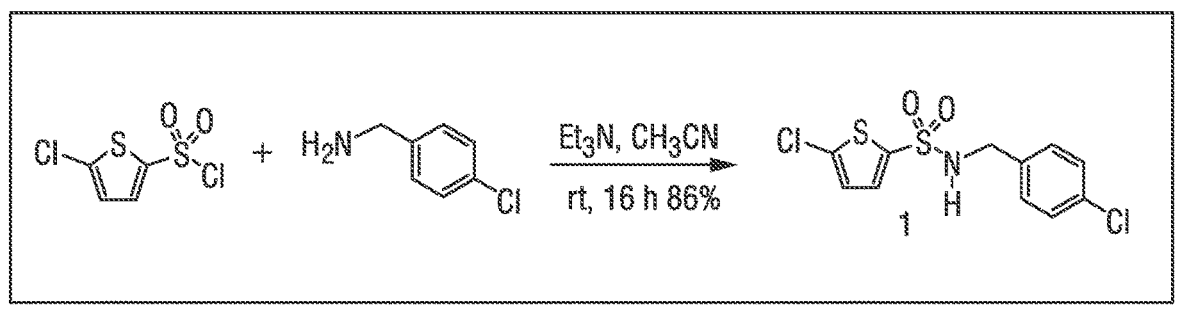
FIG. 5 is a graphic showing the process of synthesis of compound 1.

Compound 1 was identified via a screening of 4,182 compounds for growth inhibition against *C. jejuni*. This compound was re-synthesized according to FIG. 5 for validation purposes. As shown in FIG. 2, a total of 15 analogues of hit 1 were then prepared as a part of a preliminary hit-to-lead campaign to establish whether this class of compounds would display useful drug properties. Compounds TH-4 (1d) and TH-8 (1e) were shown to display the best combination of potency against the bacteria, lack of toxicity against the colon cells and promising in vivo results in a chicken model as described above and thus have been adopted as promising lead compounds for further structural study and development. The prime advantage of this structural scaffold is the ability to prepare a wide array of structurally diverse compounds in essentially a single transformation from commercially available precursors. Derivatization will focus on two key aspects: 1) expanding the structural diversity of the analogues for structure-activity relationship (SAR) studies and 2) the rational design of more water soluble analogues for translational studies. The initial SAR studies will involve the synthesis of a much larger library of compounds that target modifications of both the thiophene portion of the molecule and the benzylamine. Utilizing commercially available sulfonyl chloride derivatives number of, a thiophenes and isosteric aryl and heteroaryl rings will be explored, including those containing polar heteroatoms and functional groups. The substitution of the benzylamine, both in a steric and electronic sense, will also be addressed. Once the SAR has been established, the focus of the project will shift towards the improvement of water solubility of these agents utilizing data obtained from this library. The ACD/Labs Percepts Suite will be used to predict the relative solubility (LogD) for the compounds as well as to aid in the design of more water soluble compounds. All compounds prepared during the course of these studies will be provided to Dr. Rajashekara for biological evaluation and that data will be incorporated into subsequent ompound design, creating an iterative cycle of drug discovery and development.

Aim 2. Assess the Efficacy of TH-8 and TH-8 Derivatives in vitro and Determine the Effect on Broiler Gut Health and *C. jejuni* Colonization.

Selected derivatives will be screened in number invitro assay as described previously and in our recent paper. (n fs); 1) Minimum Inhibitory Concentration (MIC), 2) minimum bactericidal effect, 3) effect on diverse *C. jejuni* strains, 4) cytotoxicity to human intestinal cells, 5) effect on intracellular survival of *C. jejuni* in cultured intestinal cells, 6) The impact of small molecules on acquisition of resistance by *Campylobacter*.

In vivo evaluation of small molecules: We will test the applicability of the selected compounds to specifically reduce the *Campylobacter* load in broiler chickens just before slaughter. Throughout the experiment, chickens will receive the same type of commercially available crumble feed. For this, we will inoculate xx groups of 5 week old broiler chickens (n=10) free of *Campylobacter* with *C. jejuni* (lx $10^6$ cfu/chick in 200 µl of PBS). Group 1 will receive the compounds at the determined MIC level (from above): Group 2 will receive 10 times the MIC; and Group 3 will serve as untreated control. Three days following *C. jejuni* inoculation, these chickens will be given water with or without small molecule inhibitors daily for 1 week. Following treatment (at market age; ~42 days) hickens will be killed and kinetics of colonization in the cecum will be monitored by determining CFU. In addition, we will also monitor faecal shedding following small molecule administration daily until the termination of the experiment. For those compounds that exhibit significant reduction in *C. jejuni* numbers, we will repeat the experiment to confirm our findings.

In addition, other important parameters, such as average feed intake, average gain, feed conversion ratio, and mortality will be recorded. Further, we will conduct metagenomic studies on the cecal microflora from chickens treated with small compounds and compare to control untreated birds (Turnbaugh et al 2009). This will provide a more comprehensive picture on the effect of these compounds on the gut microflora Our future studies will focus on testing compounds that give the best result in our small pen trials, under near to commercial production setting.

Aim 3. Identify Target and Explore Mechanisms of Action of Most Potent Small Molecule Inhibitors.

In previous work, analysis of a EZ::TN transposon-based mutant library comprised of 7,201 individual mutants (4.48><coverage of the genome) revealed 195 essential gene candidates (Smith et la 2009 Quantitative phenotyping via deep barcode sequencing. Genome Res. 2009 October; 19(10):1836-42. doi: 10.1101/gr.093955.109. Epub 2009 Jul. 21; Smith et al 2012 Barcode sequencing for understanding drug-gene interactions. Methods Mol Biol. 2012; 910:55-69. doi: 10.1007/978-1-61779-965-5_4) We have recently developed a similar high-density universal Barcoded Transposon-sequencing approach (BarT-seq) (Smith et al 2012) that can be readily adapted to diverse *Campylobacter* species and strains. In this assay, each strain carries a precise start to stop deletion is "barcoded" with two unique 20 base pair sequences that serve as strain identifiers. These pools are grown competitively in any condition to identify genes most important for growth. In practice strains carrying deletions of these genes become depleted from the pool over time. The relative abundance of each strain is measured by the abundance of the barcodes. Specifically, following pooled cell growth, genomic DNA is extracted from cells, barcodes are PCR amplified using primers common to every strain, and relative strain abundance quantified. The advantages of our BarT-seq approach are several-fold. First, after initial construction of the mutant library (with a minimum genome coverage of SOX) containing 10-20 insertions/gene, we can unambiguously identify the location of each transposon insertion in a single deep coverage sequencing run. Once each barcode is assigned to a genomic location, subsequent genome-wide screens require only minimal sequencing to "count" each unique barcode. This allows for the sampling of the same exact transposon library in hundreds to thousands of conditions. By virtue of this throughput, we can assess the genes required for survival in diverse conditions, including but not limited to, i) wide ranges of anti-*Campylobacter* concentrations, ii) assessing a matrix of drug combinations, and iii) assessing the requirements of each gene in the presence and absence of drug in vivo in chickens over time.

In parallel to the BarT-seq approach to define the drug-gene interactions that underlie the efficacy of our novel anti *Campylobacter* agents and its derivatives, we will employ our well-established yeast HIPHOP chemogenomic assay (Lee A Y, et al. 2014. Mapping the cellular response to small molecules using chemogenomic fitness signatures. Science. Apr. 11; 344(6180):208-11. doi: 10.1126/Science. 1250217. Erratum in: Science. 2014 May 23; 344(6186):1255771). HIPHOP provides direct mechanistic insight into a gene's requirement for cell growth and viability by combining small-molecule screening with genomic target identification. Because the screens are both target and drug agnostic, one obtains the whole-cell response to perturbation. In our recent study (Lee et al., 2014), we systematically characterize the cellular response to small molecule perturbation by screening 3250 compounds using our Haploinsufficiency Profiling (HIP) and Homozygous Profiling (HOP) chemogenomic platform. HIP exploits drug-induced haploinsufficiency, a growth or fitness defect (ED observed in a heterozygous strain deleted for one copy of the drug's target. By measuring the drug-induced FDs of ~1,100 heterozygous strains representing the yeast essential genome, strains exhibiting the greatest FDs identify candidate protein targets. In the complementary HOP assay of ~4,800 homozygous deletion strains, nonessential genes required to buffer the targeted pathways can be identified. Each combined HIPHOP profile provides a genome-wide view of the cellular response to a specific compound. See FIG. 6

Data analysis and expected results. We anticipate identifying highly potent water soluble lead compounds having specific narrow spectrum effect on *C. jejuni*. Through in vivo studies, we anticipate to identify compounds having promising effect on *C. jejuni* when administered orally in water, a prerequisite in poultry production. The optimization of these lead compounds will continue throughout the course of the proposed grant and promising orally active compounds should be identified prior to the completion of the funding period, ultimately facilitating further grant applications for clinical/commercial testing. Data generated using several biological assays (both in vitro and in vivo) in this study will be analyzed using T-test or one-way ANOVA followed by the Tukey's post-test P<0.01 or 0.05 (a level) will be considered significant.

Innovation. Despite the appreciated magnitude of the food safety hazard associated with *Campylobacter*, effective and practical interventions are scarce for either pre harvest or post harvest control. Our proposed research will yield new pre harvest intervention strategy thus will have direct impact on food safety, public health, and global food policy. The planned activities utilize multidisciplinary approaches and will be conducted by a highly qualified team of investigators who have strong expertise in *Camplobacter* and food safety, medicinal chemistry and chemogenomics. Our study is innovative and takes a novel approach of identifying narrow spectrum small molecule inhibitors of *Campylobacter*. Although the amount of genomic information on both pathogens and their hosts is growing, drug remedies remain as elusive as ever. This challenge is greatest for antimicrobials, in large part because pharmaceutical companies have abandoned their efforts in this area due to its very challenging pharmaco-economics. To directly address the challenge of increasing food safety, here we will develop specific, orally bioavailable narrow spectrum small molecule inhibitors of *Campylobacter*. Because of the small size, solubility and stability under adverse environmental conditions, they are highly suitable for mass application, prerequisite in the poultry production.

Relation to Enteric CETR. Reducing *Campylobacter* infections in humans will significantly reduce the burden on the health system. Since majority of human infections are due to consumption of contaminated poultry meat and meat products, on farm control of *Campylobacter* will have significant impact on the bacterial load in the processed food which should translate to reduced human infections. It is estimated that pre-harvest reduction of *Campylobacter* by 2 logs or higher could result in up 90% reduction in human campylobacteriosis. In addition, food safety is a major challenge for the poultry industry both nationally and internationally. Ensuring safe food supply is critical for having positive influence on the consumers thereby enabling the growth of poultry industry.

Figure 6A:
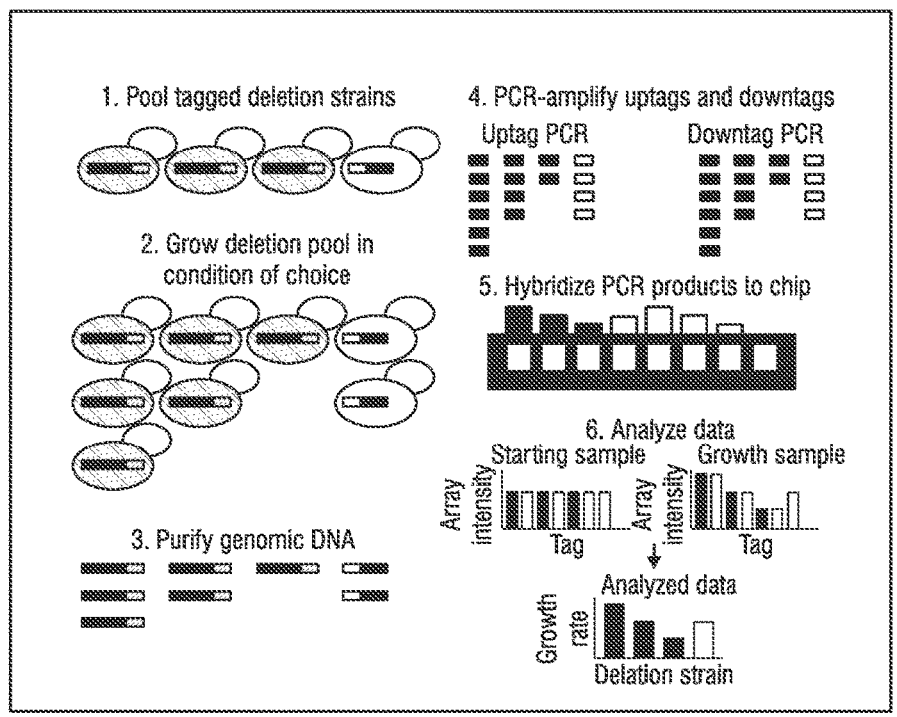
FIGS. 6A and B are graphics showing BarT sequence collections (A) and stats (B), here an example of Yeast.
Figure 6B:
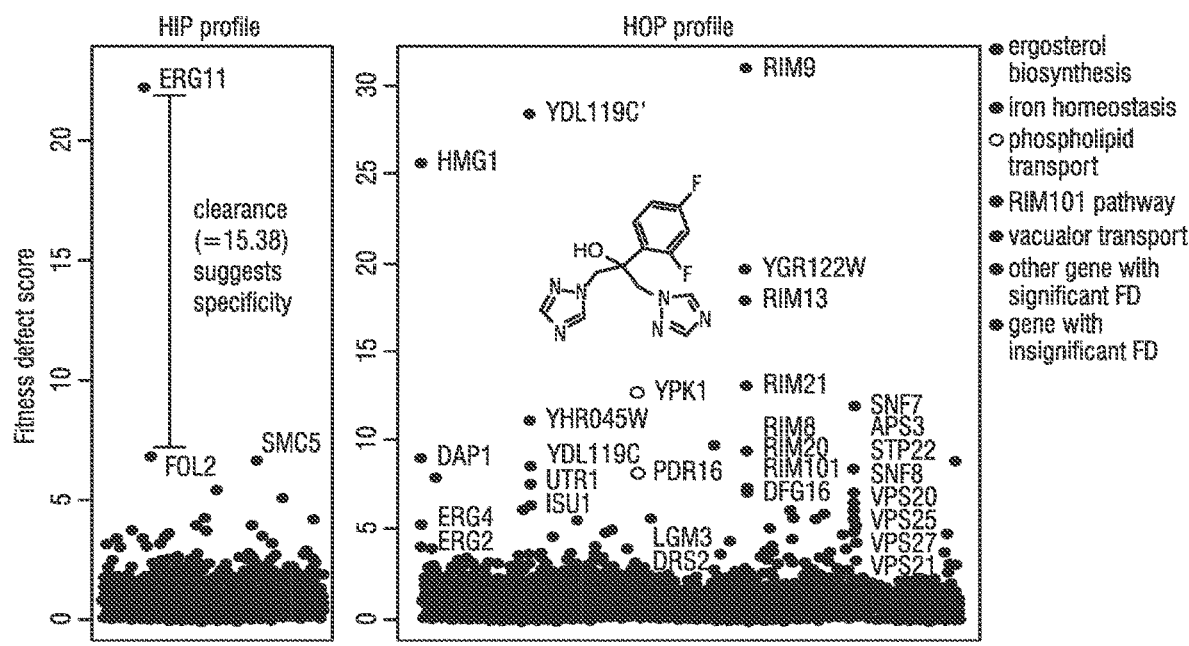
Figure 7:
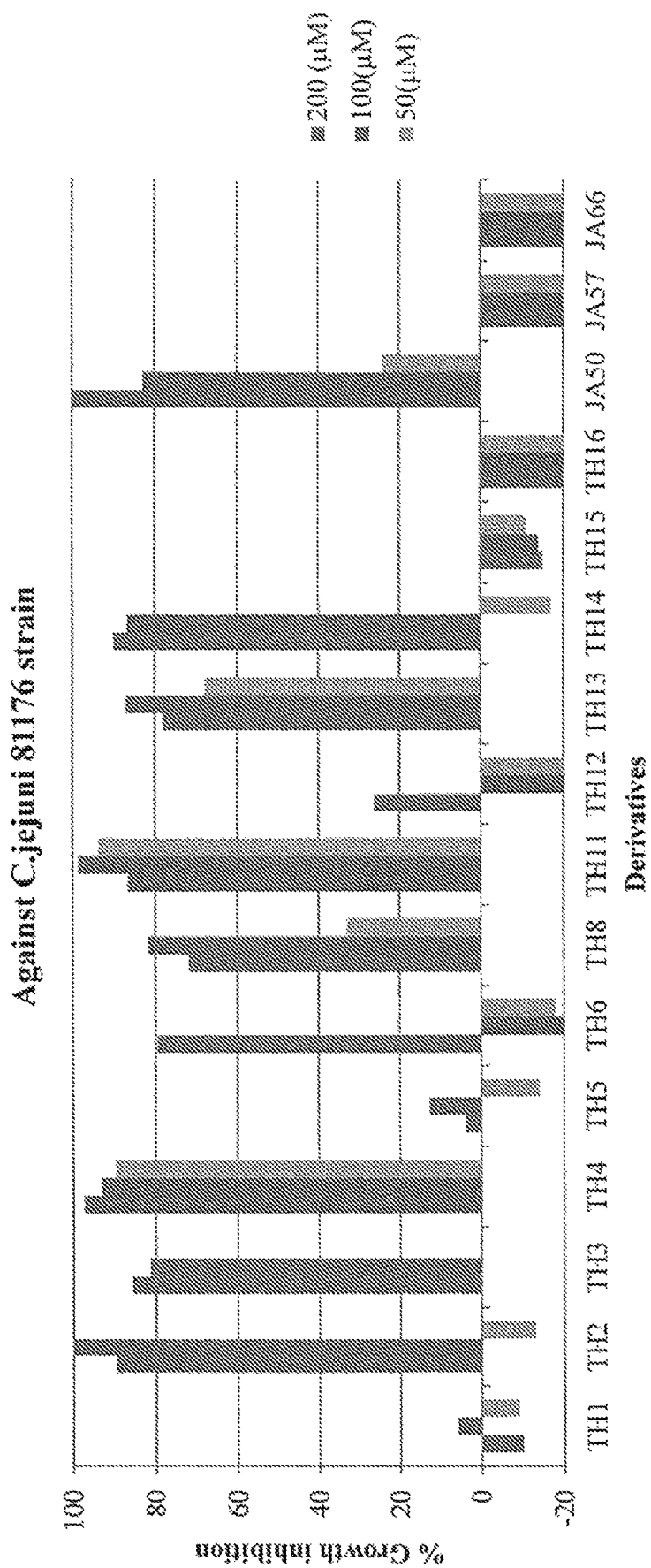
FIG. 7 is a graph showing percent growth inhibition against *C. jejuni* with 15 compounds.
Figure 8:
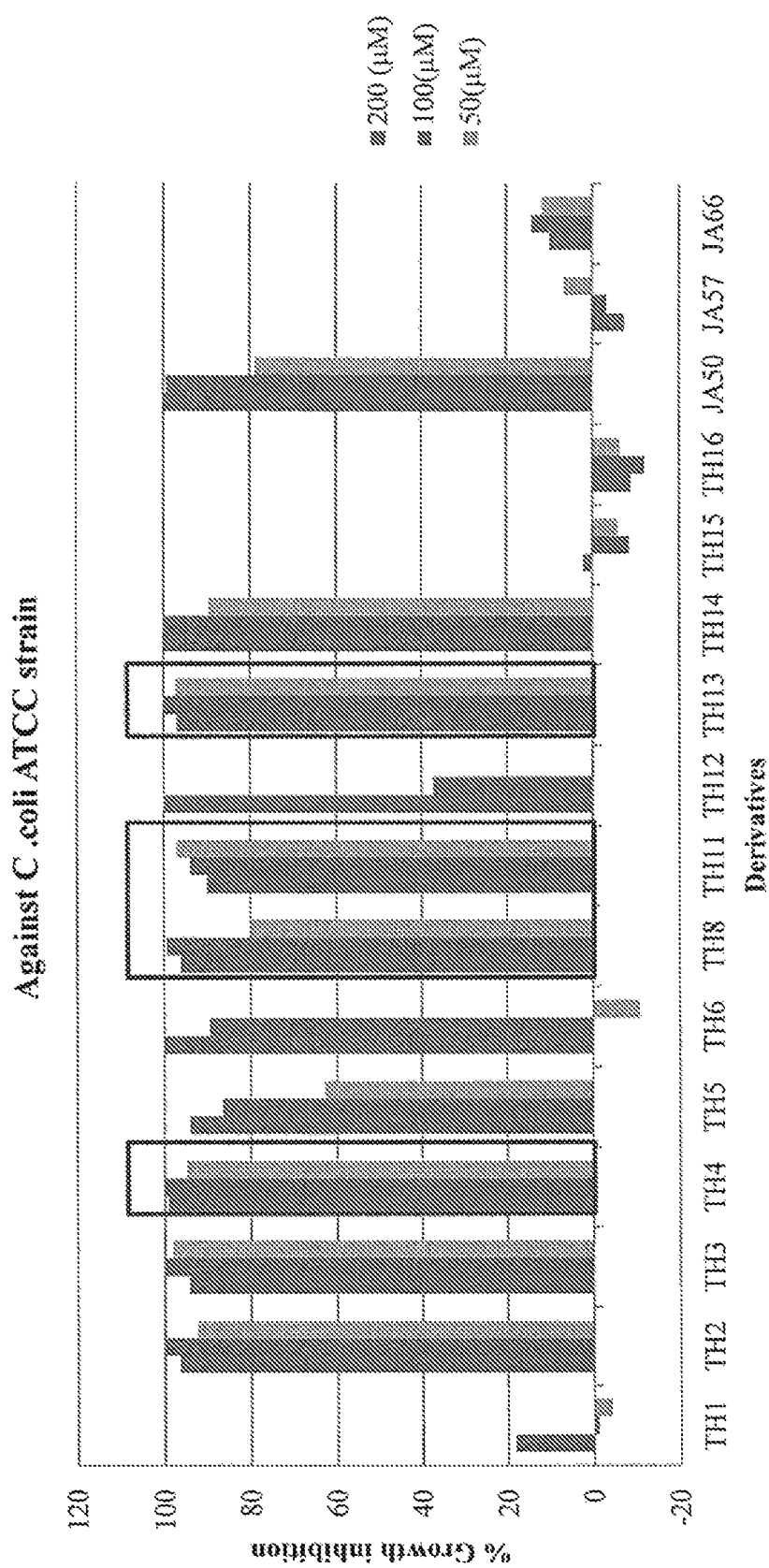
FIG. 8 is a graph showing growth inhibition against *C. coli* of 15 compounds.
Figure 9A:
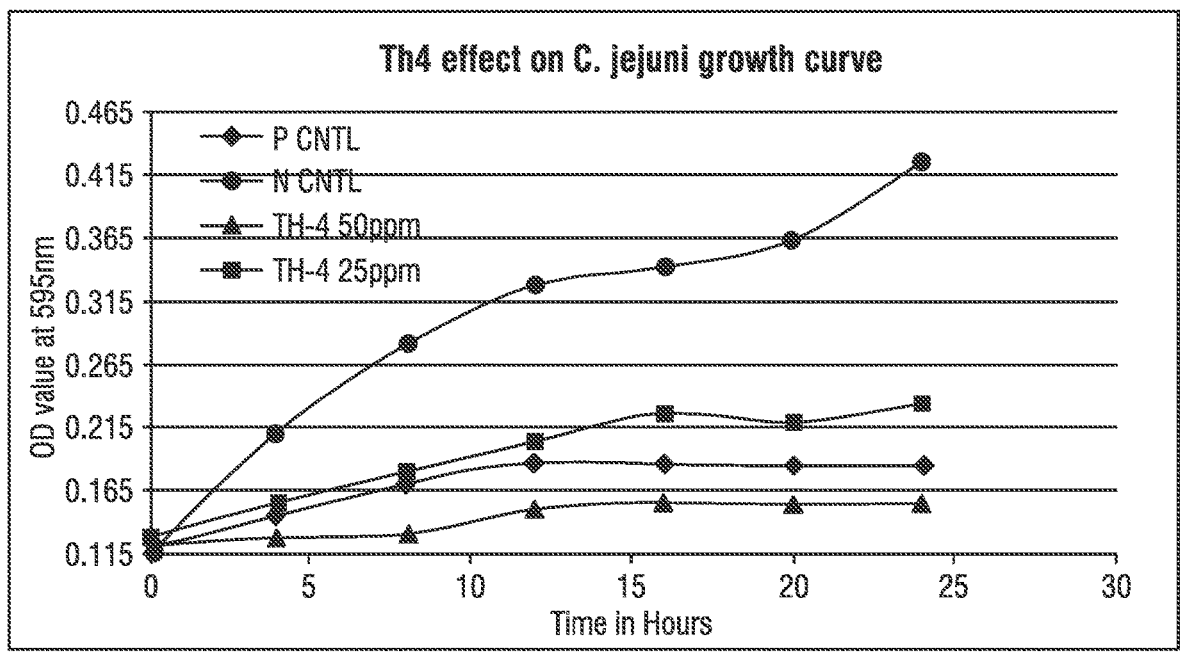
FIGS. 9A and B are graphs showing TH-4 effect (A) on *C. jejuni* growth and *C. coli* growth (B).
Figure 9B:
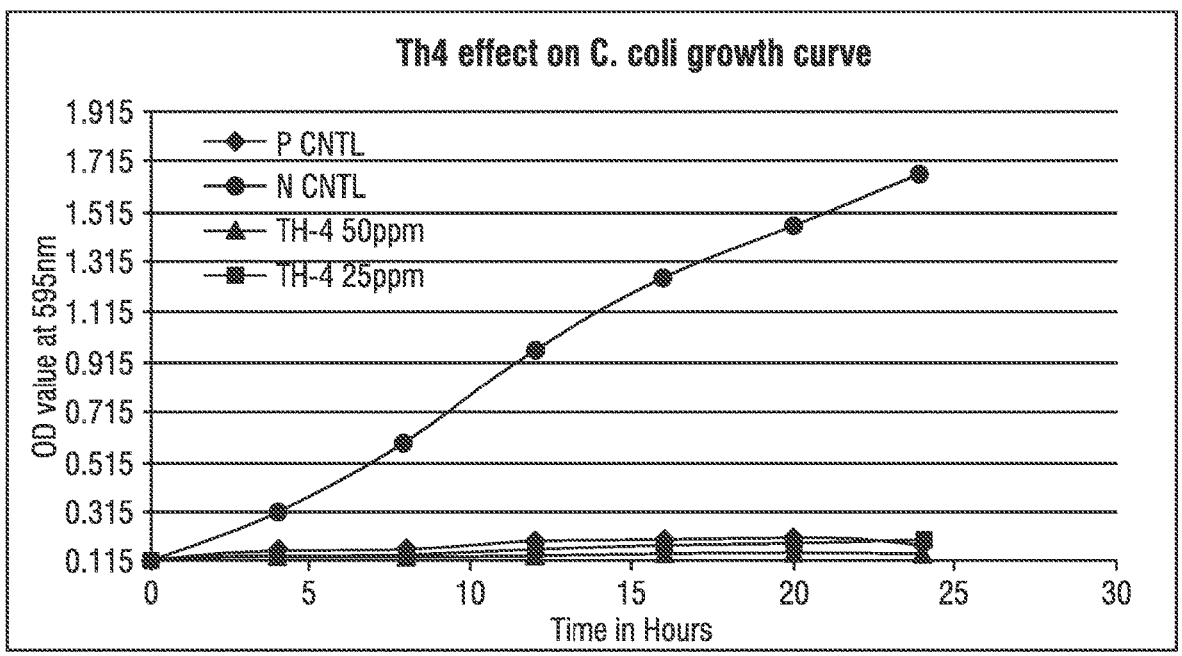
Figure 10A:
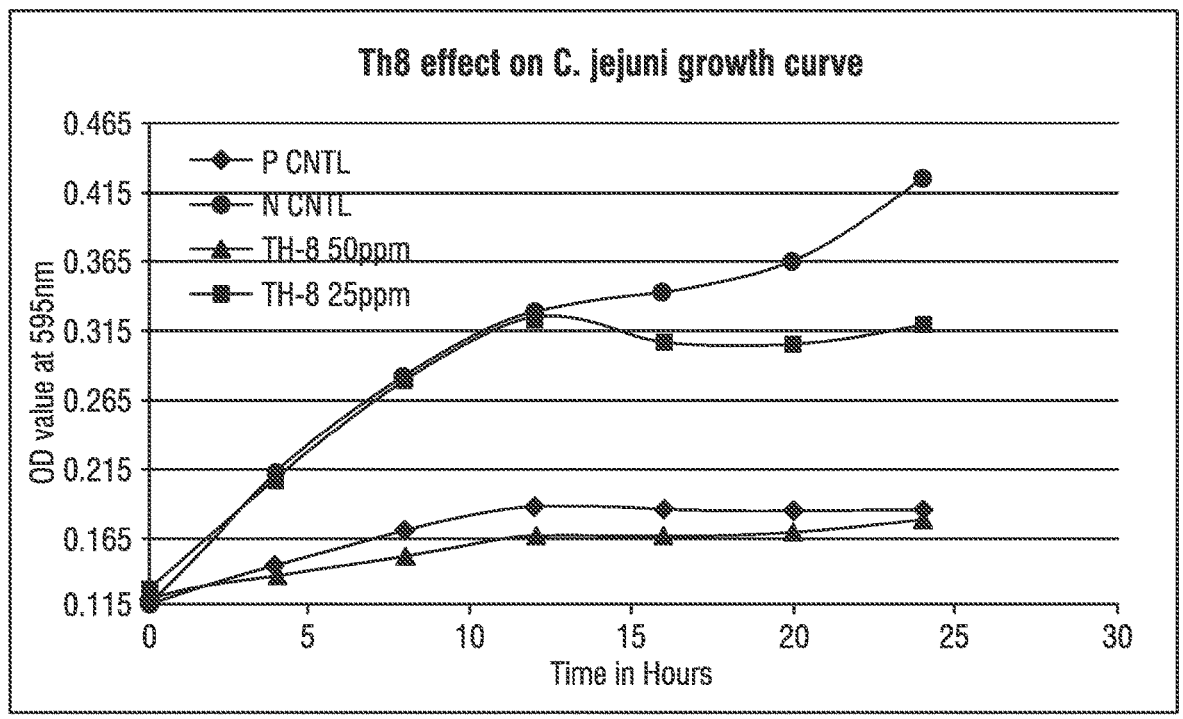
FIGS. 10A and B are graphs showing TH-8 effect on *C. jejuni* growth (A) and *C. coli* growth (B).
Figure 10B:
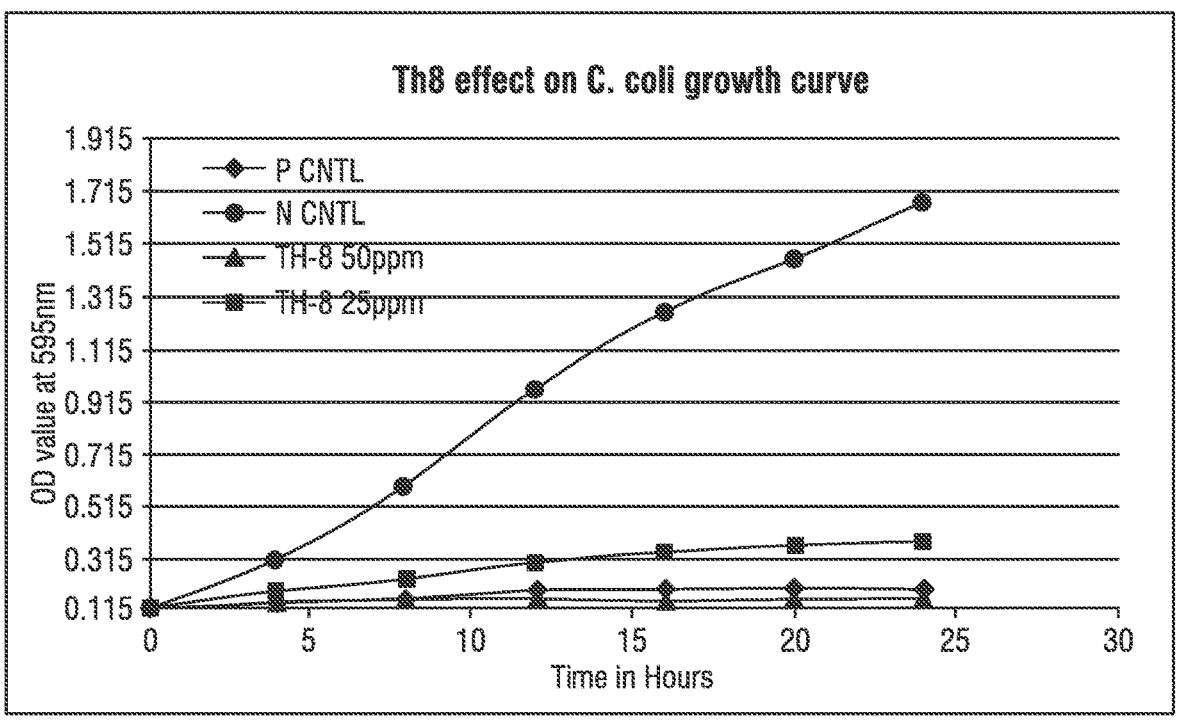
Figure 11:
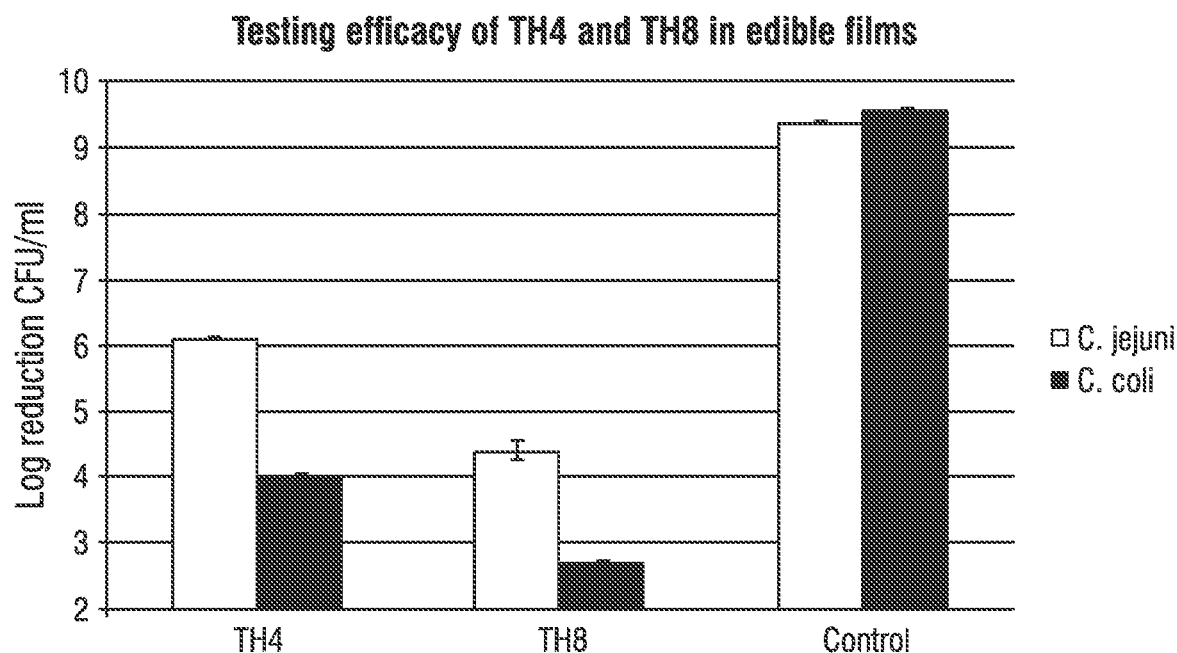
FIG. 11 is a graph showing efficacy of TH-7 and TH-8 compounds when incorporated in edible films against *C. jejuni* and *C. coli*.
Figure 12:
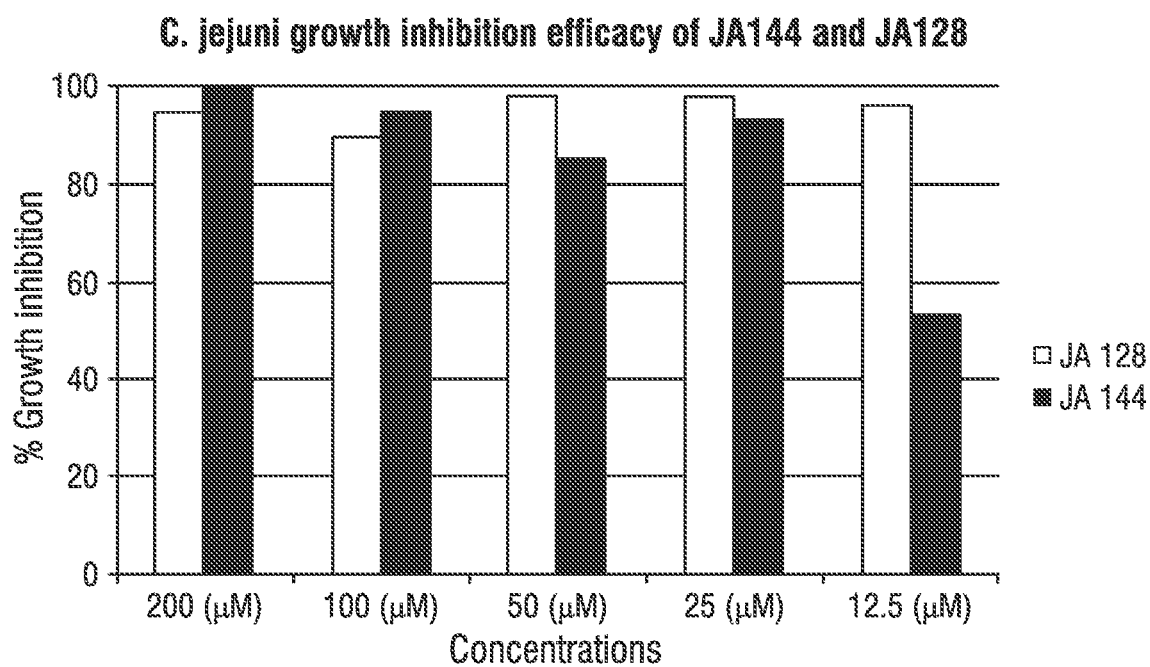
FIG. 12 is a graph showing *C. jejuni* growth inhibition by JA-144 and JA-128.
Figure 13A:
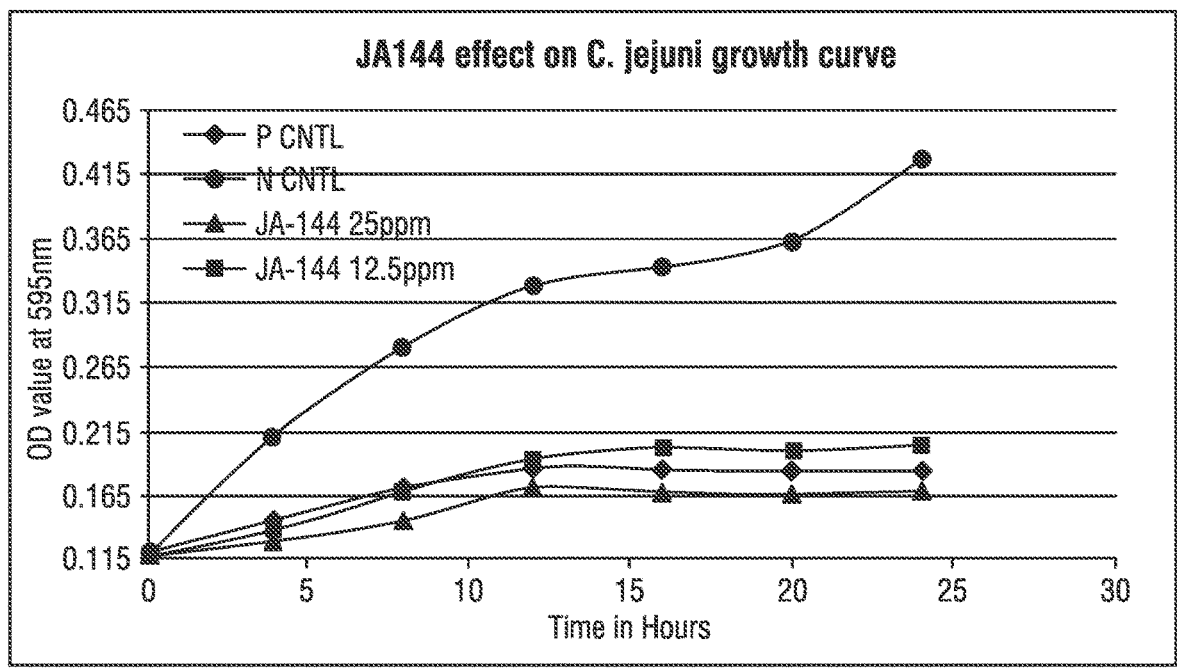
FIG. 13 are graphs showing JA-144 effect on *C. jejuni* growth (A) and *C. coli* growth (B).
Figure 13B:
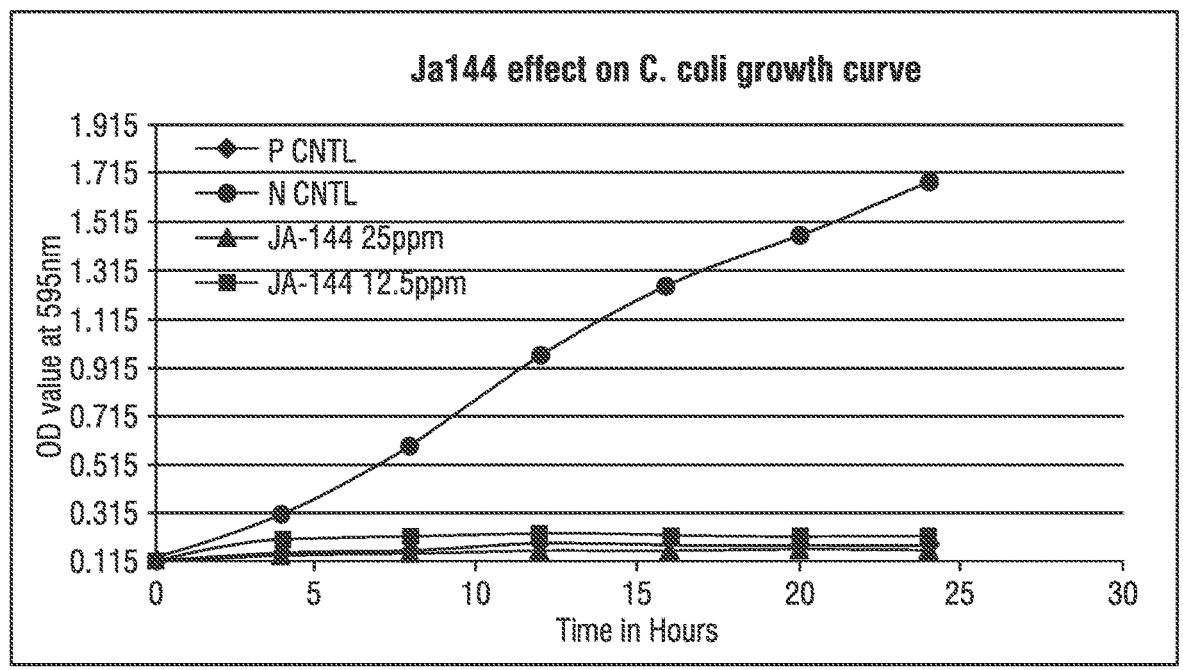
Figure 14:
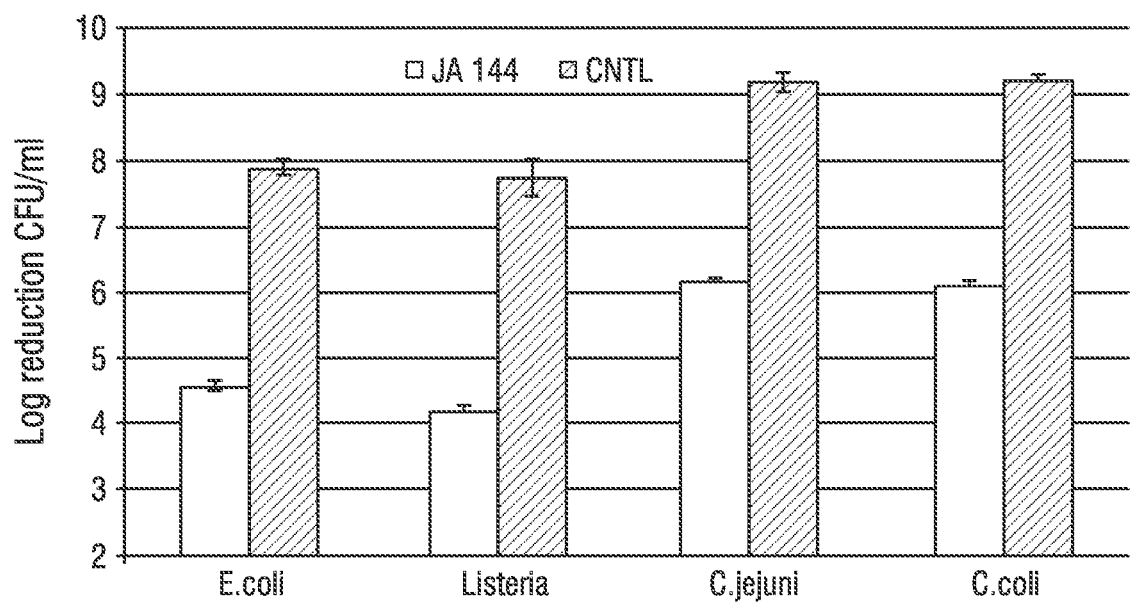
FIG. 14 is a graph showing efficacy of JA-144 when incorporated in edible films against four bacteria.
Figure 15:
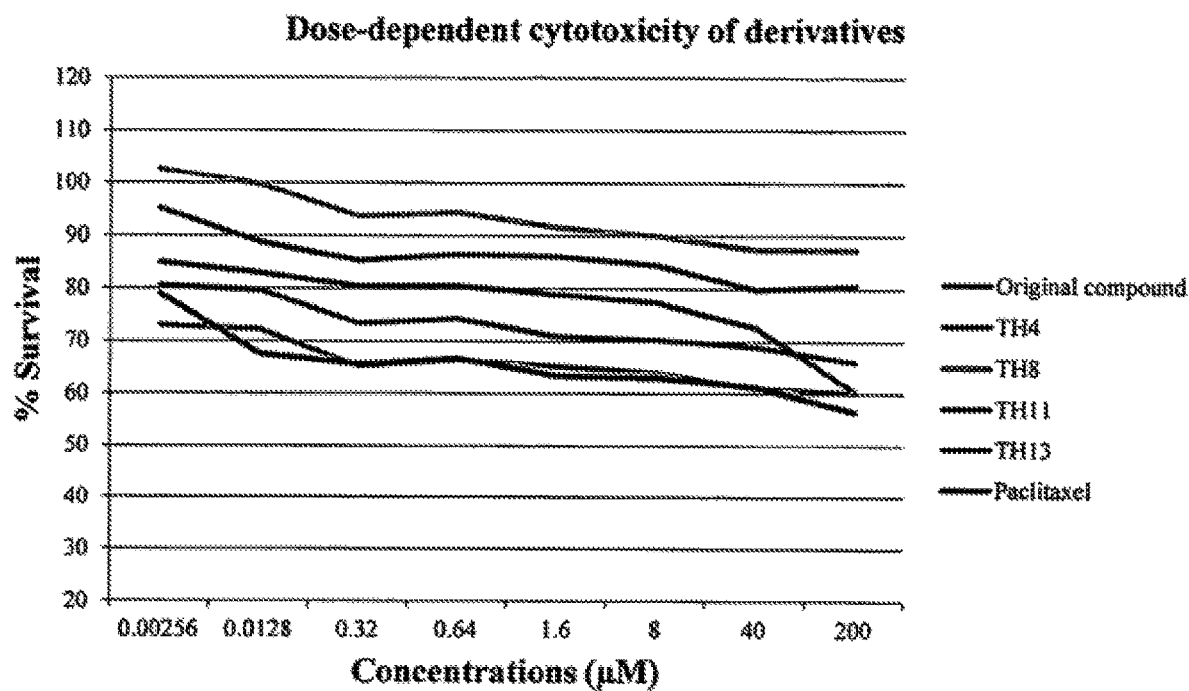
FIG. 15 is a graph showing dose-dependent cytotoxicity of compounds on normal colon cells.
Figure 16:
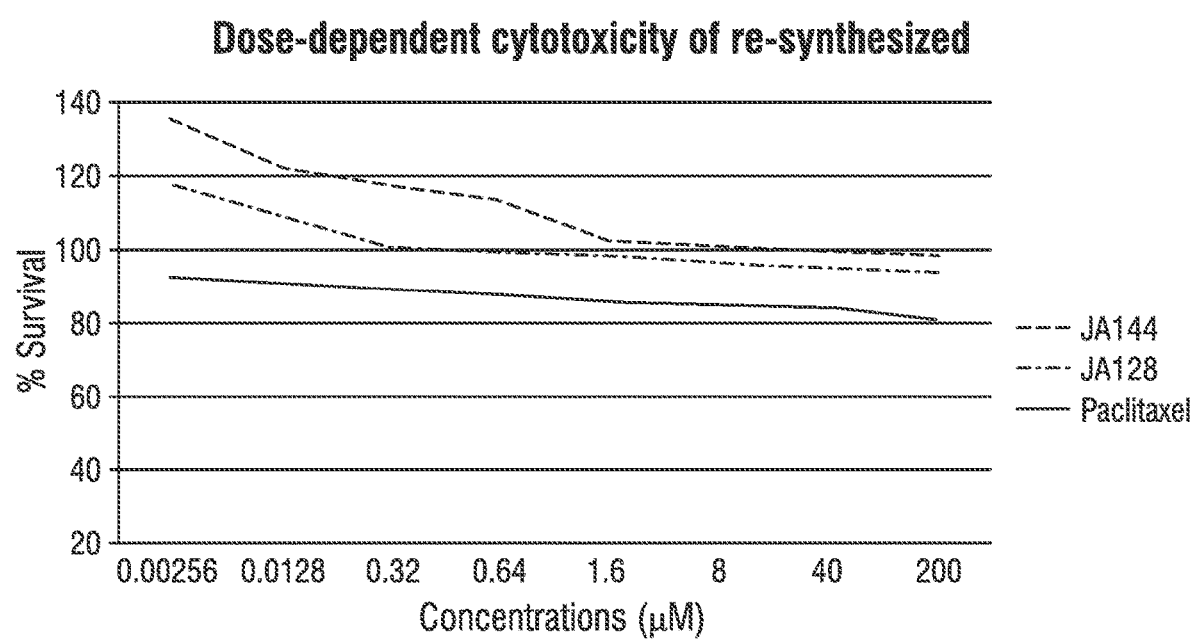
FIG. 16 is a graph showing dose-dependent cytotoxicity of JA-144 and JA-128 and Paclitaxel.

Results of the primary screening can be found in FIGS. 6-15. In FIG. 6 a graph is shown. As described in earlier primary screening, we screened 16 compounds for *C. jejuni* growth inhibition. A cut off percentage value of 70.0% growth inhibition was used to identify potent compounds. See FIG. 7. We also screened 15 derivatized compounds for *C. coli* growth inhibition. A cut off percentage value of 70.0% growth inhibition was used to identify potent compounds. Based on both *C. jejuni* and *C. coli* growth inhibition assay, we selected four derivatized (TH4, TH8, THI 1 and TH13) compounds (highlighted in red box) for further analysis. See FIGS. 8A and B. Testing the effect of TH-4 at two different concentrations on the growth of *C. jejuni* and *C.coli*. Where positive control (P CNTL) include Campylobacter culture with know antibiotics and negative control (N CNTL) include Camylobacer culture alone. See FIGS. 9A and B. Testing the effect of TH-8 at two different concentrations on the growth of *C. jejuni* and *C. coli*. Where positive control (P CNTL) include Campylobacter culture with known antibiotics and negative control (N CNTL) include Camylobacter culture alone. See FIG. 10. Testing the efficacy of TH4 and TH8 compounds when incorporated in edible films against *C. jejuni* and *C. coli*. Where control include edible film without any incorporation. Both TH4 and TH8 were effective in reducing *Campylobacter* by 4-6 log. See FIG. 11.

As described in primary HTS, we screened re-synthesized two compounds for *C. jejuni* 81-176 growth inhibition. Both re-synthesized compounds effective inhibiting *Campylobacter* growth at tested concentrations. FIGS. 12A and B shows texting the effect of re-synthesized compound JA-144 at two different concentrations on the growth of *C. jejuni* and *C. coli*. Where positive control (P CNTL includes *Campylobacter* culture with known antibiotics and negative control (N CNTL) include *Camylobacter* culture alone. See FIG. 13. Testing the efficacy of JA-144 when incorporated in edible films against pathogenic *E.coli*, *Listeria* strain, *C. jejuni* and *E. coli* bacteria. The control (CNTL) include edible film alone. JA-144 was effective in reducing most of the pathogenic bacteria by 4 log. See FIG. 14. A cytotoxicity assay for potent semi-synthetic derivative compounds were performed using normal colon cells and sulfohodamine B methods. See FIG. 15. A cytotoxicity assay was performed for two re-synthesized compounds using normal colon cells and sulforhodamine B methods.

Example 2

Abstract

This study investigated the antimicrobial activities of small molecule compounds (JA-144, TH-4, and TH-8) against *E. coli* K12, *Listeria innocua*, *Campylobacter jejuni* and *Campylobacter coli*. Minimum Inhibitory Concentrations (MIC) for JA-144 were 100 ppm against *E. coli* K12, 50 to 100 ppm against *L. innocua* at 37° C., and 3.125 to 6.25 ppm for *C. jejuni* and *C. coli* at 42° C., respectively. TH-4 and TH-8 were ineffective against *E. coli* K12 and *L. innocua*. The MICs for TH-4 were 12.5 to 25 ppm against *C. jejuni* and *C. coli* at 42° C., while for TH-8 they were 25 to 50 ppm. Growth curves for *E. coli* K12, *L. innocua*, and *C. jejuni* exposed to JA-144, TH-4 and TH-8 at their MICs showed that JA-144 completely inhibited *E. coli* K12 and *L. innocua* at 100 ppm and *C. jejuni* at 6.25 ppm, respectively, TH-4 completely inhibited *C. jejuni* at 25 ppm while TH-8 accomplished it at 50 ppm. When incorporated into dried tapioca films, efficacy losses for JA-144 were 43.48%, 36.42%, 0.25% and 2.03%, respectively for *E. coli* K12, *L. innocua*, *C. jejuni* and *C. coli*. TH-4 losses were 6.09% and 29.02%, respectively, while for TH-8 they were 25.52% and 48.01%, respectively, for *C. jejuni* and *C. coli*.

We have screened a pre-selected bioactive small molecule library of 4,182 compounds against highly pathogenic *C. jejuni* 81-176 strain. The objectives of this study were to investigate the antimicrobial activities of synthesized small molecules (JA-144, TH-4 and TH-8) (FIG. 1), identified from our earlier screen, dissolved in Dimethylsulfoxide (DMSO), and incorporated into tapioca edible films. Antibacterial properties were tested against *E. coli* K12 and *Listeria innocua*, *Campylobacter jejuni* and *Campylobacter coli*. The *E. coli* K12 and *L. innocua* were used as bacterial surrogates of *E.coli* O157:H7 and *L. monocytogenes*, respectively.

This structural scaffold of these compounds are amenable to preparing an array of structurally diverse compounds in essentially a single transformation from commercial precursors.

2. Materials and Methods 2.1. Materials

Tapioca starch powder was purchased from a local supermarket in Columbus, Ohio. It was irradiated at the Ohio State University Nuclear Reactor Laboratory in order to achieve sterilization. This was used as the main ingredient in the films. Distilled water was used to make a suspension of the starch powder. Glycerol≥99.0% (Sigma-Aldrich®) was obtained from Fisher Scientific (Fisher Scientific, Fair Lawn, N.J.) and used as a plasticizer. Acetic Acid (ACS Reagent≥99.7%), Dimethyl Sulfoxide (ACS Reagent≥99.9%) and 2,3,5-Triphenyltetrazolium Chloride (≥95.0%) were purchased from Sigma-Aldrich® and used as a solvent and bacterial dye agent, respectively. *E. coli* K12 and *Listeria innocua* were purchased from the American Type Culture Collection (Manassas, Va.). *Campylobacter jejuni* and *Campylobacter coli* were obtained from Dr. Rajashekara's laboratory, Wooster, Ohio. Tryptic Soy Broth (TSB) and Tryptic Soy Agar were purchased from Difco (Sparks, Md.). Mueller Hinton Agar, Mueller Hinton Broth and Fisher BioReagents Peptone (Granulated) were purchased from Thermo Scientific®, while 1.5 ml Micro Centrifuge Tubes, 96-Well Microplates, 100 mm Petri Dishes were obtained from Thermo Scientific®, respectively. The synthesized small molecules referred to as JA-144, TH-4 and TH-8 were obtained from Dr. James Fuch's laboratory at the College of Pharmacy, OSU. The chemical structures of these molecules are shown in FIG. 1.

2.2. Method 2.2.1. MIC Tests for Small Molecule Compounds.
2.2.1.1. Preparation of Bacterial Culture.

*E. coli* K12, *L. innocua*, *C. jejuni* and *C. coli* were used in the assay. The bacteria were maintained on nutrient agar slants at 4° C. Before use, a single colony of each bacterium was transferred into 50 ml tubes containing MHB using aseptic techniques. The tubes were capped and placed in an incubator overnight at 37° C., aerobically (for *E. coli* and *L. innocua*), and at 42° C. (for *C. jejuni* and *C. coli*), microaerobically. After 24 hours incubation, the broths were centrifuged at 4000 rpm for 5 min using appropriate aseptic precautions. The supernatants were discarded and the pellets resuspended using 20 ml of sterile peptone water and centrifuged again at 4,000 rpm for 5 min. This step was repeated until the supernatants were clear. The pellets were then suspended in 20 ml of sterile peptone water and labeled as Standard Broth (SB). As for *E. coli* K12, and *L. innocua*, six consecutive 10-fold dilutions were made to reach the initial inoculum of $10^3$ CFU/ml. For *C. jejuni* and *C. coli*, the initial inoculum was obtained by measuring the optical density of the SB at 595 nm, and serial dilutions carried out until the optical density reached 0.05, which was equal to $10^6$ CFU/ml.

2.2.1.2 Preparation of Small Molecule and Other Stock Solutions.

The small molecule solutions were prepared by dissolving 100 mg of each compound at room temperature in 1 ml DMSO in separate test tubes to reach a concentration of 100,000 ppm. A vortex mixer was used to ensure that each compound was well dissolved into a homogenous solution. The small molecule stock solutions were then stored at −20° C.

The 2,3,5-Triphenyltetrazolium Chloride (TTC) stock solution was prepared by dissolving 20 mg in 1 ml distilled water at room temperature to reach a concentration of 20,000 ppm. A vortex mixer was used to ensure that it was well dissolved. The TTC stock solution was stored at −20° C. for future use.

The range of concentrations for the small molecules in the films depended on previous cytotoxicity assay conducted by Dr. Esperanza Carcache de Blanco's laboratory in the College of Pharmacy at OSU. This test determined the highest concentrations of each compound to cause lysis of human colon cells. The results showed that the values for JA-144, TH-4 and TH-8 were 200 µM. When converted to ppm, they were 66.9 ppm, 61.1 ppm, 60.4 ppm, respectively. The survival rates of colon cells for JA-144, TH-4 and TH-8 at 200 µM were 99%, 60%, and 79%, respectively. Since JA-144 showed less toxicity on human colon cells, the starting concentration for this study was 100 ppm; while for TH-4 and TH-8, the starting concentration were 50 ppm, respectively.

2.2.1.3. Preparation of the Plates for MIC Testing.

A sterile 96 well plate was used for all MIC tests. A positive control was used in this study. This positive control was made of 198.6 µl of MHB with *E. coli* K12, *L. innocua*, *C. jejuni*, and *C. coli* at a concentration of $10^6$ CFU/ml, 0.4 µl of Chloramphenicol (2 µl/ml in broth), and 1 µl TTC stock solution (100 ppm in broth). This was pipetted into the first column of the plate. The MIC test groups were then placed in row 2 to row 11, plus 197 µl of MHB inoculated with *E. coli* K12, *L. innocua*, *C. jejuni*, or *C. coli* at $10^6$ CFU/ml, 2 µl of DMSO with diluted JA-144, TH-4 or TH-8, and 1 µl TTC stock solution. A negative control group was prepared by repeating the above but without JA-144, TH-4 or TH-8. This negative control group was pipetted into the last column of the plate. Triplicate tests were done for each bacterial strain. The 96-well micro plates with *E. coli* K12 and *L. innocua* were incubated at 37° C. aerobically for 24 hours; while the plates with *C. jejuni* and *C. coli* were incubated at 42° C. microaerobically for 24 hours, respectively. The MIC was the lowest concentration of the agent that completely inhibited visible growth of the test microorganisms. The MIC values depended on a color change. No color change was observed when growth of the bacteria was inhibited.

TABLE 1

Composition of Tapioca Film on Wet and Dry Percent Weight Basis.

| Wet basis | | Dry basis | |
| --- | --- | --- | --- |
| Composition | Weight % | Composition | Weight % |
| Tapioca starch | 5% | Tapioca starch | 72.78% |
| Glycerol | 1.8% | Glycerol | 26.20% |
| Acetic acid | 0.7% | Small molecules | 1.02% |
| Small molecules | 0.07% | | |
| Distilled water | 93.23% | | |
| Total | 100% | Total | 100% |

2.2.1.4. Growth Curves Bacteria Against all Test Compounds at the MIC Values.

For *E. coli* K12 and *L. innocua*, the bacterial incubations were followed by measurements of the Optical Density (OD) values every 15 minutes in an automated Sunrise™ Tecan Spectrophotometer (Tecan Co.) during an incubation period of 24 hours at 37° C. For *C. jejuni*, the incubation experimental design was similar, but the measurement period occurred every 4 hours. From the data collected, comparisons were made with the control samples and statistical analyses were used to determine the significance between the means for all observations.

2.2.2. Preparation of Tapioca Films.

The film forming solutions were prepared using blends of tapioca starch and JA-144, TH-4 and TH-8 dissolved in acetic acid with glycerol as a plasticizer. This began when aliquots of 100 mg of each small molecule compound was first dissolved in 1 ml acetic acid. Tapioca starch (5% w/w) and acetic acid solutions (0.7% w/w) with the small molecules and 1.8% w/w glycerol were dissolved into 100 ml distilled water as shown in Table 2.

TABLE 2

A summary of Log Reduction Tests for
E. coli K12 and L. innocua.

|  |  | E. coli K12 | L. innocua |
|---|---|---|---|
| In Broth | JA-144 | 2.96 ± 0.30[a] | 3.14 ± 0.11[b] |
|  | CNTL | 8.81 ± 0.15[a] | 8.66 ± 0.09[b] |
|  | Log$_{10}$ CFU/ml reduction | 5.86 | 5.52 |
| In Film | JA-144 | 5.58 ± 0.08[a] | 5.22 ± 0.07[b] |
|  | CNTL | 8.90 ± 0.13[a] | 8.73 ± 0.29[b] |
|  | Log$_{10}$ CFU/ml reduction | 3.31 | 3.51 |
| Percent efficacy loss due to incorporation |  | 43.48% | 36.42% |

Values within the same row with the same letters are not significantly different (p > 0.05).

All dispersions were heated in a water bath (70° C.) for 15 min with stirring until completely gelatinized. An Ultrasonic Sonicator (Graymills Co., Chicago, Ill.) was used to remove air bubbles from the gelatinized solutions. The edible films were prepared by casting the solutions (107 g) into 10-inch radius Teflon plates. These were oven dried at 45±2° C. for 12 hours, then the dried films peeled off from the plate surfaces. The final concentration of each small molecule compound in the dry film was approximately 1% w/w. The film thicknesses were measured using a Magna-Mike 8500 Thickness Gage (Olympus, Japan), with resolution of 0.001 mm. A total of 5 measurements per film, at various locations were taken to determine the average thickness.

2.2.3. Inoculation and Testing of Dry Tapioca Films against Test Microorganisms.

The films prepared above were cut into small pieces that were capable of fitting into 1.5 ml micro-tubes. The weight of each film sample ranged from 5 to 15 mg. The micro-tubes were then exposed to UV light for 18 hours to eliminate possible contamination that may have occurred during the cutting and transferring process. The amount of bacterial culture in each tube depended on two factors: the amount of small molecules in the film, and the MIC value that completely inhibited the bacterial growth. After adding the proper amount of bacterial culture, the micro-tubes were placed in an incubator aerobically at 37° C. (for E. coli and L. innocua), or microaerobically at 42° C. (for C. jejuni and C. coli), for 24 hours, respectively. The antimicrobial activity tests using tapioca starch films incorporated with the JA-144, TH-4 or TH-8 were followed by MIC and bacterial growth curve tests. Preparation of the bacterial cultures was the same as for the MIC tests.

To determine the test microbial growth kinetics, Mueller Hinton Agar (MHA) was used as a growth medium. A 4% w/w solution was prepared by dissolving 40 g MHA powder in 1,000 ml distilled water and then sterilized at 121° C. for 25 min. It was then transferred to a 50° C. water-bath and allowed to cool. Afterwards, it was poured into pre-labeled sterile Petri dishes on a level surface at room temperature (23° C.) and dried so that no drops of moisture remained on surface of the agar.

2.2.4. Inoculation of Plates

After 24 hours incubation, the broth was centrifuged at 4,000 rpm for 5 min at 23° C. with appropriate aseptic precautions. The supernatant was discarded and the pellet resuspended using 1 ml of sterile peptone water and centrifuged again at 4000 rpm for 5 min. This step was repeated until the supernatant was clear. The pellets were then suspended in 1 ml sterile peptone water, and seven consecutive 10-fold dilutions were made to obtain inoculums ready for the plate counts. For the experimental groups with the small molecule compounds, 0.1 ml of diluted broth (dilution of $10^{-2}$; $10^{-4}$; $10^{-6}$) were inoculated on to the plates. For the control groups, 0.1 ml of diluted broth (dilution of $10^{-6}$ and $10^{-7}$) was added to the plates. They were then incubated at 37° C. aerobically (for E. coli and L. innocua), or 42° C. microaerobically (for C. jejuni and C. coli) for 24 hours, and then colony numbers on each plate counted using a Darkfield Colony Counter manufactured by American Optical (Buffalo, N.Y.).

2.3. Statistical Analysis

All experiments were performed in triplicate and differences in the means analyzed by a SAS statistical program. One-way analysis of variance (ANOVA) was carried out to evaluate significance in differences (p<0.05) between the influences of the small molecules on the microbial growth.

3. Results and Discussion 3.1 MIC Tests of JA-144, TH-4 and TH-8

The MIC of JA-144 against E. coli K12 was 100 ppm, while the result for L. innocua, ranged from 50 ppm to 100 ppm. The MIC of JA-144 against C. jejuni and C. coli ranged from 3.125 ppm to 6.25 ppm, respectively. The results showed that TH-4 had no antimicrobialactivity against E. coli K12 and L. innocua. However, the MIC of TH-4 against C. jejuni and C. coli ranged from 12.5 ppm to 25 ppm, respectively. TH-8 also did not show antimicrobialactivity against E. coli K12 and L. innocua, but for C. jejuni and C. coli, the MIC ranged from 25 ppm to 50 ppm, respectively.

Figure 17:
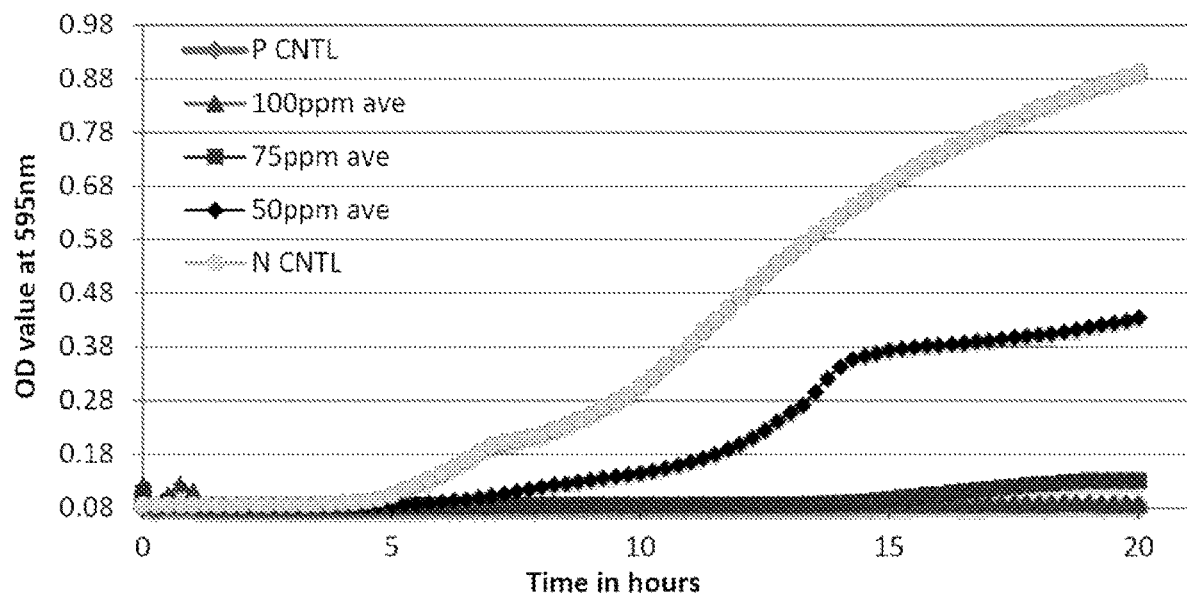
FIG. 17 is a graph showing *E. coli* growth curve when exposed to JA-144 at varying concentrations.
Figure 18:
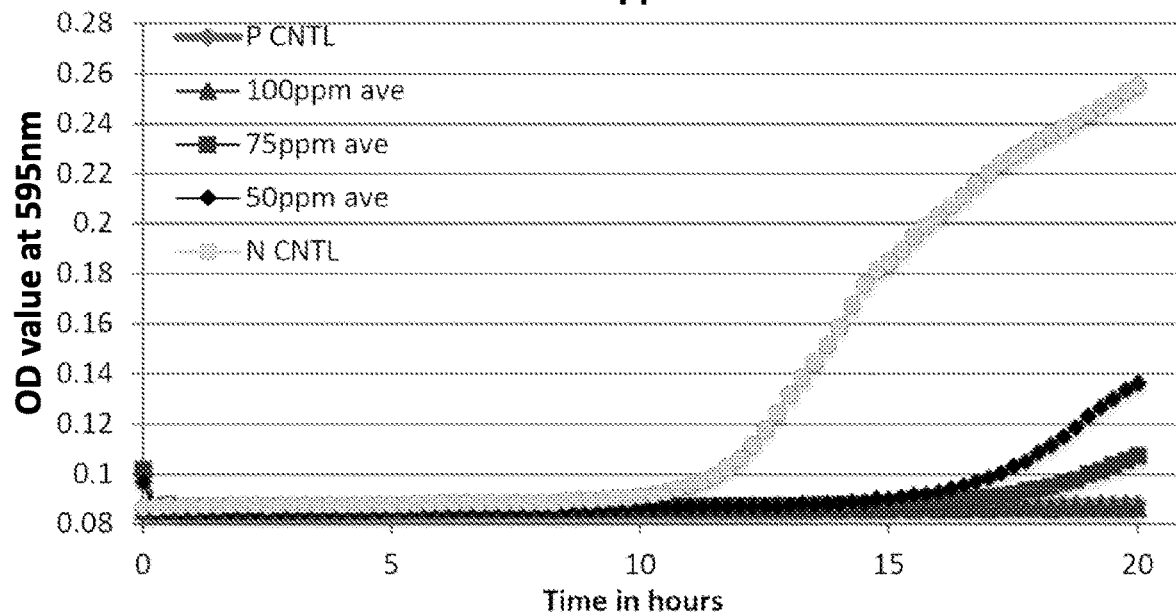
FIG. 18 is a graph showing *L. innocuous* growth curve when exposed to JA-144 at varying concentrations.
Figure 19:
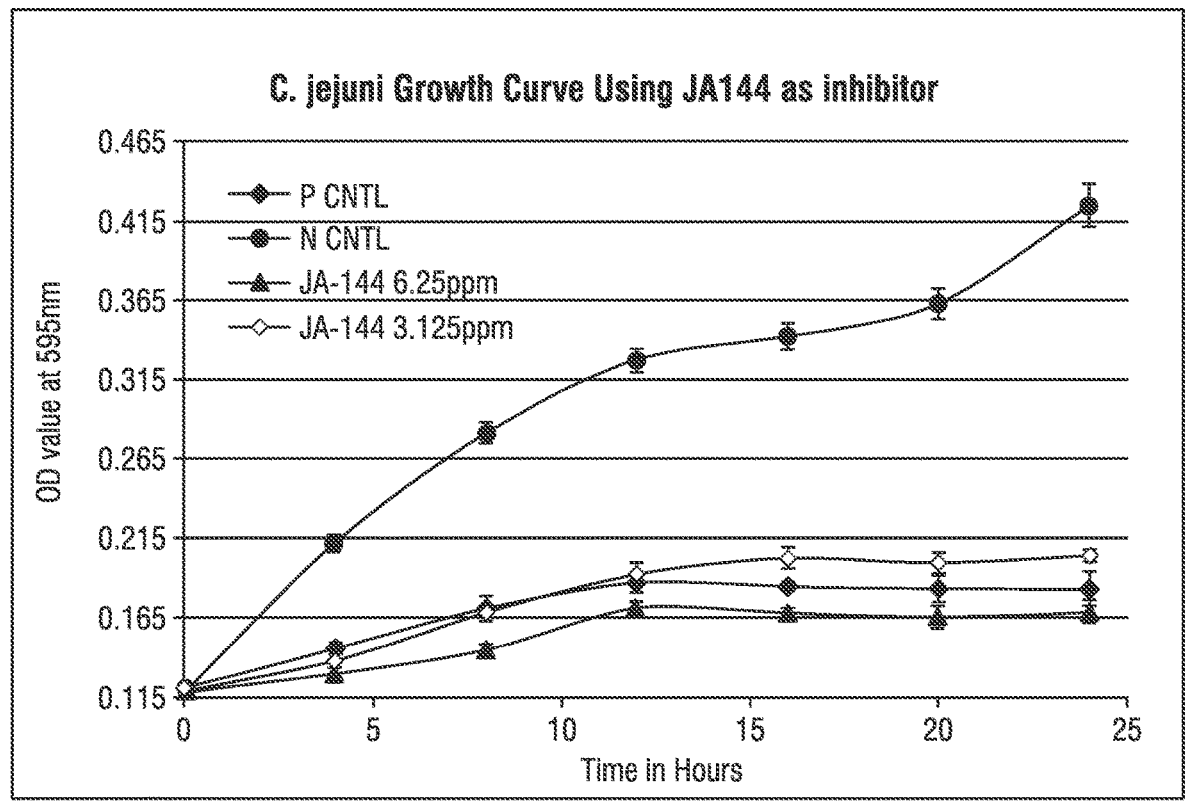
FIG. 19 is a graph showing *C. jejuni* growth curve when exposed to JA-144 at varying concentrations.
Figure 20:
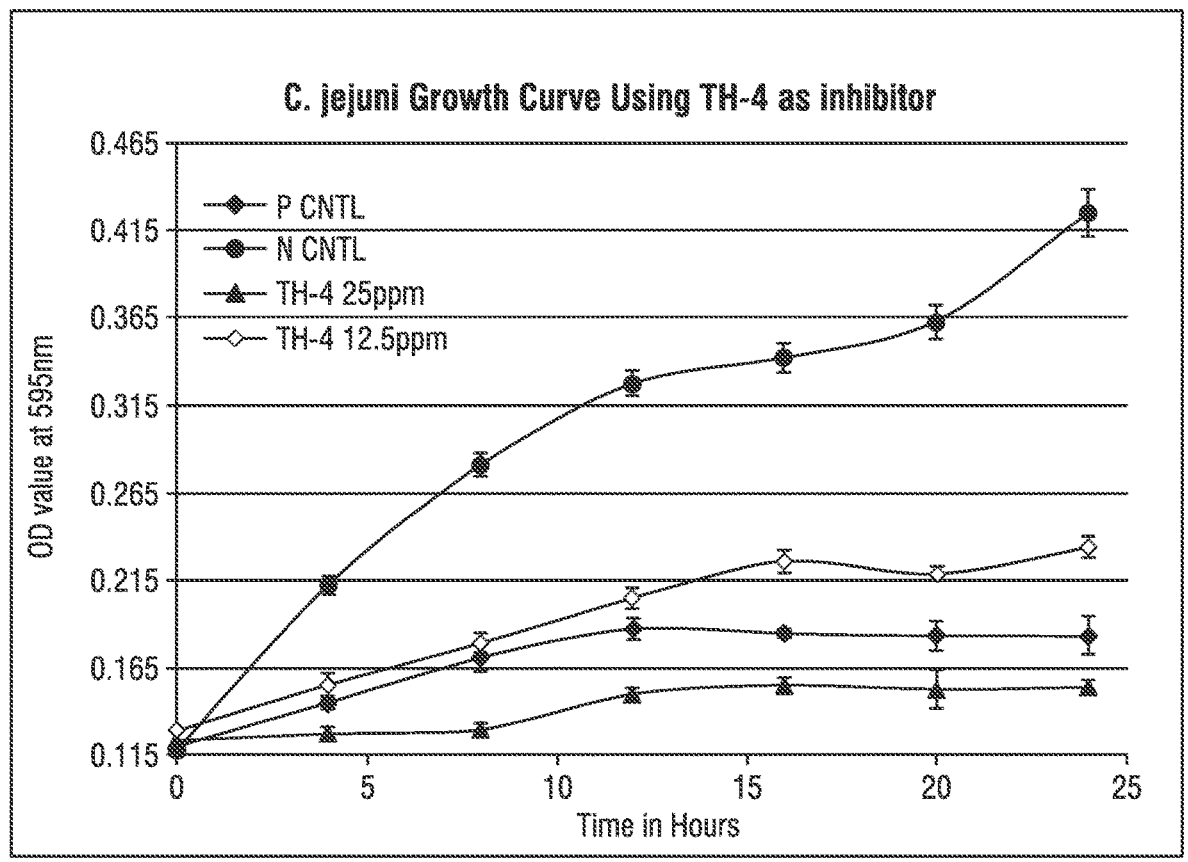
FIG. 20 is a graph showing *C. jejuni* growth curve when exposed to TH-4 at varying concentrations.
Figure 21:
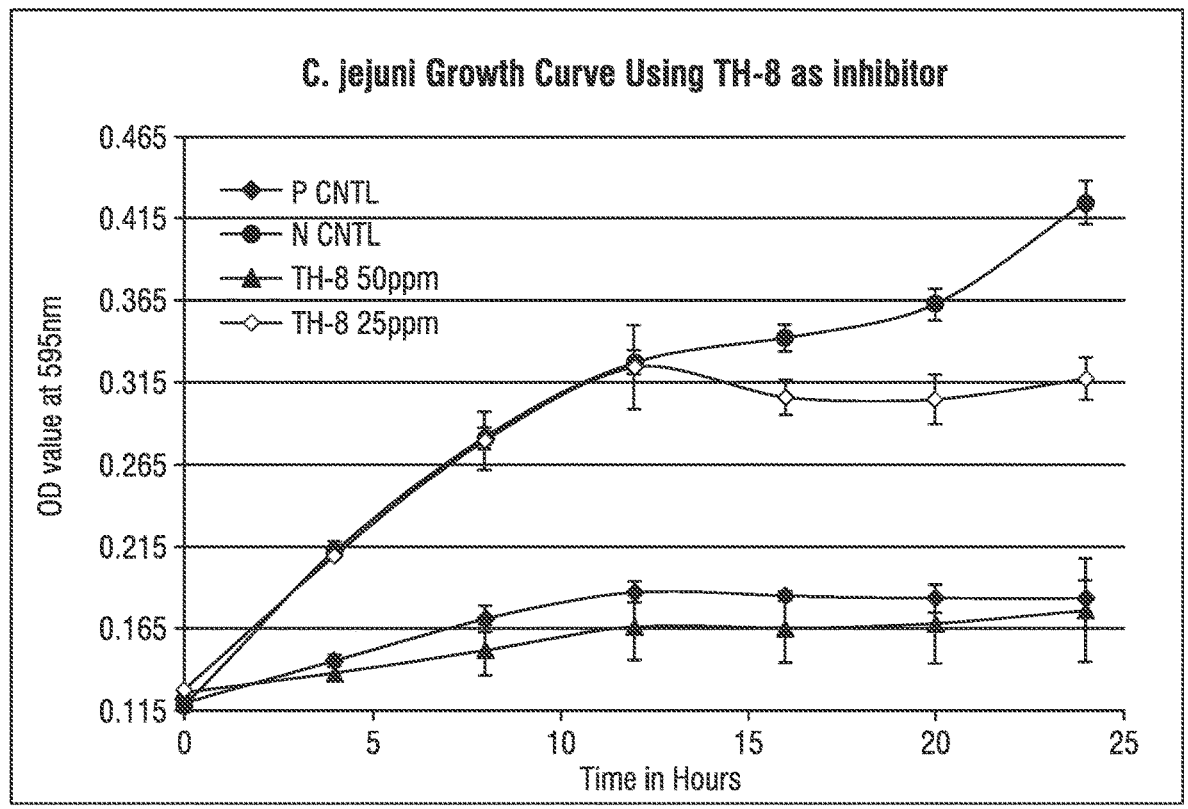
FIG. 21 is a graph showing *C. jejuni* growth curve when exposed to TH-8 at varying concentrations.

3.2 Bacterial Growth Curves of Test Microorganisms Against Small Molecules at MIC FIG. 17 shows the growth curve results for E. coli K12 exposed to varying concentrations of JA-144. At 100 ppm concentration level, the growth of E. coli K12 was not detected. The 50 ppm was least effective but still inhibited the growth of E. coli K12 more than that of the negative control. Similar results were obtained for JA-144 against L. innocua (FIG. 18). For C. jejuni treated with JA-144, FIG. 19 shows that the growth of the organism was inhibited more by the 6.25 ppm treatment when compared with the 3.125 ppm. The results also show that the 6.25 ppm treatment had a greater impact when compared with the positive control. A similar result was also obtained for C. jejuni treated with TH-4 at 25 and 12.5 ppm (FIG. 20). In that case, the 25 ppm treatment was more effective than the positive control. For the TH-8 tests, as shown in FIG. 21, the results show that the growth of C. jejuni was completely inhibited by a concentration of 50 ppm.

Figure 22A:
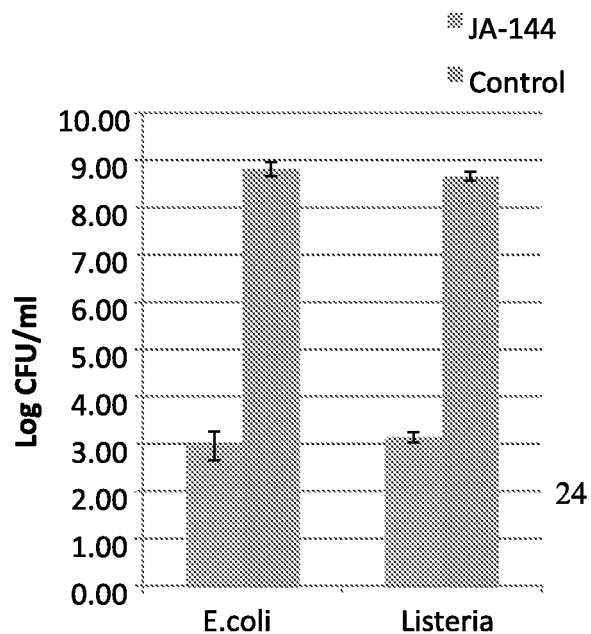
FIGS. 22A and B are graphs showing log reduction of bacteria when exposed to JA-144 in broth (A) and in tapioca film (B).
Figure 23A:
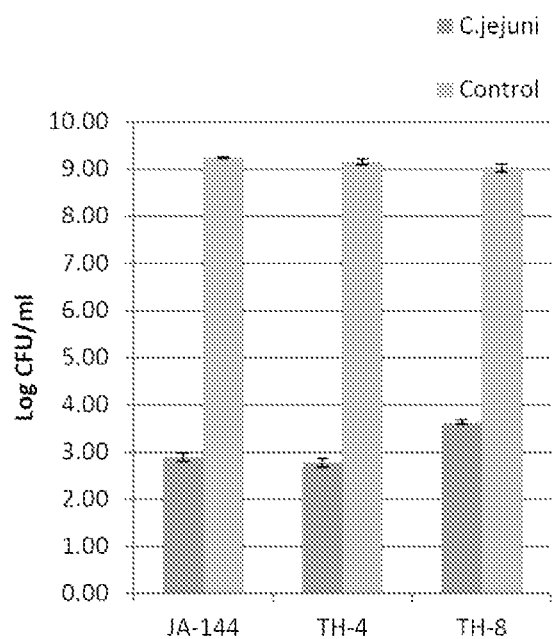
FIGS. 23A and B are graphs showing log reduction of *C. jejuni* (left bar) when exposed to JA-144, TH-4 and TH-8 in broth and control (right bar)(A) and *C. coli* (B).
Figure 23B:
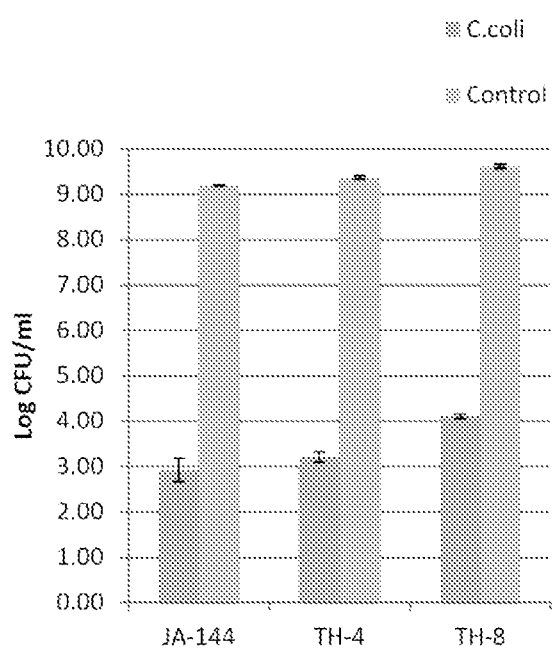

3.3 Antimicrobial Tests of JA-144 in Growth Medium Against E. coli K12 and L. innocua FIGS. 22A and B shows the effect of 100 ppm JA-144 (in the broth) on E. coli K12 and L. innocua. The results show significant reductions (p<0.05) of 5.86 and 5.52 log$_{10}$ CFU/ml, respectively after 24 hours incubation when compared with the control. For C. jejuni and C. coli in the broth, JA-144 at 6.25 ppm and 3.125 ppm concentrations resulted in significant reductions (p<0.05) of 6.35 and 6.27 log$_{10}$ CFU/ml, respectively after 24 hours incubation (FIGS. 23A and B), when compared with the control.

For TH-4 at 25 ppm and 12.5 ppm concentrations against C. jejuni and C. coli in broth, the results show significant reductions (p<0.05) of 6.37 and 6.16 log$_{10}$ CFU/ml, respectively after 24 hours incubation (FIGS. 23A and B), when compared with the control.

When C. jejuni and C. coli in the broth were treated by 50 ppm TH-8, the results showed significant differences (p<0.05) of 5.39 and 5.51 log$_{10}$ CFU/ml, respectively after 24 hours incubation (FIGS. 23A and B), when compared with the control. All log reduction-testing results are summarized in Tables 3, 4 and 5.

TABLE 3

A Summary of Log Reduction Tests for *C. jejuni* and *C. coli*.
In Broth

*C. jejuni*

| | *C. jejuni* | Control | $Log_{10}$ CFU/ml reduction |
|---|---|---|---|
| JA-144 | $2.90 \pm 0.09^a$ | $9.25 \pm 0.01^{ab}$ | 6.35 |
| TH-4 | $2.78 \pm 0.09^a$ | $9.15 \pm 0.06^{ab}$ | 6.37 |
| TH-8 | $3.64 \pm 0.05^a$ | $9.03 \pm 0.08^{ab}$ | 5.39 |

*C. coli*

| | *C. coli* | Control | $Log_{10}$ CFU/ml reduction |
|---|---|---|---|
| JA-144 | $2.93 \pm 0.26^a$ | $9.20 \pm 0.02^{ab}$ | 6.27 |
| TH-4 | $3.21 \pm 0.12^a$ | $9.38 \pm 0.04^{ab}$ | 6.16 |
| TH-8 | $4.11 \pm 0.05^a$ | $9.62 \pm 0.04^{ab}$ | 5.51 |

Values within the same row with the same letters are not significantly different (p > 0.05).

TABLE 4

A Summary of Log Reduction Tests for *C. jejuni* and *C. coli*. Values within the same row with the same letters are not significantly different (p > 0.05)
In Broth

*C. jejuni*

| | *C. jejuni* | Control | $Log_{10}$ CFU/ml reduction |
|---|---|---|---|
| JA-144 | $2.90 \pm 0.09^a$ | $9.25 \pm 0.01^{ab}$ | 6.35 |
| TH-4 | $2.78 \pm 0.09^a$ | $9.15 \pm 0.06^{ab}$ | 6.37 |
| TH-8 | $3.64 \pm 0.05^a$ | $9.03 \pm 0.08^{ab}$ | 5.39 |

*C. coli*

| | *C. coli* | Control | $Log_{10}$ CFU/ml reduction |
|---|---|---|---|
| JA-144 | $2.93 \pm 0.26^a$ | $9.20 \pm 0.02^{ab}$ | 6.27 |
| TH-4 | $3.21 \pm 0.12^a$ | $9.38 \pm 0.04^{ab}$ | 6.16 |
| TH-8 | $4.11 \pm 0.05^a$ | $9.62 \pm 0.04^{ab}$ | 5.51 |

Values within the same row with the same letters are not significantly different (p > 0.05).

TABLE 5

A Summary of Log Reduction Tests for *C. jejuni* and *C. coli*.
In Film

*C. jejuni*

| | *C. jejuni* | Control | $Log_{10}$ CFU/ml reduction | % Efficacy loss due to incorporation |
|---|---|---|---|---|
| JA-144 | $2.86 \pm 0.13^a$ | $9.22 \pm 0.05^{ab}$ | 6.36 | 0.25 |
| TH-4 | $3.16 \pm 0.14^a$ | $9.15 \pm 0.07^{ab}$ | 5.99 | 6.09 |
| TH-8 | $5.10 \pm 0.07^a$ | $9.11 \pm 0.12^{ab}$ | 4.01 | 25.52 |

TABLE 5-continued

A Summary of Log Reduction Tests for *C. jejuni* and *C. coli*.
In Film

*C. coli*

| | *C. coli* | Control | $Log_{10}$ CFU/ml reduction | % Efficacy loss due to incorporation |
|---|---|---|---|---|
| JA-144 | $2.93 \pm 0.16^a$ | $9.07 \pm 0.05^{ab}$ | 6.14 | 2.03 |
| TH-4 | $5.03 \pm 0.07^a$ | $9.40 \pm 0.04^{ab}$ | 4.37 | 29.02 |
| TH-8 | $6.83 \pm 0.06^a$ | $9.70 \pm 0.07^{ab}$ | 2.87 | 48.01 |

Values within the same row with the same letters are not significantly different (p > 0.05)

Figure 22B:
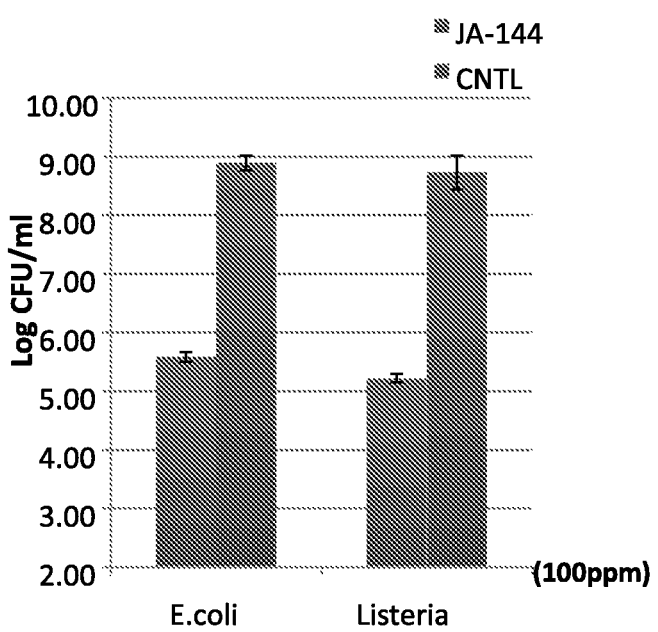
Figure 24A:
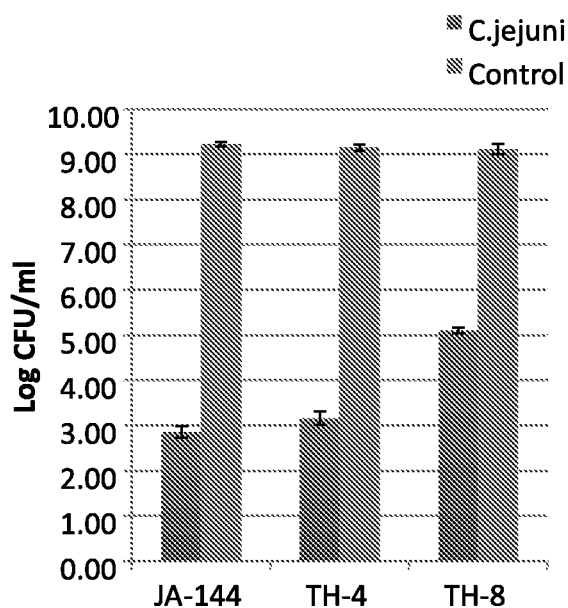
FIGS. 24A and B are graphs showing log reduction of *C. jejuni* (left bar) when exposed to JA-144, TH-4 and TH-8 in broth and control (right bar) (A) and *C. coli* (B).
Figure 24B:
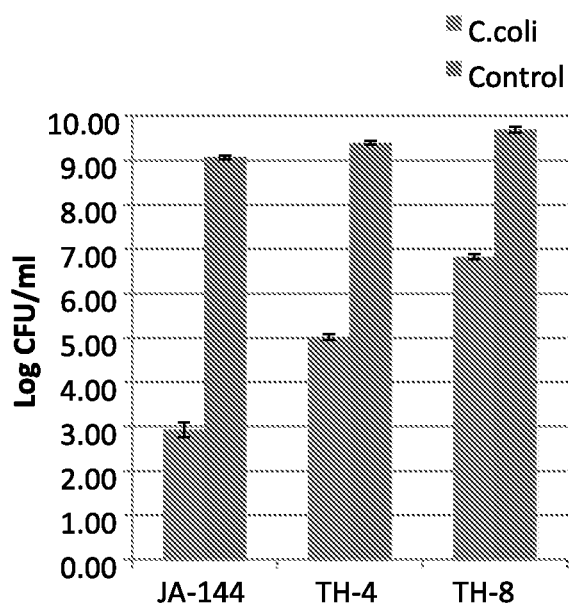

3.4 Antimicrobial Activity Tests of all Compounds Incorporated into Tapioca Films For *E. coli* K12 and *L. innocua*, 1% w/w of JA-144 film resulted in significant reductions (p<0.05) of 3.31 and 3.51 $log_{10}$ CFU/ml, respectively after 24 hours incubation (FIG. 22B), when compared with control. The percentages of antimicrobial activity lost due to incorporation of JA-144 into the tapioca films were 43.48% and 36.42%, respectively. For *C. jejuni* and *C. coli*, JA-144 at 6.25 ppm and 3.125 ppm resulted in significant reductions (p<0.05) of 6.36 and 6.14 $log_{10}$ CFU/ml, respectively after 24 hours incubation (FIGS. 24A and B), when compared with control. Percentages of antimicrobial activities lost due to incorporation of JA-144 into the tapioca films were 0.25% and 2.03%, respectively.

For TH-4 at 25 ppm and 12.5 ppm against *C. jejuni* and *C. coli*, the results show significant reduction (p<0.05) of 5.99 and 4.37 $log_{10}$ CFU/ml, respectively after 24 hours incubation (FIG. 24A), when compared with control. Percentages of antimicrobial activities lost when TH-4 was incorporated into the films were 6.09% and 29.02% for *C. jejuni* and *C. coli*, respectively.

When *C. jejuni* and *C. coli* were treated by TH-8 at 50 ppm, the reductions in growth were significant (p<0.05) at 4.01 and 2.87 $log_{10}$ CFU/ml, respectively after 24 hours incubation (FIGS. 24A, B), when compared with control. The reductions in antimicrobial activities caused by incorporating TH-8 into the films were 25.52% and 48.01% for *C. jejuni* and *C. coli*, respectively. All log reduction-testing results are summarized in Table 4 and Table 5.

4. Discussion 4.1 Minimum Inhibitory Concentration (MIC) Tests for JA-144, TH-4 and TH-8

It is to be noted that MIC values for JA-144 against *C. jejuni* and *C. coli* were significantly lower than for *E. coli* K12 and *L. innocua*, suggesting that *Campylobacter* spp. was more sensitive to JA-144. This could be explained by the fact that aerobic bacteria grow 30 to 50 times faster than microaerobic bacteria (Mosen, 2006). This faster growth rate of aerobic bacteria is indicative of their greater resistance to drugs, when compared with microaerobes (Diana et al., 1991). The results also revealed that JA-144 inhibited all tested bacteria, while TH-4 and TH-8 were only effective against the *Campylobacter* species. This could be attributed to the polar hydroxyl group in the JA-144 molecule. Rotunda et al., (2010) reported that hydroxyl groups could disrupt the integrity of biological membranes by binding to the phospholipid bilayer hydrophobic core, solubilizing membrane-associated proteins, and finally causing membrane breakdown and lysis of the bacterial cell membrane.

4.2 Growth Curve Measurements Using JA-144, TH-4, and TH-8 as Inhibitors at MIC The bacterial growth curve measurement revealed how the bacterial populations were affected by JA-144, TH-4 and TH-8 at their MICs. The OD values provided quantitative information and thus narrowed down the MICs of JA-144, TH-4 and TH-8 to specific values. However, the OD method is a rough estimate, and the bacterial growth is not observed with OD value until the cell concentration reached approximately $10^7$ CFU/ml (Christina et al., 2014). Thus, it could be concluded that even a small increase observed in the OD values in these experiments could mean that significant changes in microbial populations occurred. Therefore, statistical analysis of these OD measurements could not objectively reflect differences in the microbial populations.

4.3. Antimicrobial Activities of JA-144, TH-4 and TH-8 with and without Films Against *E. coli* K12, *L. innocua*, *C. Jejuni* and *C. coli* at Each MIC Typically, when an antimicrobial agent is incorporated into a film or bonded to the surface as a coating, it could lose some of its efficacy. If the functional groups of the antimicrobial agent bind too tightly to the polymer, the releasing rate will be highly restricted when they contact a contaminated surface (Han, 2000). Consequently, growth of the microorganism will continue before the antimicrobial agent is released. On the other hand, if the releasing rate of antimicrobial agent is faster than the growth rate of the target microorganism, the antimicrobial agent could be depleted and loses its efficacy quickly since packaged food has an almost infinite volume compared to the amount of the antimicrobial agent (Raija, 2003). In addition, the processing method used in the manufacture of the film could act to interfere with the antimicrobial function of the active agent (Wen-Xian et al., 2015). For polymeric films, this could occur during the synthesis process, if that is when the antimicrobial agent is incorporated or it could occur during the extrusion process, when the resin is converted into a film. This extrusion process melts the polymeric resin into a flowing liquid before cooling it into the final desired shape as a film.

Reduction in the activities of the antimicrobial compounds, when incorporated into the films, could be attributed to the nature of the functional groups and if they interact negatively with those of the polymer. For example, the hydroxyl group in JA-144 was more likely to interact with the tapioca starch granules and glycerol since they are hydrophilic. However, as for *C. jejuni* and *C. coli*, the losses in efficacies for JA-144 were only 0.25% and 2.03%. These were significantly lower than the reductions obtained when exposed to *E. coli* K12 or *L. innocua*. This could be attributed to the microaerobic nature of the *Campylobacter* species and the fact that this lead to their slow growth rate. Based on this premise, it can be assumed that the release rate of JA-144 and *Campylobacter*'s growth rate were perfectly matched.

5. Conclusion

In this study, the antimicrobial effect of the synthesized small molecules (JA-144, TH-4 and TH-8) against *E. coli* K12, *L. innocua*, *C. jejuni* and *C. coli* were evaluated qualitatively and quantitatively. It could be concluded that JA-144 was most effective in inhibiting the growth of the all the test organisms when compared with TH-4 and TH-8. TH-4 showed better antimicrobial activities than TH-8. The *Campylobacter* species appeared to be more sensitive to the small molecule compounds when compared with *E. coli* K12 or *L. innocua*. Although the antimicrobial efficacy of the small molecule compounds appeared to be reduced after they were incorporated into the edible films, for JA-144 and TH-4, the reductions were not significant when compared to direct exposure of the microorganisms to the antimicrobial agents. Thus, it could be concluded that JA-144 has great potential to be incorporated into edible films and could be used to package and reduce bacterial growth on ready-to-eat foods. However, additional researches on the release rate of the compounds from the films are needed since this is indispensable to understanding of how the molecules will behave within the film. Additionally, the mechanical properties of the films should be investigated to ascertain if and how the functionality would be affected by the addition of small molecule compounds.

Example 3

Abstract

This study incorporated antimicrobial small molecule compounds (JA-144, TH-4, and TH-8) into tapioca films and investigated how they influenced thickness, moisture content, water activity, gas permeation, morphology, thermal and mechanical properties of the films. Results showed that, unlike TH-4 and TH-8, JA-144 caused significant ($p<0.05$) changes to thickness, moisture content, and water activity of the films when compared with the control film. JA-144 caused a small but significant ($p<0.05$) increase in water vapor permeation (WVP) while TH-4 and TH-8 caused a small lowering of the WVP. For the oxygen permeation, JA-144 and TH-4 cause a small but significant increase but TH-8 had no significant effect. Compared to the melt temperature of the control (122.63° C.), JA-144 reduced it to 119.84° C. while TH-4 and TH-8 increased it to 126.49° C. and 130.68° C., respectively. X-ray diffraction testing showed that JA-144 did not induce crystallinity changes, but TH-4 and TH-8 appeared to increase crystallinity and subsequent crosslinking effects. The Dynamic Mechanic Analysis tests showed that JA-144 had no effect on the glass transition temperature ($T_g$) and storage modulus, while TH-4 and TH-8 that caused slight increases in $T_g$ and storage modulus of the films. The JA-144 films had higher moisture content and water activities while these were lower in the TH-4 and TH-8 films. These results indicate that JA-144 caused the films to be more flexible, higher in moisture and lower in gas barrier properties. TH-4 and TH-8 did the opposite by making the films stiffer, lower in moisture and better barriers to gasses.

1. Introduction

Increasing demands for environmental-friendly packaging material have triggered sustained researches in the development of starch-based bio-composite films. Starch is one of the most preferred green packaging materials due to its rapid biodegradable nature, renewable sources and availability at relatively low cost (Liu et al., 2011). Films made from starch could be used to cover food surfaces, separate incompatible zones and ingredients in complex food mixes, form a barrier against oxygen, aroma, oil and moisture, and used to make pouches or wraps for food packaging. Besides, edible films can be used as carriers of functional agents, such as antioxidants or antimicrobials, and can be used to improve the appearance of selected foods (Kester and Fennema, 1986).

Tapioca is obtained from the cassava plant, which is a significant crop in South America, Africa, Latin America and Asia, and is an economical source of starch (FAO, 2004). Films made from tapioca starch exhibit appropriate physical characteristics, since they are odorless, tasteless, colorless, and good barriers to oxygen. However, tapioca starch-based films could show brittleness with inadequate mechanical properties if not properly made. To overcome this weakness, plasticizers are generally required because it could reduce the intermolecular forces and increase the mobility of polymer chains, therefore improving the flexibility and extensibility of the film. Glycerol is one example of a plasticizer used in filmmaking. It shows stability and compatibility with hydrophilic bio-polymeric materials used for packaging (Fernandez Cervera et al., 2004). However, high water solubility and poor water vapor barrier limit the application of hydrophilic materials such as starch-based films. To solve these problems, the blending of starch with different biopolymers or the addition of hydrophobic materials such as oils or waxes have been proposed (Xu et al., 2005; Garcia et al., 2000; Anker et al., 2001).

Antimicrobial(AM) agents have been found to be effective against food-borne pathogens. It is reported that the effectiveness of AM packaging is greater than direct addition of AM agents into foods due to two factors. One is the lower release rate of the AM agent from the material to the food, thus enabling functionality over a longer period. The other factor is inactivation concerns (such as neutralization, hydrolysis, or dilution) when the AMs are directly added into the food. Various types of AM agents have been incorporated into edible films. Examples of these include benzoic, sorbic, propionic, and lactic acids, nisin, and lysozyme, to retard surface growth of bacteria, yeasts, and molds on a wide range of products, including meats and cheeses (Islam et al., 2002; Lahellec, et al., 1981; Lueck, E., 1976; Moir, et al., 1992; Reddy, et al., 1982; Sofos, et al., 1981). Small organic molecules have always been of interest to chemists and biochemists due to their capability of exerting powerful effects on the functions of macromolecules that comprise living systems (Marian et al., 1997). As one of the most important therapeutic agents, small organic molecules have benefits such as improved stability over peptides in oral administration, synthetic accessibility, and optimization of convenience for compound bioactivity when compared with macromolecules (Pathania et al., 2009). Synthesized small molecules are generally used to affect the growth of bacteria in two ways: by killing the bacteria, or inhibiting the growth of the bacteria. However, the incorporation of additives into the matrix of a polymer may alter its mechanical and barrier properties, which are two important factors known to affect the performance of edible films.

The objectives of this study were to investigate how the addition of synthesized small molecules (JA-144, TH-4 and TH-8) could affect a tapioca starch-based film's thickness, morphology, moisture content, oxygen and water vapor permeabilities, glass transition and melting temperatures and mechanical properties.

2. Materials and Methods

2.1. Materials

Tapioca starch powder was purchased from a local supermarket in Columbus, Ohio. It was irradiated at the Ohio State University Nuclear Reactor Laboratory in order to achieve sterilization. This was used as the main ingredient in the films. Distilled water was used to make a suspension of the starch powder. Glycerol≥99.0% (Sigma-Aldrich®) was obtained from Fisher Scientific (Fisher Scientific, Fair Lawn, N.J.) and used as a plasticizer. Acetic Acid (ACS Reagent≥99.7%), Dimethyl Sulfoxide (ACS Reagent≥99.9%). The synthesized small molecules referred to as JA-144, TH-4 and TH-8 were obtained from Dr. James Fuch's laboratory at the College of Pharmacy, OSU. The chemical structures of these molecules are shown in FIG. 1.

3.2. Method 2.2.1. Preparation of Small Molecule Compounds.

The small molecule solutions were prepared by dissolving 100 mg of each compound at room temperature in 1 ml DMSO in separate test tubes to reach a concentration of 100,000 ppm. A vortex mixer was used to ensure that each compound was well dissolved into a homogenous solution. The small molecule stock solutions were then stored at −20° C.

The 2,3,5-Triphenyltetrazolium Chloride (TTC) stock solution was prepared by dissolving 20 mg in 1 ml distilled water at room temperature to reach a concentration of 20,000 ppm. A vortex mixer was used to ensure that it was well dissolved. The TTC stock solution was stored at −20° C. for future use.

The range of concentrations for the small molecules in the films depended on previous cytotoxicity assay conducted by Dr. Esperanza Carcache de Blanco's laboratory in the College of Pharmacy at OSU. This test determined the highest concentrations of each compound to cause lysis of human colon cells. The results showed that the values for JA-144, TH-4 and TH-8 were 200 µM. When converted to ppm, they were 66.9 ppm, 61.1 ppm, 60.4 ppm, respectively. The survival rates of colon cells for JA-144, TH-4 and TH-8 at 200 µM were 99%, 60%, and 79%, respectively. Since JA-144 showed less toxicity on human colon cells, the starting concentration for this study was 100 ppm; while for TH-4 and TH-8, the starting concentration were 50 ppm, respectively.

2.2.2. Preparation of Tapioca Films.

The film forming solutions were prepared using blends of tapioca starch and JA-144, TH-4 and TH-8 dissolved in acetic acid with glycerol as a plasticizer. This began when aliquots of 100 mg of each small molecule compound was first dissolved in 1 ml acetic acid. Tapioca starch (5% w/w) and acetic acid solutions (0.7% w/w) with the small molecules and 1.8% w/w glycerol were dissolved into 100 ml distilled water as shown in Table 6.

TABLE 6

Composition of Tapioca Film on Wet and Dry Percent Weight Basis.

| Wet basis | | Dry basis | |
| --- | --- | --- | --- |
| Composition | Weight % | Composition | Weight % |
| Tapioca starch | 5% | Tapioca starch | 72.78% |
| Glycerol | 1.8% | Glycerol | 26.20% |
| Acetic acid | 0.7% | Small molecules | 1.02% |
| Small molecules | 0.07% | | |
| Distilled water | 93.23% | | |
| Total | 100% | Total | 100% |

All dispersions were heated in a water bath (70° C.) for 15 min with stirring until completely gelatinized. An Ultrasonic Sonicator (Graymills Co., Chicago, Ill.) was used to remove air bubbles from the gelatinized solutions. The edible films were prepared by casting the solutions (107 g) into 10-inch radius Teflon plates. These were oven dried at 45±2° C. for 12 hours, then the dried films peeled off from the plate surfaces. The final concentration of each small molecule compound in the dry film was approximately 1% w/w. The film thicknesses were measured using a Magna-Mike 8500 Thickness Gage (Olympus, Japan), with resolution of 0.001 mm. A total of 5 measurements per film, at various locations were taken to determine the average thickness.

2.2.1.2 Film Moisture Content and Water Activity Testing.

The moisture content of the prepared films was determined by a gravimetric method. To accomplish this, the samples were dried at 105±2° C. in a laboratory oven (UNE PA, Memmert, Germany) until constant weight was achieved (Jiang et al., 2010). The tests were done by using approximately 1.0 g film samples that were previously conditioned for 24 hours at 23° C. and 50% relative humidity. These were placed in previously dried and cooled glass petri dish and kept in the oven for 8 hours. Weights of the samples were taken before and after drying using a 5 decimal point XSE Analytical Balance (±0.01 mg) (Mettler Toledo Co. Toledo, Ohio). All tests were conducted in triplicates and the average values were recorded.

As for water activity measurement, each sample (2.0 g) was placed into weighting scale, and their initial water activity was determined using a water activity meter (AquaLab®, Decagon Devices Inc., Pullman, Wash., USA).

2.2.1.3. Oxygen Permeation Testing.

Oxygen ($O_2$) permeability of the films was tested using an OX-TRAN® Model 2/21 Series OTR instrument (Mocon Inc., Minneapoils, Minn.). The method of oxygen permeability testing was done according to the ASTM D3985 method with some modifications. The oxygen transmission rates of the film samples were measured at 23° C. and 0% relative humidity. An Aluminum mask manufactured by Modern Controls Inc. (Minneapolis, Minn.) was placed on each film to make a test area of 5 $cm^2$. Tests were performed after 12 hours conditioning. Nitrogen carrier gas was used to purge the chamber of the diffusion cell while oxygen gas flowed over one side of the sample. The flow rate of the nitrogen carrier gas was 10 $cm^3$/min. Oxygen gas that permeated through the film into the nitrogen carrier gas was transported to the detector at the flow rate of 10 $cm^3$/min. An oxygen-sensitive coulometric sensor was used to measure the quantity of oxygen that permeated the material (ASTM, 2004). The results were obtained using a Model 34401A multimeter manufactured by Hewlett-Packard Company (Loveland, Colo.). Frequent calibration of the instrument was performed with a standard PET film sample obtained from Modern Control Inc. (Minneapolis, Minn.). Duplicate measurements on two pouches for each condition were obtained.

2.2.11 Water Vapor Permeation Testing.

The WVP tests were conducted using the ASTM E96 (1996) Method with some modifications. Test cups with 50 $cm^2$ open area were filled with 10 g anhydrous calcium sulfate to produce a relative humidity of 0% inside the cup. The film samples were placed on top of the cup and sealed with an O-ring. A high vacuum silicone sealant was applied between the O-ring and the film samples, between the sealing lip of the cup and the sample, before clamping them with 4 screws. The cups containing the desiccants were weighed to give the initial weight and then placed in a humidity chamber at room temperature (23±2° C.) and relative humidity of 55±2%. At an hour intervals the cups were weighed until a steady state was reached. The water vapor transmission rate (WVTR) through the film was estimated from the linear portion of the plot of weight gained versus time and the slope divided by the film exposure area according to Equation 3.2. Three replicates per film were tested. The WVP of the film was calculated by multiplying the WVTR by the film's thickness and dividing saturated by the vapor pressure difference across the film and surface area of the sample exposed to the storage environment.

(Equation 3.3)

$$WVTR = \frac{Q}{t} \tag{3.2}$$

$$WVPC = WVTR \times \frac{T}{A \times \Delta P}. \tag{3.3}$$

Where: A is the surface area ($m^2$) of the sample exposed to moisture;

$\Delta P$ is the driving force, describing the humidity difference between two sides of film (Pa). In this test, Relative Humidity (RH) was determined by measuring dry bulb and wet bulb temperature during the tests and RH value was obtained by using Psychometric Chart. The driving force $\Delta P$ was based on Saturation Pressure of Water Vapor, which was corresponding to dry bulb temperature during the test. In this case, water vapor saturation pressure was $7.30 \times 10^3$ Pa according to Saturation Pressure & Temperature Chart.

T is thickness of the film (m);

Q is weight change of WVT cups (g)

t is period of time (day)

All tests were conducted in triplicate and the units for WVPC were $g \times m^{-1} \times s^{-1} \times Pa^{-1}$.

3.3.3 Thermal analysis By Differential Scanning Calorimetry (DSC)

A TA instrument (Q2000, USA) differential scanning calorimeter equipped with a data collection station was used to scan the thermal transitions of the tested films. The samples were weighed (ranging from 5 to 7 mg) using a 5 decimal point XSE Analytical Balance (±0.01 mg) (Mettler Toledo Co. Toledo, Ohio) in aluminum pans followed by sealing with inverted lids, for optimum thermal conductivity. The reference was an empty aluminum pan sealed in the same manner. Both pans were then equilibrated at 20° C. for 30 sec to stabilize the baseline followed by scanning until 200° C. at a heating rate of 10° C. $min^{-1}$. Thermograms were recorded and analyzed by the TA Instrument software (Universal Analysis 2000, Version 4.1D). The $T_m$ (Melting temperature) was identified as the inflexion point of the baseline. Three replicates per film were tested.

3.3.4 X-ray Diffraction Analysis

X-ray diffraction was measured using a Rigaku Miniflex 600 diffractometer with vertical goniometer was used (Cu K$\alpha$ radiation $\lambda$=1.542 Π). Operation was performed at 40 kV and 20 mA. All samples were mounted on a glass and were attached to the equipment holder and the X-ray intensities were recorded with a scintillation counter in a scattering angel (2θ) range of 3-50° with a scanning speed of 1°/min. Distances between the planes of the crystals d(II) where calculated from the diffraction angels (°) obtained in the X-ray pattern, according to Bragg's law:

$$n\lambda = 2d \sin(\theta) \qquad (3.4)$$

Where λ is the wavelength of the X-ray bean and n is the order of reflection.

From the scattering spectrum, the effective percent crystallinity of films was determined, according to Hermans and Weidinger (1961), as the ratio of the integrated crystalline intensity to the total intensity. Crystalline area was evaluated on the basis of the area of the main peaks. Due to the complexity of the system, the calculated crystallinities are not taken as absolute value, but are rather used for comparative purposes.

3.3.5 Mechanical testing by Dynamic Mechanical Analysis (DMA)

The mechanical properties of the films were determined using a stress-controlled Dynamic-Mechanical Analyzer (DMA 2980, TA Instruments, Surrey, England) at a frequency of 1 Hz from −80 to 100° C. with a heating rate of 5° C. min$^{-1}$. Film samples (25 mm in length, 5 mm in width, and 6-8 mil in thickness) were equilibrated at room temperature (23±2° C.) and relative humidity of 55±2% for 48 hours prior to the analysis. The storage ('E) and loss modulus ("E) as well as tan δ of the film samples were monitored as a function of temperature. Three replicates per film were tested.

2.3. Statistical Analysis

All data were analyzed using the analysis of variance (ANOVA), and Tukey's multiple comparisons test was used to determine the significant differences between the means at a level of p<0.05. The statistical analysis was used to compare and determine the significant effect of the addition of JA-144, TH-4, TH-8 on the thickness, moisture content, and the mechanical and barrier properties of the tapioca films. SPSS Version 10.0 software (SPSS Inc., Chicago, Ill.) was used for this purpose. Data are presented as mean and standard deviation of duplicate or triplicate analysis.

4. Results and Discussion 3.2 Thickness, Moisture Content and Water Activity

The thickness of the films was average from 5 readings taken from 5 random places on the films. Results are shown in Table 7. The film thicknesses ranged from 0.171±0.006 mm for the TH-4 films to 0.198±0.004 mm for JA-144 films. The thickness of the films did not significantly (p>0.05) increased after the addition of TH-4 and TH-8. However, it significantly (p<0.05) increased after the addition of JA-144 when compared with the control film.

TABLE 7

A Summary of Thicknesses, Moisture Contents and Water Activity of Tapioca films with JA-144, TH-4 or TH-8.

| Sample ID | Compound conc. % | Thickness[1] (mm) | Standard Deviation | Moisture Content[2] (%) | Standard Deviation | Water Activity |
|---|---|---|---|---|---|---|
| Control | 0 | 0.173$^a$ | 0.005 | 12.900$^a$ | 0.210 | 0.266 |
| JA-144 | 1 | 0.198$^b$ | 0.004 | 16.021$^b$ | 0.664 | 0.270 |
| TH-4 | 1 | 0.170$^a$ | 0.006 | 10.183$^c$ | 0.107 | 0.252 |
| TH-8 | 1 | 0.172$^a$ | 0.005 | 9.824$^c$ | 0.100 | 0.259 |

[1]Each data point is expressed as the mean of five measurements

[2]Each data point is expressed as the mean of three measurements $^{a-c}$In a given column, values with same letters are not significantly different (p > 0.05), while different letters are significantly different (p < 0.05).

Figure 25A:
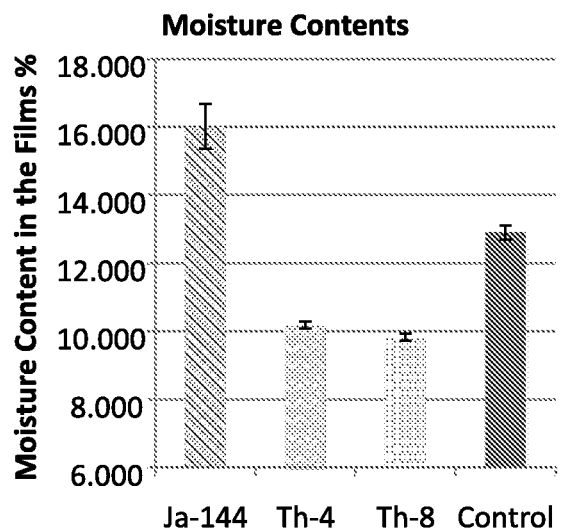
FIGS. 25A and B are graphs showing moisture content (A) and water activity (B) of tapioca films with JA-144, TH-4 or TH-8.
Figure 25B:
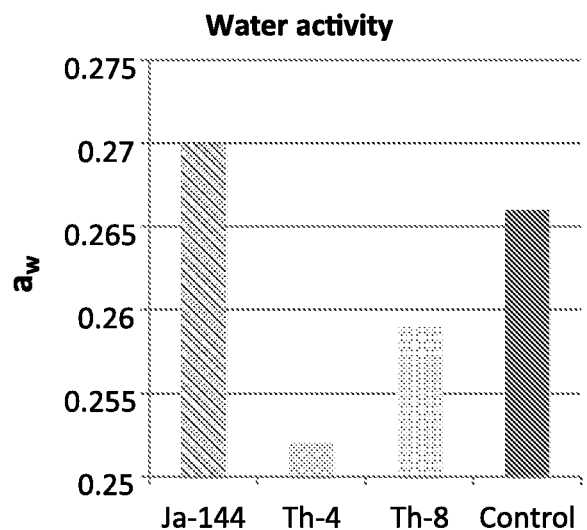

The moisture content and water activity of the Tapioca films with and without JA-144, TH-4, TH-8 (FIG. 25) were measured and are also shown in Table 7, and FIG. 17. From the results obtained, the JA-144 film had the highest moisture content value and water activity of 16.021±0.664%, 0.270.

3.4.2 Water Vapor Permeability.

Figure 26:
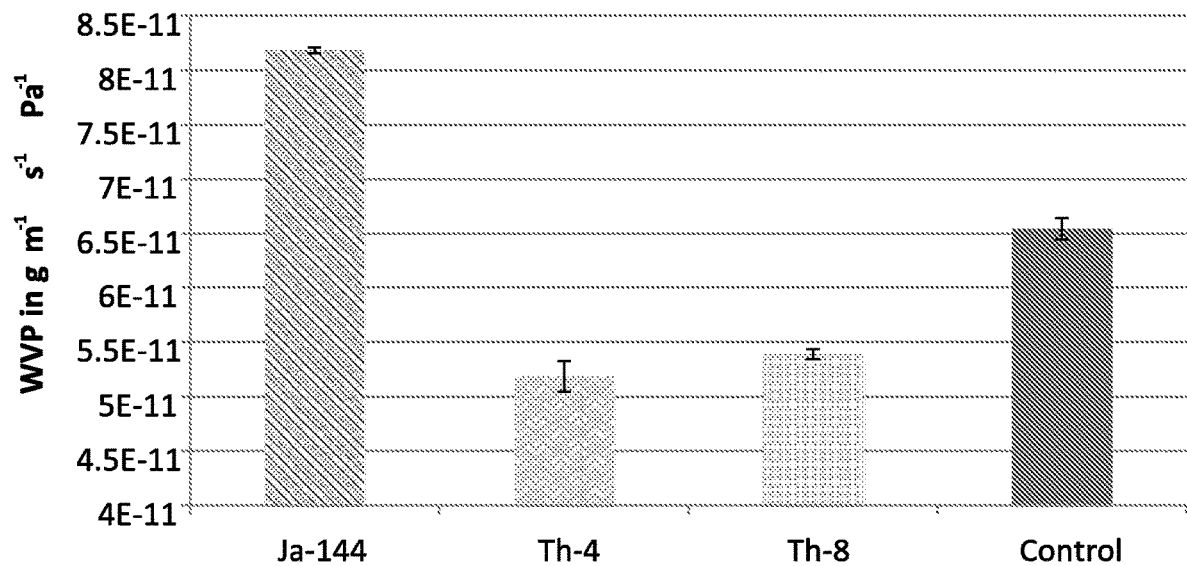
FIG. 26 is a graph showing water vapor permeability for tapioca films with JA-144, TH-4 or TH-8.

The water vapor permeabilities of the films are shown in Table 8 and FIG. 26. As can be seen from the results, the WVP of the tapioca film without compound was $6.546 \times 10^{-11} \pm 9.688 \times 10^{-13}$ g×m$^{-1}$×s$^{-1}$×Pa$^{-1}$. The JA-144, TH-4, and TH-8 films produced WVP values of $8.183 \times 10^{-11} \pm 2.752 \times 10^{-13}$, $5.186 \times 10^{-11} \pm 1.386 \times 10^{-12}$, $5.389 \times 10^{-11} \pm 4.636 \times 10^{-13}$ g×m$^{-1}$×s$^{-1}$×Pa$^{-1}$, respectively. The WVP of the films was significantly decreased (p<0.05) after the addition of TH-4 and TH-8. However, it was significantly increase (p<0.05) after the addition of JA-144 compared with the control group.

TABLE 8

The summary of WVP calculations for Tapioca
Films with JA-144, TH-4 or TH-8

| Sample ID | OTR (cc × m$^{-2}$ × s$^{-1}$) | Permeant Conc. (%) | OPC$^1$ (cc × m$^{-1}$ × s$^{-1}$ × Pa$^{-1}$) | Standard Deviation |
|---|---|---|---|---|
| Control | 1.519 × 10$^{-5}$ | 21 | 8.564 × 10$^{-14a}$ | 3.489 × 10$^{-15}$ |
| JA-144 | 1.470 × 10$^{-5}$ | 21 | 1.084 × 10$^{-13b}$ | 2.708 × 10$^{-15}$ |
| TH-4 | 1.241 × 10$^{-5}$ | 21 | 7.406 × 10$^{-14c}$ | 4.206 × 10$^{-15}$ |
| TH-8 | 1.195 × 10$^{-5}$ | 21 | 8.310 × 10$^{-14a}$ | 1.247 × 10$^{-15}$ |

3.3.6 Oxygen Permeability Coefficient.

Figure 27:
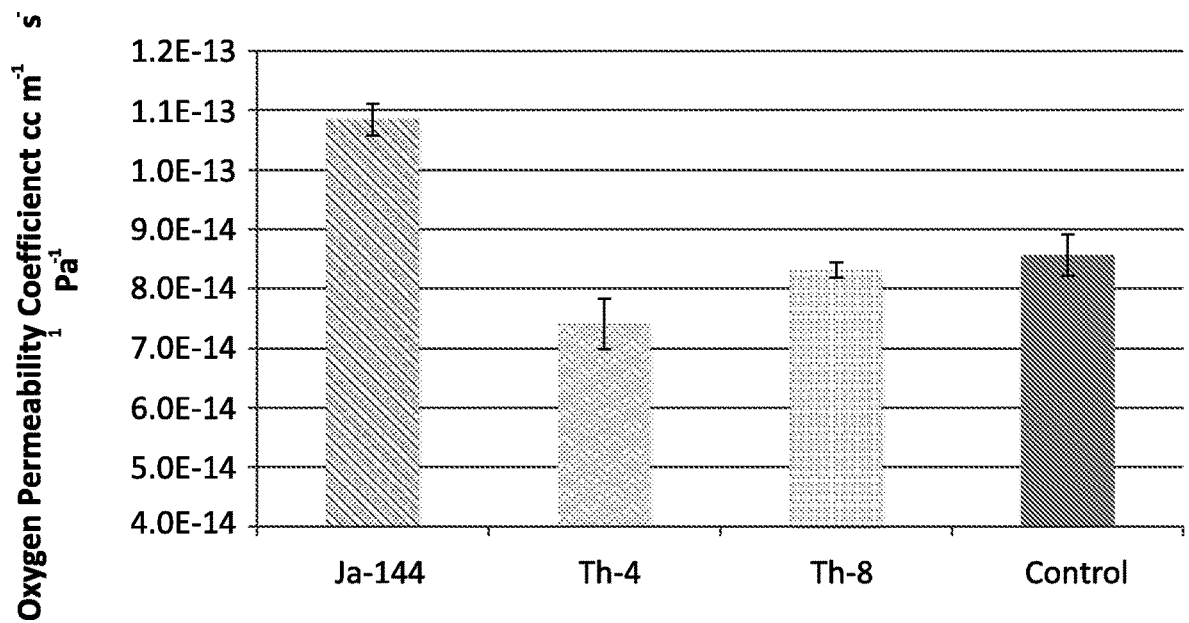
FIG. 27 is a graph showing oxygen permeability coefficient for tapioca starch with JA-144, TH-4 or TH-8.

The Oxygen Permeability Coefficients (OPC) of the films are shown in Table 9 and FIG. 27. As can be seen from the results, the OPC of the tapioca film without compound was 8.564×10$^{-14}$±3.469×10$^{-15}$ cc×m$^{-1}$×s$^{-1}$×Pa$^{-1}$. The JA-144, TH-4, and TH-8 films produced OPC values of 1.084×10$^{-13}$±2.708×10$^{-15}$, 7.406×10$^{-14}$±4.206×10$^{-15}$, 8.310×10$^{-14}$±1.247×10$^{-15}$ cc×m$^{-1}$×s$^{-1}$×Pa$^{-1}$, respectively. The OPC of the films did not significantly decreased (p<0.05) after the addition of TH-8. However, it was significantly increased (p<0.05) after the addition of JA-144 or decreased on the addition of TH-4 and TH-8 when compared with control group.

TABLE 9

The Summary of OPC calculations for Tapioca
Films with JA-144, TH-4 or TH-8.

| Sample ID | WVTR (g/s) | Relative Humidity$^1$ (%) | ΔP (Pa) | WVP$^1$ (g × m$^{-1}$ × s$^{-1}$ × Pa$^{-1}$) | Standard Deviation |
|---|---|---|---|---|---|
| JA-144 | 8.344 × 10$^{-6}$ | 56.9 | 4.15 × 10$^3$ | 8.183 × 10$^{-11a}$ | 2.752 × 10$^{-13}$ |
| TH-4 | 5.962 × 10$^{-6}$ | 56.9 | 4.15 × 10$^3$ | 5.186 × 10$^{-11b}$ | 1.386 × 10$^{-12}$ |
| TH-8 | 6.323 × 10$^{-6}$ | 56.9 | 4.15 × 10$^3$ | 5.389 × 10$^{-11b}$ | 4.636 × 10$^{-13}$ |
| Control | 7.708 × 10$^{-6}$ | 56.9 | 4.15 × 10$^3$ | 6.546 × 10$^{-11c}$ | 9.688 × 10$^{-13}$ |

$^1$Each data was expressed as the mean of three measurements.
$^{a-c}$In a given column, values with same letters are not significantly different (p > 0.05), while different letters are significantly different (p < 0.05).

3.3.7 Thermal Analysis by Differential Scanning Calorimetry

Figure 28:
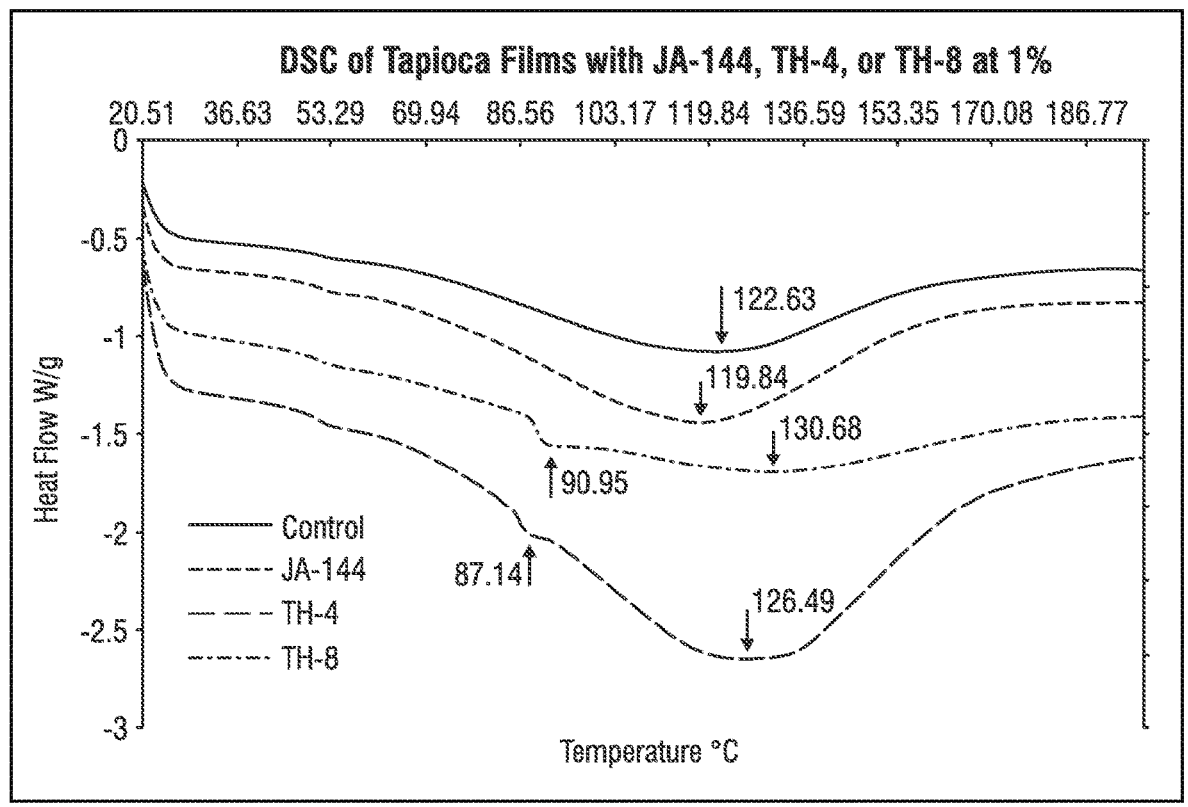
FIG. 28 is a graph showing differential scanning calorimetry of tapioca films with JA-144, TH-4 or TH-8 at 1%

The differential Scanning calorimetric curves in FIG. 28 display the thermally induced endothermic transitions for JA-144, TH-4 and TH-8 tapioca films from 20° C. to 200° C. As shown in FIG. 28, the melting temperature (T$_m$) of the control, JA-144, TH-4 and TH-8 films were 122.63° C., 119.84° C., 130.68° C., and 126.49° C., respectively. Both the control and JA-144 films exhibited a single endothermic peak, which indicated homogeneity of the films. This is an indication that JA-144 blended well within the molecular structure of the starch. For the TH-4 or TH-8 films, an extra small peak was observed at 87.14° C. or 90.95° C., respectively, suggested that TH-4 or TH-8 was not completely incorporated into the molecular structure of the starch film. The results also reflected that the addition of JA-144, TH-4, and TH-8 caused a shift in the T$_m$, indicated the film's crystallinity was affected by the compounds. In addition, a broadening of the peaks when the compounds were added to the starch is an indication of increased variability of the crystals within the molecular structure of the starch.

3.3.8 X-ray Diffraction Pattern

The X-ray patterns of Tapioca film only, or with 1% w/w JA-144, TH-4, or TH-8 films were presented in FIG. 296. The main peak positions of each sample were summarized in Table 10.

TABLE 10

The position of main X-ray diffraction peaks
of Tapioca Films with JA-144, TH-4 or TH-8

| Sample ID | Peak Position) | | | | | | |
|---|---|---|---|---|---|---|---|
| Control | 3.80 | 7.60 | 11.39 | 38.70 | 7.20 | 21.20 | 28.54 | 19.43 |
| JA-144 | 3.80 | 7.60 | 11.39 | 38.70 | | 21.20 | 28.54 | 19.43 |
| TH-4 | 3.80 | | 11.39 | 38.70 | | | | |
| TH-8 | 3.80 | 7.60 | 11.39 | 38.70 | | 21.20 | 28.54 | |

Figure 29:
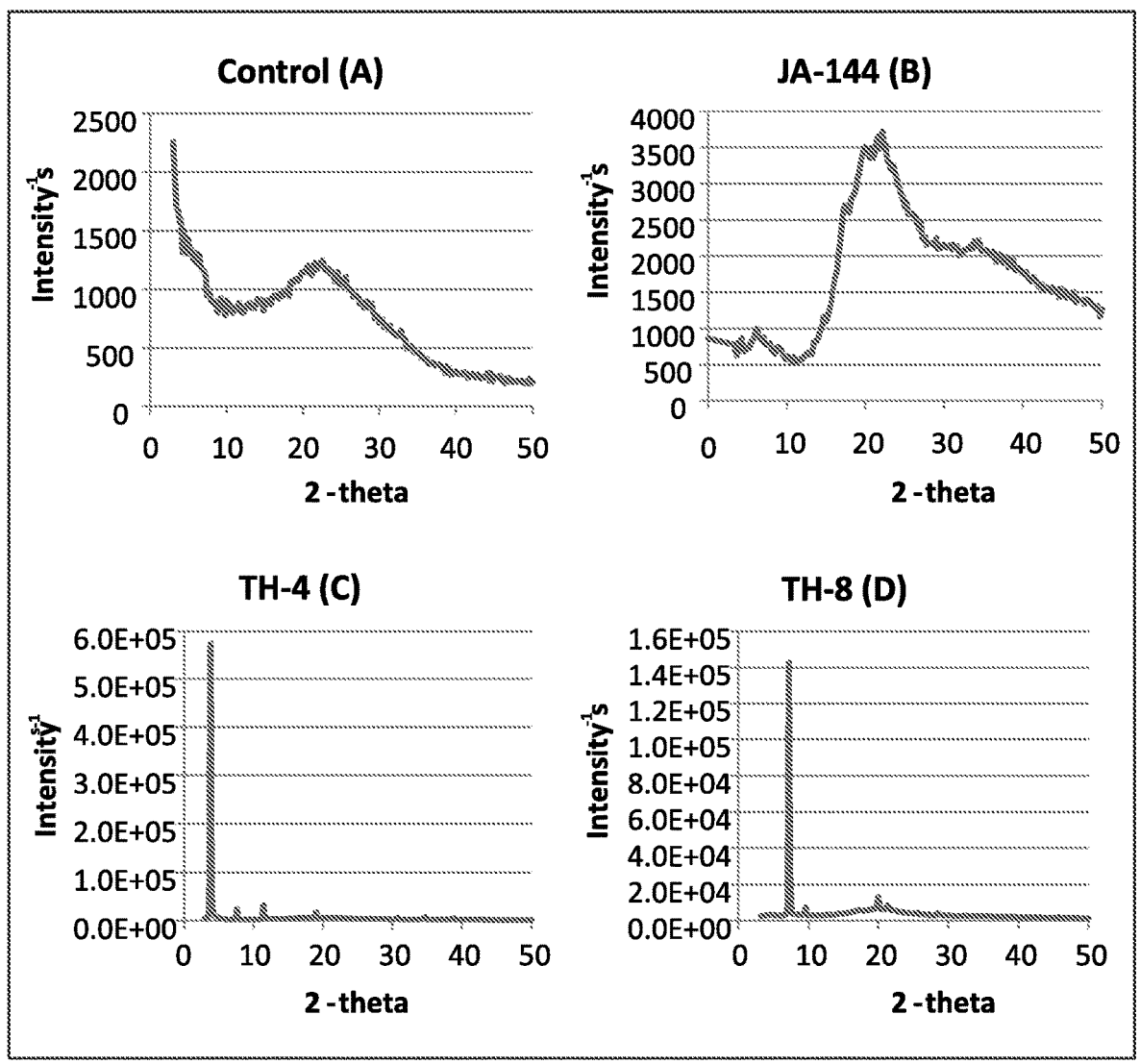
FIGS. 29A-D are graphs showing X-ray diffraction of tapioca films with JA-144, TH-4 or TH-8.

As shown in FIG. 29, all the samples showed different extent of crystallinity. The Tapioca film matrix was mostly amorphous in nature with one diffuse peak located at 21.20° and other small crystalline fraction imbedded in the amorphous matrix as indicated by small hump at various locations. By adding JA-144 into the film, it was showed that the intensity of main diffuse peak at 21.20° increased, and one of the small peaks (7.20° disappeared. By adding TH-4 into the film, the X-ray pattern was apparently changed. It was showed that a strong peak appeared at 3.80° and most of the small peaks disappeared. The same pattern was observed on TH-8 film. It was showed that a strong peak appeared at 7.60° and some of the small peaks disappeared, respectively.

3.3.9 Mechanical testing by Dynamic Mechanical Analysis (DMA)

Figure 30:
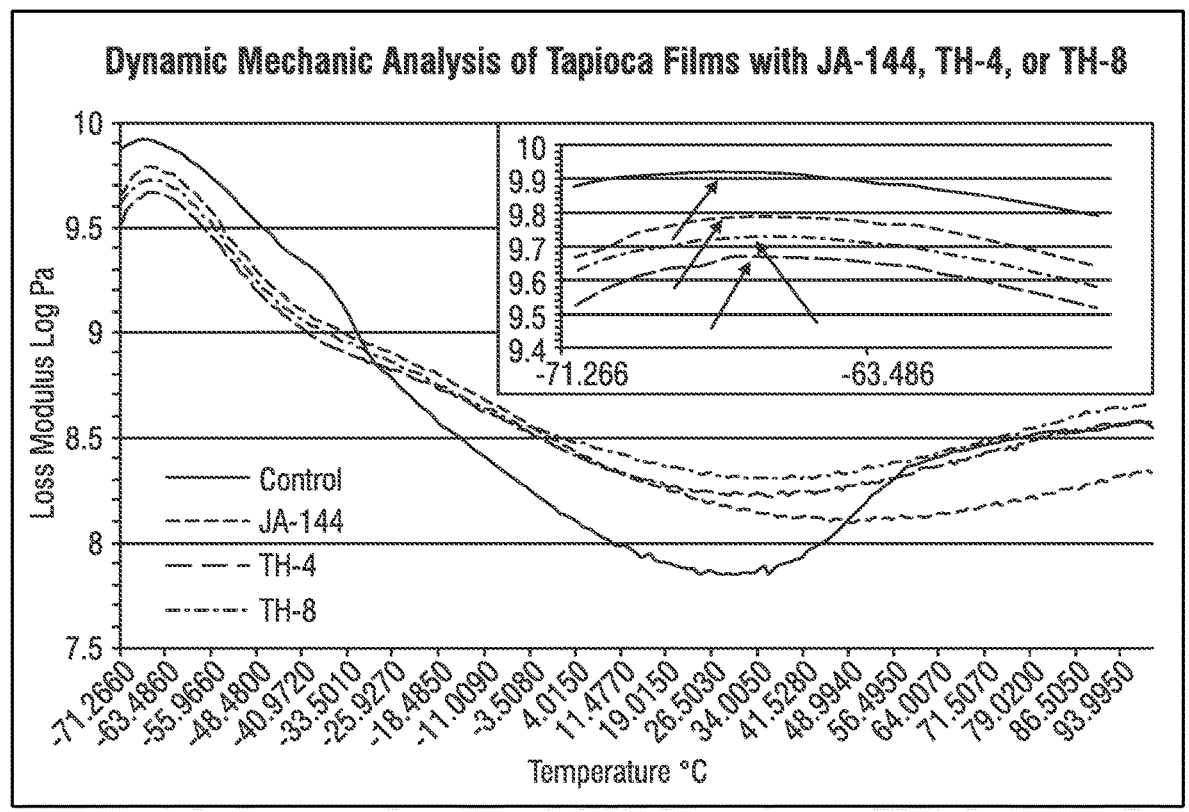
FIG. 30 is a graph showing the effect of JA-144, TH-4 or TH-8 on the storage modulus of tapioca films.

In Dynamic Mechanical Analysis (DMA) experiments, information on the storage modulus, loss modulus and tan δ of the tapioca films with JA-144, TH-4, and TH-8 were obtained. The data were used to determine glass transition temperature T$_g$ as well as the stress-strain curve as a function of time. By definition, temperature corresponding to a sharp decrease in storage modulus, or a maximum value of loss modulus and tan δ during a temperature sweep is the glass transition temperature (Sperling, 2001). Storage modulus provides important information of film's ability to store energy in response to an applied force at given temperatures. It is also called elastic modulus and relates to the inherent stiffness of the sample. FIG. 30 shows the effects of JA-144, TH-4, TH-8 addition on the storage modulus over the entire temperature range of the DMA. The data show that the addition of JA-144, TH-4, and TH-8 had significant effects (p<0.05) on the modulus of the test films. Particularly, the addition of JA-144 decreased the storage modulus at temperature above −57° C., while the addition of TH-4 or TH-8 significantly increased storage modulus at temperatures above −14° C., as shown in FIG. 30.

Figure 31:
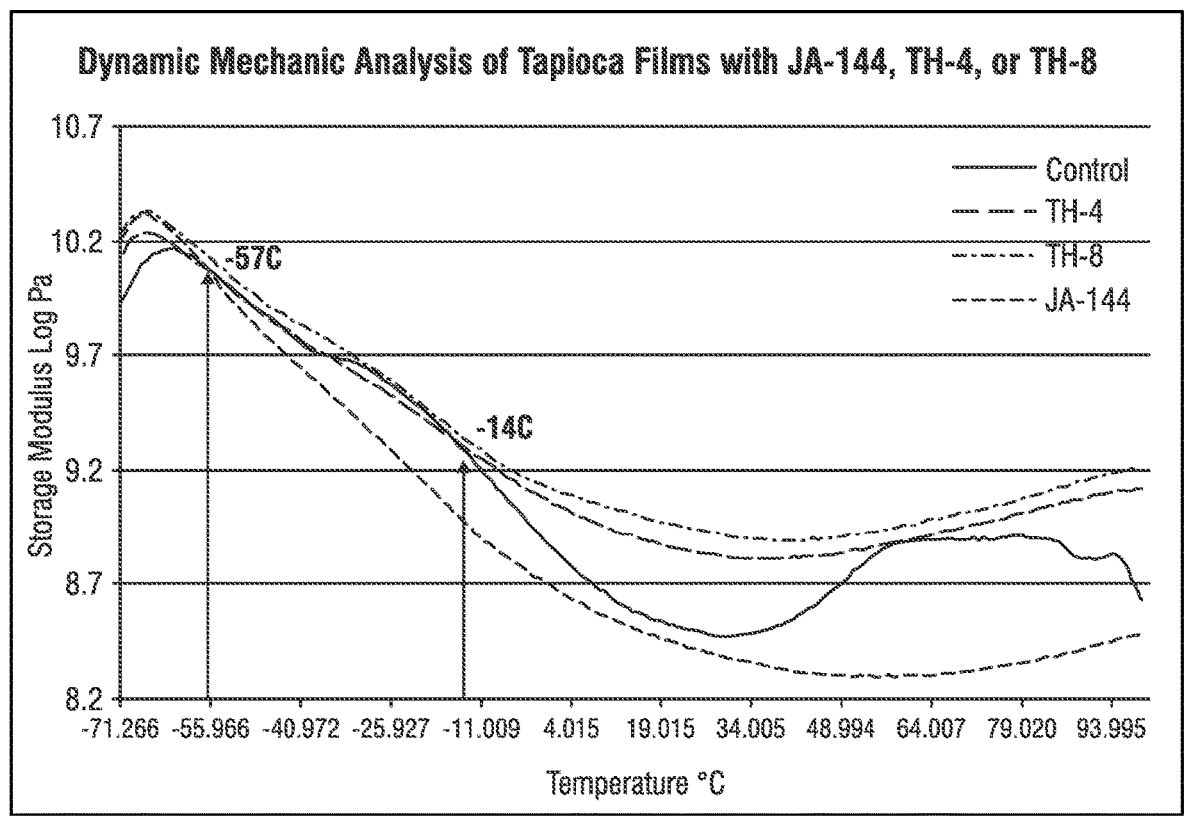
FIG. 31 is a graph showing loss modulus of tapioca films with JA-144, TH-4 or TH-8.
Figure 32:
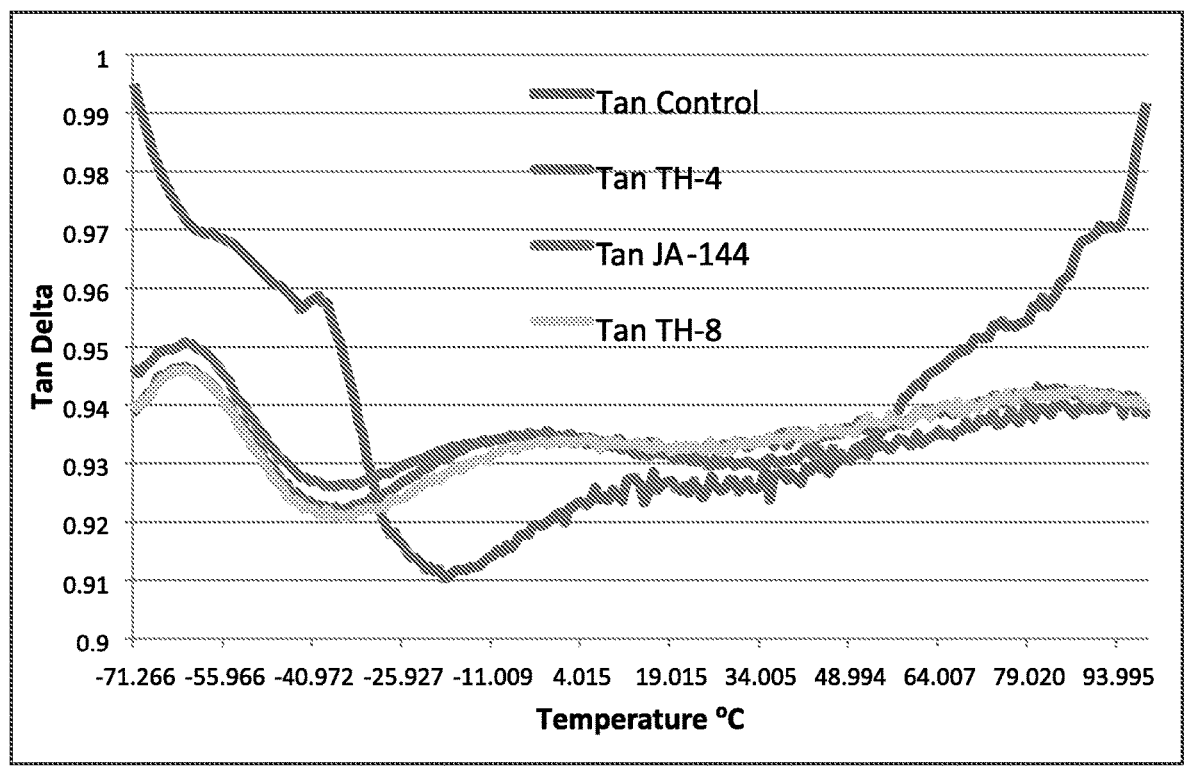
FIG. 32 is a graph showing Tan Delta of tapioca films with JA-144, TH-4 or TH-8.

The results shown in FIGS. 31 and 32 were used to determine the effect of JA-144, TH-4, or TH-8 on the loss modulus and tan δ of the films. From this information the T$_g$ for the films were determined, which was estimated to be −67.249° C. and −67.249° C., respectively. As for TH-4 and TH-8 film, $T_g$ values were the highest, which were −66.508° C. and −66.508° C., respectively.

3.4 Discussion

3.5.1 Thickness, Moisture Content, Water Activity, and barrier properties (OPC, WVP)

The results showed that thicknesses of the films did not significantly increased after the addition of TH-4 and TH-8. However, it was significantly increased after the addition of JA-144 compared with control group. The thickness increase caused by JA-144 was possibly due to the hydroxyl groups in the compound and its hydrogen bonding to the polymeric chains (Lagos et al., 2015). The existence of hydroxyl group in JA-144 also played a key role in film's moisture content and water activity due to its hygroscopic character. This interaction with the film's matrix increased the spaces between the chains, thus facilitating water migration into the film, and consequently, increasing its moisture content and water activity (da Matta, et al., 2011). These structural changes within the JA-144 films further affected their barrier properties, which are shown in the WVP and OPC tests. As shown in Table 8 and Table 9, the WVP and OPC of JA-144 are $8.183\times10^{-11}$ g$\times$m$^{-1}\times$s$^{-1}\times$Pa$^{-1}$, $1.084\times10^{-13}$ cc$\times$m$^{-1}\times$s$^{-1}\times$Pa$^{-1}$, respectively, which are 25.00% and 26.58% higher than the control film. (Chien-Hsien, et al., 2007).

As for TH-4 and TH-8 films, the results indicate that there was no significant change in thickness, and they had lower moisture content and water activity, but good water and oxygen barrier properties. These could be attributed to the sulfonamide functional group in TH-4 and TH-8. The sulfonamide functional group is rigid, hydrophobic, and typically has a tendency toward crystallization (Seong et al., 2001). These characters of sulfonamide functional group in TH-4 and TH-8 could probably enhance the crosslinking effect within the film matrix, and consequently lead to less moisture content, less water activity, but good oxygen and water barrier properties.

3.5.2 Mechanical and Thermal Properties

As discussed previously, JA-144 film showed hydrophilic characteristics, while TH-4 and TH-8 films were hydrophobic, rigid, and had a tendency toward crystallization due to the sulfonamide functional group. Therefore, it is expected that JA-144 film should have lower $T_g$, lower $T_m$, and less storage modulus due to its low crystallinity, higher amorphous, and high flexibility characteristics compared to the control film. As for TH-4 and TH-8 films, it is expected that they should show a higher $T_g$, higher $T_m$, and more storage modulus due to the presence of halogens in their structure. These have a tendency to increase crosslinking and subsequently increase the crystallinity of the polymer (Jianwei et al., 2005).

These expectations were proved by the DSC, X-ray diffraction and DMA tests. The $T_m$ of JA-144 was 119.84° C., which is 2.28% lower than that of the control; while for TH-4 and TH-8 films, they are 3.15% and 6.56% higher than the control, respectively. The storage modulus reflected the stiffness of film, showed a value −57° C. for JA-144 film, and this was lower than the control film. For the TH-4 and TH-8 films, higher storage modulus values were expected and the results show that these values were significantly higher than the control film (above −11° C.), as shown in FIG. 30.

Figure 3:
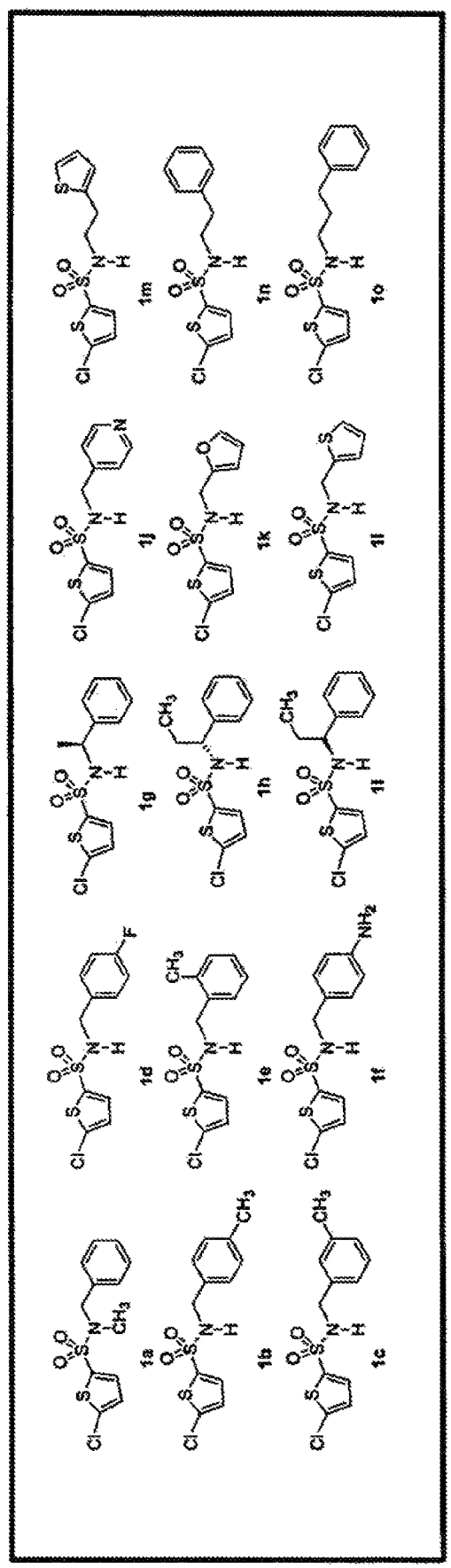
FIG. 3 is a graphic showing synthesized analogues of compound 1.
Figure 4:
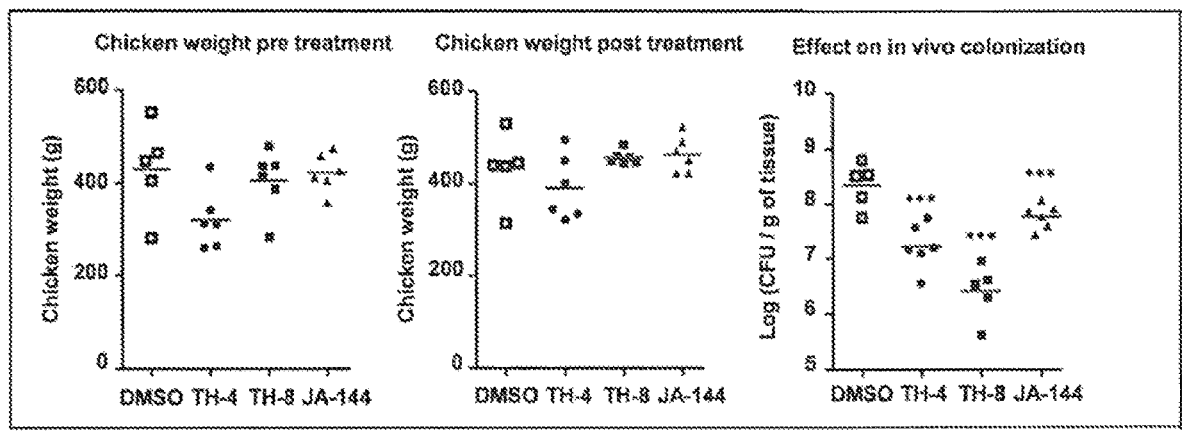
FIG. 4 are graphs showing in vivo effect of TH-4 and TH-8 on *C. jejuni* colonization in three week old broiler chickens. JA-144, another resynthesized compound had broad spectrum effect on other bacteria including *E. coli* and *Listeria*.

X-ray diffraction tests further detect these minor changes. As shown in FIG. 3.5, the addition of JA-144 resulted in a slightly increase of crystallinity. This could be due to the intra-molecular interactions of hydroxyl groups between amylose and JA-144 that led to the formation of intramolecular hydrogen bonding. No extra peaks were observed indicated that JA-144 was well blended. However, the addition of TH-4 and TH-8 resulted in a dramatic increase of crystallinity. X-ray patterns for these two were significantly changed, which could be ascribed to two possibilities. First, it is possible that crosslinking effect between TH-4/TH-8 and starch amylose were formed when adding TH-4/TH-8 into film forming solution. Crosslinking restricts molecular mobility, tying the polymer backbones together thus results in crystallinity increase (Shulamit et al., 2008). Second, it is possible that TH-4/TH-8 molecules are not well blended into the film. Previous research demonstrated that sulfonamide group is rigid, hydrophobic, and typically has a tendency toward crystallization (Seong et al., 2001). Since the film forming solution is hydrophilic, it is possible that these TH-4/TH-8 molecules were self-assembled or aggregated during the blending process (Kazunari et al., 1992). As a result, a high intensity peak shown in X-ray diffraction was observed.

Figure 33:
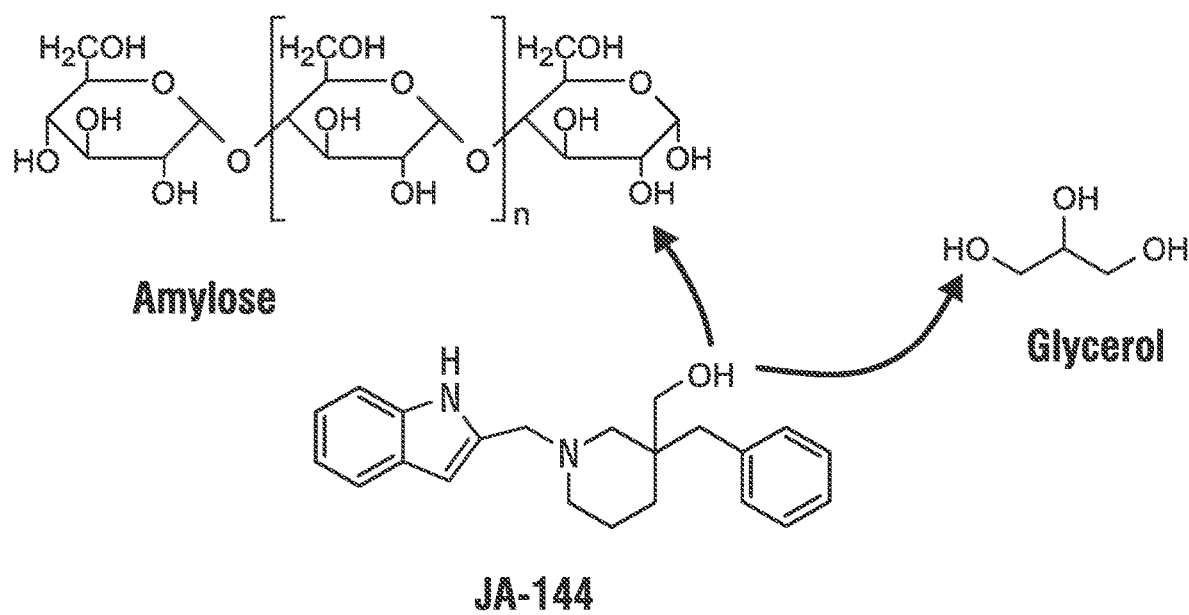
FIG. 33 is a graphic showing possible mechanism of JA-144 binding to amylose or glycerol.

An ideal edible film with incorporated compounds for antimicrobial application should have less moisture content, good barrier properties, and good mechanical properties (Bhanu et al., 2015). Based on these criteria, JA-144 film showed high moisture content, high OPC and WVP, which means low barrier properties, but good mechanical properties due to the plasticizing and co-plasticizing effect of hydroxyl group with water molecules. This means that the JA-144 films will dissolve faster in the mouth and needs less chewing since it showed a lower mechanical strength and higher moisture holding capacity. A possible mechanism of JA-144 binding to amylose or glycerol is shown in FIG. 33. As for TH-4 and TH-8 films, they showed less moisture content, low OPC and WVP, which means good barrier properties, but low mechanical strength due to the crosslinking effect of sulfonamide group. This means the TH-4 and TH-8 films show better characteristics for applications such as packaging and wrapping, which require more mechanical strength and less gas permeability. Also, these compounds were not completely incorporated into the film as both DSC curves showed an extra peak at 87.14° C. and 90.95° C. Consequently, future work should be focused on how to optimize the structure of these molecules, or to introduce another chelating agent to offset drawbacks of each compound. By doing so, it is to be expected that these compounds could be better incorporated into the film.

REFERENCES

Arun, A., Amrish, C., Vijay, S., Kamla, P., 2010. Fast Dissolving Oral Films: An Innovative Drug Delivery System and Dosage Form. Internat J. Chem Tech Research. 2(1): 576-583.

Blaser, B., Engberg, J. 2008. Clinical aspects of *Campylobacter jejuni* and *Campylobacter coli* infections. In I. Nachamkin, C. M. Szymanski, and M. J. Blaser, (Eds.), Campylobacter. American Society for Microbiology, Washington, D.C., pp. 99-121.

Bochner, B. R., Savageau, M. A., 1977. Generalized indicator plate for genetic, metabolic, and taxonomic studies with microorganisms. Appl Environ Microbiol. 33: 434-444.

CDC. 2014. Incidence and Trends of Infection with Pathogens Transmitted Commonly Through Food—Foodborne Diseases Active Surveillance Network, 10 U.S. Sites, 2006-2013. MMWR Morb Mortal Wkly Rep. 63(15): 328-332.

Christina L. L., Caelli C. C., Andre G. S. 2014. Mass and Density Measurements of Live and Dead Gram-Negative and Gram-Positive Bacterial Populations. Appl Environ Microbiol. 80(12): 3622-3631.

Coker, A. O., R. D. Isokpehi, B. N. Thomas, K. O. Amisu, and C. L. Obi. 2002. Human campylobacteriosis in developing countries. Emerging infectious diseases. 8:237-244.

Diane, J. W. B., Speece, R. E. 1991. A database of Chemical Toxicity to Environmental Bacteria and Its Use in Interspecies Comparisons and Correlations. Research Journal of the Water Pollution Control Federation. 63(3): 198-207.

Eidus, L., Diena, B. B., Greenberg, L., 1959. Observations on the use of tetrazolium salts in the vital staining of bacteria. Canadian J. Microbiol. 5: 245-250.

Han, J. H., 2000. Antimicrobialfood packaging. Food Technology 54:56-65.

Jongbloed, J. D., Grieger, U., Antelmann, H., Hecker, M., Nijland, R., Bron, S., and van Dijl, J. M. (2004) Two minimal Tat translocases in Bacillus. Mol Microbiol. 54: 1319-1325.

Moore, J. E., M. D. Barton, I. S. Blair, D. Corcoran, J. S. Dooley, S. Fanning, I. Kempf, A. J. Lastovica, C. J. Lowery, M. Matsuda, D. A. McDowell, A. McMahon, B. C. Millar, J. R. Rao, P. J. Rooney, B. S. Seal, W. J. Snelling, and O. Tolba. 2006. The epidemiology of antibiotic resistance in Campylobacter. Microbes and infection/Institut Pasteur. 8:1955-1966.

Mosen A. 2005. Environmental Concerns of a Beet-Sugar Factory. In A. Mosen (Ed.), Beet-Sugar Handbook. John Wiley & Sons, Inc., Hoboken, N.J., pp. 563-598. Mo6-A2. 2006. Clinical and Laboratory Standard Institute. Protocols for evaluating dehydrated Mueller Hinton agar. Approved Standard M6-A2 $2^{nd}$ Ed. CLIS. Wayne, Pa. Robertson, G. L. 2006. Active and intelligent packaging. In Food Packaging: Principles an d Practice, $2^{nd}$ ed. CRC Press, Boca Raton, Fla., pp. 285-311.

Han, J. H., 2003. Antimicrobialfood packaging. In A. Raija (Ed.), Novel Food Packaging Techniques. CRC Press, Boca Raton, Fla., pp. 50-65.

Rotunda, A. M., Jones, D. H., 2010, HIV-associated lipohypertrophy(buccal fat-pad lipoma-like lesions) reduced with subcutaneously injected sodium deoxycholate. Dermatol Surg. 36: 1348-1354.

Sawer, I. K., Berry, M. I., Ford, J. L. 1997. Effect of medium composition, agitation and the presence of EDTA on the antimicrobialactivity of cryptolepine. Letters Appl Microbiol. 25(3): 207-11.

Du, W., Avena-Bustillos, R. J, Hua, S. S. T, McHugh, T. H. 2015. Antimicrobialvolatile essential oils in edible films for food safety. In A. Méndez-Vilas (Ed.), Science Against Microbial Pathogens: Communicating Current Research and Technological Advances. pp. 1124-1134.

Anker, M., Berntsen, J., Hermansson, A. M., Stading, M. 2001. Improved water vapour barrier of whey protein films by addition of an acetylated monoglyceride. Innovative Food Science and Emerging Technologies. 3: 81-92.

Bhanu, M., Mu, K., Harsha, K. 2015. Antimicrobialfood packaging: potential and pitfalls. Frontiers in Microbiology. 6: 611-619.

Chien-Hsien, C., Lih-Shiuh, L. 2008. Mechanical and water vapor barrier properties of tapioca starch/decolorized hsian-tsao leaf gum films in the presence of plasticizer. Food Hydrocolloids. 22: 1584-1595.

da Matta, M. D., Jr., Sarmento, S. B. S., Sarantopoulos, C. I. G. L., Zocchi, S. S. 2011. Barrier properties of films of pea starch associated with xanthan gum and glycerol. Polimeros-Ciencia e Tecnologia. 21(1): 67-72.

FAO (Food and Agriculture Organization). 2004. Proceedings of the Validation Forum on the Global Cassava Development Strategy. In FAO (Ed), Global Cassava Market Study Business Opportunities for the Use of Cassava. International Fund for Agricultural Development, Roma, Italia. Vol. 6.

Fernández Cervera, M., Karjalainen, M., Airaksinen, S., Rantanen, J., Krogars, K., Heinämäki, J., Iraizoz Colarte, A., Yliruusi, J. 2004. Physical stability and moisture sorption of aqueous chitosan—amylose starch films plasticized with polyols. European Journal of Pharmaceutics and Biopharmaceutics. 58: 69-76.

Garcia, M., Martino, M., Zaritizky, N. 2000. Lipid addition to improve barrier properties of edible starch-based films and coatings. J. Food Sci. 65(6): 941-947.

Hermans, P. H., Weidinger, A. 1961. On the determination of the crystalline fraction of poly-ethylenes from X-ray diffraction. Makromolecular Chemistry. 44-46: 24-36.

Islam, M., Chen, J., Doyle, M. P., Chinnan, M. 2002. Control of Listeria monocytogenes on turkey frankfurters by generally-recognized-as-safe preservatives. J. Food Prot. 65: 1411-1416.

Jeannine, B. L., Nívea, M. V., Rodolfo, M. C., Dos, S., Ana-Monica, Q. B., Paulo, J. A. 2015. Mechanical properties of cassava starch films as affected by different plasticizers and different relative humidity conditions. International Journal of Food Studies. 4: 116-125.

Jianwei, X., Xueming, L., Tingling, L., Junchao, H., Chaobin, H. 2005. Synthesis and Self-Assembly of Di-functional Halogen-Bonding Molecules: A New Family of Supramolecular Liquid-Crystalline Polymers. Macromolecules. 38: 3554-3557.

Kazunari, A., Shigeru, D., Nobuhiro, M., Shigehiko, Y., Junzo, S. 1992. Self-Aggregates of Hydrophobized Polysaccharides in Water Formation and Characteristics of Nanoparticles. Macromolecules. 26(12): 3062-3068.

Kester, J. J., Fennema, O. R. 1986. Edible films and coatings: a review. Food Technology. 12: 47-59.

Lahellec, C., Fung, D. Y., Cunningham, F. E. 1981. Growth effect of sorbate and selected antioxidants on toxigenic strains of Staphyloccoccus aureus. J. Food Prot. 44: 531-536.

Liu, H., Chaudhary, D., Yusa, S., Tade, M. O. 2011. Preparation and characterization of sorbitol modified nanoclay with high amylose bionanocomposites. Carbohydrate Polymers. 85(1): 97-104.

Lueck, E. 1976. Sorbic acid as a food preservative. Int. Flavors Food Addit. 1.7: 122-138. Mariam, K. J.; Hiasa, H. 1997, Mechanism of quinolone action. A drug-induced structural perturbation of the DNA precedes strand cleavage by topoisomerase IV. J Biol Chem. 272(14): 9401-9409.

Moir, C. J., and M. J. Eyles. 1992. Inhibition, injury, and inactivation of four psychrotrophic foodborne bacteria by the preservatives methyl p-hydroxybenzoate and potassium sorbate. J. Food Prot. 55: 360-366.

Pathania, R., Zlitni, S., Barker, C., Das, R., Gerritsma, D. A., Lebert, J. et al. 2009. Chemical genomics in Escherichia coli identifies an inhibitor of bacterial lipoprotein targeting. Nat Chem Biol. 5: 849-856.

Reddy, N. R., Pierson, M. D., Lechowich, R. V. 1982. Inhibition of *Clostridium botulinum* by antioxidants phenols and related compounds. Appl. Environ. Microbiol. 43: 835-839.

Seong, I. K., You, H. B. 2001. pH-Induced Volume-Phase Transition of Hydrogels Containing Sulfonamide Side Group by Reversible Crystal Formation. Macromolecules. 34: 8173-8178.

Shulamit, L., Michael, S. S. 2008. Crystallinity and Cross-Linking in Porous Polymers Synthesized from Long Side Chain Monomers through Emulsion Templating. Macromolecules. 41: 3930-3938.

Sofos, J. N., Busta, F. F. 1981. Antimicrobialactivity of sorbate. J. Food Prot. 44: 614-618.

Sperling, L. H. 2001. Introduction to Physical Polymer Science. $3^{rd}$ Edition. New York, Wiley.

Xu, Y. X., Kim, K. M., Hanna, M. A., Nag, D. 2005. Chitosan-starch composite film: preparation and characterization. Industrial Crops and Products. 21: 185-192.

What is claimed is:

1. A composition of matter comprising an antimicrobial compound, said composition comprising a compound selected from JA-144, TH-04 or TH-08 or combination thereof, said compound having the following formula:

JA-144

TH-04

TH-08 or pharmaceutically acceptable salts thereof.

2. The composition of matter of claim 1 further comprising a carrier.

3. The composition of matter of claim 2, wherein said carrier comprises a pharmaceutically acceptable excipient.

4. The composition of matter of claim 3, comprising a composition for topical administration.

5. The composition of matter of claim 3, comprising a composition for systemic administration.

6. The composition of matter of claim 2, wherein said carrier comprises a film.

7. The composition of matter of claim 6, wherein said compound is JA-144.

8. The composition of matter of claim 6, wherein said film comprises an edible film.

9. The composition of matter of claim 8, wherein said compound is JA-144.

10. The composition of matter of claim 6, wherein said film comprises a package.

11. The composition of matter of claim 10, wherein said compound is TH-4 or TH-8 or combination thereof.

12. A method of treating a subject in need of treatment for a bacterial infection, said method comprising administering to said subject an effective amount of a composition comprising a compound of JA-144, TH-04 or TH-08 or combination thereof, having the following formula:

JA-144

TH-04

TH-08 or pharmaceutically acceptable salts thereof.

13. The method of claim 12, said composition further comprising a carrier.

14. The method of claim 12, wherein said carrier comprises a pharmaceutically acceptable excipient.

15. The method of claim 12, wherein said subject is a mammal.

16. The method of claim 12, wherein said subject is poultry and said bacterial infection comprises a Campylobacteria infection.

17. A method of inhibiting bacterial growth on a surface, the method comprising contacting said surface with a composition of matter comprising an effective amount of a compound of JA-144, TH-04 or TH-08 or combination thereof, having the following formula:

JA-144

TH-04

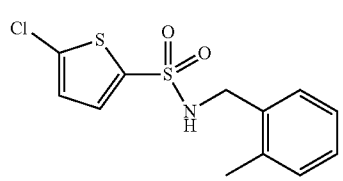
TH-08
or pharmaceutically acceptable salts thereof.
18. The method of claim 17, wherein said compositions comprises a carrier.
19. The method of claim 18, wherein said carrier comprises a film.
20. The method of claim 18, wherein said carrier comprises an edible film.
* * * * *